(12) United States Patent
Fangrow et al.

(10) Patent No.: US 12,280,249 B2
(45) Date of Patent: Apr. 22, 2025

(54) SYSTEMS, METHODS, AND COMPONENTS FOR TRAPPING AIR BUBBLES IN MEDICAL FLUID TRANSFER MODULES AND SYSTEMS

(71) Applicant: ICU Medical, Inc., San Clemente, CA (US)

(72) Inventors: Thomas F. Fangrow, Mission Viejo, CA (US); Jay Hachey, Newport Beach, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 18/620,577

(22) Filed: Mar. 28, 2024

(65) Prior Publication Data
US 2025/0058057 A1     Feb. 20, 2025

Related U.S. Application Data

(63) Continuation of application No. 18/170,838, filed on Feb. 17, 2023, now Pat. No. 11,951,293, which is a
(Continued)

(51) Int. Cl.
    *A61M 5/36*         (2006.01)
    *A61M 5/145*       (2006.01)
    (Continued)

(52) U.S. Cl.
    CPC .......... *A61M 5/36* (2013.01); *A61M 5/14546* (2013.01); *A61M 5/16813* (2013.01);
    (Continued)

(58) Field of Classification Search
    CPC ................ A61M 5/36; A61M 5/14546; A61M 5/16813; A61M 5/38; A61M 39/223;
    (Continued)

(56) References Cited

U.S. PATENT DOCUMENTS 1,923,501 A     8/1933   Perry
2,597,699 A     5/1952   Bauer
(Continued)

FOREIGN PATENT DOCUMENTS

CN            1707379        12/2005
CN            101244297      8/2008
(Continued)

OTHER PUBLICATIONS

U.S. Appl. No. 29/571,547, filed Jul. 19, 2016, Shauver et al.
(Continued)

*Primary Examiner* — Christopher P Jones
*Assistant Examiner* — Phillip Y Shao
(74) *Attorney, Agent, or Firm* — Knobbe, Martens, Olson & Bear, LLP

(57) ABSTRACT

Bubble traps for use in medical fluid lines and medical fluid bubble trap systems are disclosed herein. In some embodiments, the bubble trap is configured to trap gas (e.g., air) that flows into the bubble trap from a fluid line. In some embodiments, the bubble trap includes an inlet and an outlet and a chamber between the inlet and the outlet. For example, in some embodiments, the bubble trap is configured to inhibit gas from flowing into the outlet once gas flows into the chamber from the inlet. In some embodiments, the bubble trap is in fluid communication with a source container, a destination container, and/or a patient.

12 Claims, 24 Drawing Sheets

Related U.S. Application Data continuation of application No. 17/240,021, filed on Apr. 26, 2021, now Pat. No. 11,583,637, which is a continuation of application No. 16/255,710, filed on Jan. 23, 2019, now Pat. No. 11,020,541, which is a continuation of application No. PCT/US2017/043761, filed on Jul. 25, 2017.

(60) Provisional application No. 62/366,509, filed on Jul. 25, 2016.

(51) Int. Cl.
    *A61M 5/168* (2006.01)
    *A61M 5/38* (2006.01)
    *A61M 39/22* (2006.01)
    *A61M 5/14* (2006.01)
    *A61M 39/00* (2006.01)

(52) U.S. Cl.
    CPC ............ *A61M 5/38* (2013.01); *A61M 39/223* (2013.01); *A61M 5/14* (2013.01); *A61M 5/1413* (2013.01); *A61M 5/16831* (2013.01); *A61M 2039/0009* (2013.01); *A61M 39/22* (2013.01); *A61M 2039/229* (2013.01); *A61M 2205/3327* (2013.01); *A61M 2205/3379* (2013.01); *A61M 2205/3561* (2013.01); *A61M 2205/502* (2013.01); *A61M 2205/52* (2013.01)

(58) Field of Classification Search
    CPC .. A61M 5/14; A61M 5/1413; A61M 5/16831; A61M 39/22; A61M 2039/0009; A61M 2039/229; A61M 2205/3327; A61M 2205/3379; A61M 2205/3561; A61M 2205/502; A61M 2205/52
    See application file for complete search history.

(56) References Cited

U.S. PATENT DOCUMENTS

| | | | |
|---|---|---|---|
| 3,157,201 | A | 11/1964 | Littmann |
| 3,204,633 | A | 9/1965 | Hofstra et al. |
| 3,295,297 | A | 1/1967 | Collins |
| 3,344,785 | A | 10/1967 | Hamilton |
| D222,956 | S | 2/1972 | Sato |
| D222,957 | S | 2/1972 | Sato |
| 3,778,973 | A | 12/1973 | Martinez |
| 3,803,810 | A | 4/1974 | Rosenberg |
| 3,834,124 | A | 9/1974 | Ichikawa |
| D236,163 | S | 7/1975 | Manno |
| 3,935,883 | A | 2/1976 | Stach et al. |
| 4,005,710 | A | 2/1977 | Zeddies et al. |
| 4,084,606 | A | 4/1978 | Mittleman |
| 4,085,047 | A | 4/1978 | Thompson |
| 4,102,655 | A | 7/1978 | Jeffery et al. |
| 4,187,890 | A | 2/1980 | Stach et al. |
| 4,190,048 | A | 2/1980 | Sampson |
| 4,262,671 | A | 4/1981 | Kersten |
| 4,306,705 | A | 12/1981 | Svensson |
| 4,336,802 | A | 6/1982 | Stone et al. |
| 4,341,538 | A | 7/1982 | Vadnay et al. |
| 4,367,736 | A | 1/1983 | Gupton |
| D268,206 | S | 3/1983 | Kosako |
| D268,284 | S | 3/1983 | Manno et al. |
| 4,397,335 | A | 8/1983 | Doblar et al. |
| 4,410,321 | A | 10/1983 | Pearson et al. |
| 4,423,741 | A | 1/1984 | Levy |
| 4,519,792 | A | 5/1985 | Dawe |
| 4,534,758 | A | 8/1985 | Akers et al. |
| 4,559,043 | A | 12/1985 | Whitehouse et al. |
| 4,561,856 | A | 12/1985 | Cochran |
| 4,568,330 | A | 2/1986 | Kujawski et al. |
| 4,643,713 | A | 2/1987 | Vitala |
| 4,666,429 | A | 5/1987 | Stone |
| 4,670,007 | A | 6/1987 | Wheeldon et al. |
| 4,683,916 | A | 8/1987 | Raines |
| 4,755,172 | A | 7/1988 | Baldwin |
| 4,759,756 | A | 7/1988 | Forman et al. |
| 4,768,568 | A | 9/1988 | Fournier et al. |
| 4,778,450 | A | 10/1988 | Kamen |
| 4,819,684 | A | 4/1989 | Zaugg et al. |
| 4,828,587 | A | 5/1989 | Baurmeisiter et al. |
| 4,863,429 | A | 9/1989 | Baldwin |
| D305,165 | S | 12/1989 | Rudolph et al. |
| 4,922,975 | A | 5/1990 | Polaschegg |
| 4,936,841 | A | 6/1990 | Aoki et al. |
| 4,969,874 | A | 11/1990 | Michel et al. |
| 4,972,876 | A | 11/1990 | Kabata et al. |
| 4,976,590 | A | 12/1990 | Baldwin |
| 4,995,268 | A | 2/1991 | Ash et al. |
| 5,024,347 | A | 6/1991 | Baldwin |
| 5,037,390 | A | 8/1991 | Raines et al. |
| 5,114,580 | A | 5/1992 | Ahmad et al. |
| D328,952 | S | 8/1992 | Arioka |
| 5,176,658 | A | 1/1993 | Ranford |
| 5,211,201 | A | 5/1993 | Kamen et al. |
| 5,224,937 | A | 7/1993 | van der Heiden et al. |
| 5,254,096 | A | 10/1993 | Rondelet et al. |
| 5,256,155 | A | 10/1993 | Yerlikaya et al. |
| 5,288,290 | A | 2/1994 | Brody |
| 5,300,044 | A | 4/1994 | Classey et al. |
| D348,101 | S | 6/1994 | Poli et al. |
| 5,334,211 | A | 8/1994 | Shiber |
| 5,336,201 | A | 8/1994 | von der Decken |
| D352,778 | S | 11/1994 | Irvin |
| 5,378,231 | A | 1/1995 | Johnson et al. |
| 5,405,333 | A | 4/1995 | Richmond |
| 5,415,583 | A | 5/1995 | Brandt, Jr. |
| 5,423,791 | A | 6/1995 | Bartlett |
| 5,431,201 | A | 7/1995 | Torchia et al. |
| 5,439,451 | A | 8/1995 | Collinson et al. |
| 5,466,220 | A | 11/1995 | Brenneman |
| 5,609,572 | A | 3/1997 | Lang |
| 5,645,538 | A | 7/1997 | Richmond |
| 5,647,845 | A | 7/1997 | Haber et al. |
| 5,674,199 | A | 10/1997 | Brugger |
| 5,676,346 | A | 10/1997 | Leinsing |
| 5,685,866 | A | 11/1997 | Lopez |
| 5,776,345 | A | 7/1998 | Truitt et al. |
| 5,782,816 | A | 7/1998 | Werschmidt et al. |
| 5,807,312 | A | 9/1998 | Dzwonkiewicz |
| 5,810,792 | A | 9/1998 | Fangrow, Jr. et al. |
| 5,824,212 | A | 10/1998 | Brockhoff |
| 5,830,185 | A | 11/1998 | Block, Jr. |
| 5,871,110 | A | 2/1999 | Grimard et al. |
| 5,871,500 | A | 2/1999 | Jepson et al. |
| 5,885,270 | A | 3/1999 | Ortiz et al. |
| D408,079 | S | 4/1999 | Ellis |
| 5,897,526 | A | 4/1999 | Vaillancourt |
| 5,904,666 | A | 5/1999 | DeDecker et al. |
| 5,910,252 | A | 6/1999 | Truitt et al. |
| 5,935,106 | A | 8/1999 | Olsen |
| 5,947,951 | A | 9/1999 | Ortiz et al. |
| 5,968,014 | A | 10/1999 | Neftel et al. |
| 5,989,237 | A | 11/1999 | Fowles et al. |
| 6,059,747 | A | 5/2000 | Bruggeman et al. |
| 6,110,153 | A | 8/2000 | Davis et al. |
| RE36,871 | E | 9/2000 | Epstein et al. |
| 6,123,685 | A | 9/2000 | Reynolds |
| 6,132,404 | A | 10/2000 | Lopez |
| 6,152,900 | A | 11/2000 | Mayer |
| 6,171,484 | B1 | 1/2001 | Schnell et al. |
| 6,179,823 | B1 | 1/2001 | Niedospial, Jr. |
| 6,193,675 | B1 | 2/2001 | Kraus et al. |
| 6,193,689 | B1 | 2/2001 | Woodard |
| 6,202,708 | B1 | 3/2001 | Bynum |
| 6,221,041 | B1 | 4/2001 | Russo |
| 6,245,048 | B1 | 6/2001 | Fangrow, Jr. et al. |
| 6,287,289 | B1 | 9/2001 | Niedospial, Jr. |
| 6,302,864 | B1 | 10/2001 | Nowosielski |
| 6,425,497 | B1 | 7/2002 | Chu et al. |
| 6,474,375 | B2 | 11/2002 | Spero et al. |
| 6,485,472 | B1 | 11/2002 | Richmond |

(56) References Cited

U.S. PATENT DOCUMENTS

| | | |
|---|---|---|
| 6,537,356 B1 | 3/2003 | Soriano |
| 6,551,299 B2 | 4/2003 | Miyoshi et al. |
| 6,558,365 B2 | 5/2003 | Zinger et al. |
| 6,572,256 B2 | 6/2003 | Seaton et al. |
| 6,585,229 B2 | 7/2003 | Cote, Sr. et al. |
| 6,590,167 B2 | 7/2003 | Clare |
| 6,599,273 B1 | 7/2003 | Lopez |
| 6,623,455 B2 | 9/2003 | Small et al. |
| 6,629,956 B1 | 10/2003 | Polidoro et al. |
| 6,651,956 B2 | 11/2003 | Miller |
| 6,663,586 B2 | 12/2003 | Verkaart et al. |
| 6,689,108 B2 | 2/2004 | Lavi et al. |
| 6,699,230 B2 | 3/2004 | Jaafar et al. |
| 6,711,460 B1 | 3/2004 | Reese |
| 6,726,672 B1 | 4/2004 | Hanly et al. |
| 6,793,651 B1 | 9/2004 | Bennett et al. |
| 6,813,868 B2 | 11/2004 | Baldwin et al. |
| 6,854,620 B2 | 2/2005 | Ramet |
| 6,877,530 B2 | 4/2005 | Osborne et al. |
| 6,908,459 B2 | 6/2005 | Harding et al. |
| 6,915,823 B2 | 7/2005 | Osborne et al. |
| 6,948,522 B2 | 9/2005 | Newbrough et al. |
| 6,953,450 B2 | 10/2005 | Baldwin et al. |
| 6,985,870 B2 | 1/2006 | Martucci et al. |
| 6,991,002 B2 | 1/2006 | Osborne et al. |
| 6,994,315 B2 | 2/2006 | Ryan et al. |
| 6,997,917 B2 | 2/2006 | Niedospial, Jr. et al. |
| 7,006,894 B2 | 2/2006 | De La Huerga |
| 7,017,623 B2 | 3/2006 | Tribble et al. |
| 7,086,431 B2 | 8/2006 | D'Antonio et al. |
| 7,108,024 B2 | 9/2006 | Navarro |
| 7,117,901 B2 | 10/2006 | Martinell Gisper-Sauch et al. |
| 7,117,902 B2 | 10/2006 | Osborne |
| 7,128,105 B2 | 10/2006 | Tribble et al. |
| 7,163,031 B2 | 1/2007 | Graves et al. |
| 7,163,035 B2 | 1/2007 | Khan et al. |
| 7,175,615 B2 | 2/2007 | Hanly et al. |
| 7,194,336 B2 | 3/2007 | DiGianfilippo et al. |
| 7,260,447 B2 | 8/2007 | Osborne |
| 7,317,967 B2 | 1/2008 | DiGianfilippo et al. |
| 7,343,224 B2 | 3/2008 | DiGianfilippo et al. |
| 7,343,943 B2 | 3/2008 | Khan et al. |
| 7,351,226 B1 | 4/2008 | Herskowitz |
| 7,354,426 B2 | 4/2008 | Young |
| 7,392,638 B2 | 7/2008 | Baldwin et al. |
| 7,396,051 B2 | 7/2008 | Baldwin et al. |
| 7,398,802 B2 | 7/2008 | Baker |
| 7,418,981 B2 | 9/2008 | Baker et al. |
| 7,442,186 B2 | 10/2008 | Blomquist |
| 7,488,311 B2 | 2/2009 | Domkowski et al. |
| 7,499,581 B2 | 3/2009 | Tribble et al. |
| 7,527,619 B2 | 5/2009 | Domkowski et al. |
| 7,530,211 B2 | 5/2009 | McErlean et al. |
| 7,530,974 B2 | 5/2009 | Domkowski et al. |
| 7,538,858 B2 | 5/2009 | Mackey |
| D594,120 S | 6/2009 | Berberich et al. |
| D596,291 S | 7/2009 | Berberich et al. |
| 7,566,326 B2 | 7/2009 | Duchon et al. |
| 7,610,115 B2 | 10/2009 | Rob et al. |
| 7,630,788 B1 | 12/2009 | Reese |
| 7,630,789 B2 | 12/2009 | Broadfield et al. |
| 7,632,261 B2 | 12/2009 | Zinger et al. |
| 7,654,976 B2 | 2/2010 | Peterson et al. |
| 7,681,606 B2 | 3/2010 | Khan et al. |
| 7,685,026 B1 | 3/2010 | McGrady et al. |
| D616,092 S | 5/2010 | Domkowski et al. |
| 7,717,897 B2 | 5/2010 | Burg et al. |
| D620,108 S | 7/2010 | Eitenmueller et al. |
| 7,753,085 B2 | 7/2010 | Tribble et al. |
| 7,758,560 B2 | 7/2010 | Connell et al. |
| 7,789,850 B2 | 9/2010 | Roger |
| 7,814,731 B2 | 10/2010 | Bender et al. |
| 7,850,051 B2 | 12/2010 | Py et al. |
| 7,867,215 B2 | 1/2011 | Akerlund et al. |
| 7,882,863 B2 | 2/2011 | Pestotnik et al. |
| 7,900,658 B2 | 3/2011 | Osborne et al. |
| 7,913,720 B2 | 3/2011 | Tribble et al. |
| 7,963,201 B2 | 6/2011 | Willoughby et al. |
| 7,963,954 B2 | 6/2011 | Kavazov |
| 7,967,202 B2 | 6/2011 | Durrell et al. |
| 7,981,381 B2 | 7/2011 | Lurvey et al. |
| 8,034,041 B2 | 10/2011 | Domkowski et al. |
| 8,037,659 B2 | 10/2011 | Osborne et al. |
| 8,075,545 B2 | 12/2011 | Moy et al. |
| 8,091,727 B2 | 1/2012 | Domkowski |
| 8,091,860 B2 | 1/2012 | Thompson et al. |
| 8,104,644 B2 | 1/2012 | Py et al. |
| 8,117,809 B2 | 2/2012 | McErlean et al. |
| 8,140,351 B2 | 3/2012 | Tribble et al. |
| 8,141,601 B2 | 3/2012 | Fehr et al. |
| 8,151,835 B2 | 4/2012 | Khan et al. |
| 8,162,903 B2 | 4/2012 | Reilly et al. |
| 8,162,914 B2 | 4/2012 | Kraushaar et al. |
| 8,162,915 B2 | 4/2012 | Brandenburger et al. |
| D660,423 S | 5/2012 | Hermle |
| 8,172,823 B2 | 5/2012 | Rondeau et al. |
| 8,182,744 B2 | 5/2012 | Mlodzinski et al. |
| 8,197,459 B2 | 6/2012 | Jansen et al. |
| 8,206,367 B2 | 6/2012 | Warren et al. |
| D664,647 S | 7/2012 | Becker |
| D664,648 S | 7/2012 | Becker |
| D664,649 S | 7/2012 | Becker |
| 8,209,941 B2 | 7/2012 | Osborne et al. |
| 8,216,207 B2 | 7/2012 | Moy et al. |
| 8,220,503 B2 | 7/2012 | Tribble et al. |
| 8,220,504 B2 | 7/2012 | Hartman et al. |
| 8,221,382 B2 | 7/2012 | Moy et al. |
| 8,225,824 B2 | 7/2012 | Eliuk et al. |
| 8,225,826 B2 | 7/2012 | Horppu et al. |
| 8,231,567 B2 | 7/2012 | Tennican et al. |
| 8,231,749 B2 | 7/2012 | Dent et al. |
| 8,241,265 B2 | 8/2012 | Moy et al. |
| D667,946 S | 9/2012 | Levesque et al. |
| 8,267,129 B2 | 9/2012 | Doherty et al. |
| 8,267,912 B2 | 9/2012 | Ferris |
| 8,287,513 B2 | 10/2012 | Ellstrom et al. |
| 8,328,082 B1 | 12/2012 | Bochenko et al. |
| 8,336,587 B2 | 12/2012 | Rosenquist et al. |
| 8,356,644 B2 | 1/2013 | Chong et al. |
| 8,356,645 B2 | 1/2013 | Chong et al. |
| 8,357,137 B2 | 1/2013 | Yandell |
| 8,374,887 B1 | 2/2013 | Alexander |
| 8,381,776 B2 | 2/2013 | Horppu |
| 8,382,696 B2 | 2/2013 | Beiriger et al. |
| 8,386,070 B2 | 2/2013 | Eliuk et al. |
| 8,403,905 B2 | 3/2013 | Yow |
| 8,409,165 B2 | 4/2013 | Niedospial, Jr. et al. |
| 8,414,554 B2 | 4/2013 | Garfield et al. |
| 8,414,556 B2 | 4/2013 | Garfield et al. |
| 8,425,487 B2 | 4/2013 | Beiriger et al. |
| 8,430,859 B2 | 4/2013 | McConnell |
| 8,449,521 B2 | 5/2013 | Thorne, Jr. et al. |
| D687,948 S | 8/2013 | Levesque et al. |
| 8,506,548 B2 | 8/2013 | Okiyama |
| 8,522,832 B2 | 9/2013 | Lopez et al. |
| 8,551,037 B2 | 10/2013 | Suchecki et al. |
| 8,562,583 B2 | 10/2013 | Akerlund et al. |
| 8,567,235 B2 | 10/2013 | Bojan et al. |
| 8,571,708 B2 | 10/2013 | Rob et al. |
| 8,562,584 B2 | 11/2013 | Beiriger et al. |
| 8,602,067 B2 | 12/2013 | Kuhni et al. |
| 8,608,723 B2 | 12/2013 | Lev et al. |
| 8,622,985 B2 | 1/2014 | Ellstrom |
| 8,636,720 B2 | 1/2014 | Truitt et al. |
| 8,639,525 B2 | 1/2014 | Levine et al. |
| 8,679,075 B2 | 3/2014 | Lurvey et al. |
| 8,684,994 B2 | 4/2014 | Lev et al. |
| 8,701,696 B2 | 4/2014 | Guala |
| 8,702,675 B2 | 4/2014 | Imai |
| 8,720,496 B2 | 5/2014 | Huwiler et al. |
| 8,721,612 B2 | 5/2014 | Domkowski et al. |
| 8,721,614 B2 | 5/2014 | Takemoto et al. |
| 8,721,627 B2 | 5/2014 | Alpert |
| D706,415 S | 6/2014 | Levesque et al. |

(56) References Cited

U.S. PATENT DOCUMENTS

| | | |
|---|---|---|
| 8,753,325 B2 | 6/2014 | Lev et al. |
| 8,763,798 B2 | 7/2014 | Paul |
| 8,795,231 B2 | 8/2014 | Chong et al. |
| 8,801,689 B2 | 8/2014 | Moy et al. |
| 8,821,436 B2 | 9/2014 | Mosler et al. |
| 8,834,444 B2 | 9/2014 | Domkowski |
| 8,852,147 B2 | 10/2014 | Callan et al. |
| 8,864,725 B2 | 10/2014 | Ranalletta et al. |
| 8,864,737 B2 | 10/2014 | Hasegawa et al. |
| 8,870,832 B2 | 10/2014 | Raday et al. |
| 8,882,739 B2 | 11/2014 | Domkowski et al. |
| 8,894,627 B2 | 11/2014 | Garfield et al. |
| 8,911,421 B2 | 12/2014 | Domkowski et al. |
| D721,803 S | 1/2015 | Dubach |
| 8,926,554 B2 | 1/2015 | Okuda et al. |
| 8,958,112 B2 | 2/2015 | Matsui et al. |
| D724,198 S | 3/2015 | Oostman et al. |
| 8,973,622 B2 | 3/2015 | Lopez et al. |
| 8,979,792 B2 | 3/2015 | Lev et al. |
| 9,033,006 B2 | 5/2015 | Perazzo et al. |
| 9,043,019 B2 | 5/2015 | Eliuk et al. |
| 9,056,164 B2 | 6/2015 | Tate et al. |
| 9,057,363 B2 | 6/2015 | Capone |
| 9,057,370 B2 | 6/2015 | Mundt et al. |
| 9,060,923 B2 | 6/2015 | Hossainy |
| 9,061,130 B2 | 6/2015 | Truitt et al. |
| 9,076,115 B2 | 7/2015 | Utech et al. |
| 9,079,686 B2 | 7/2015 | Domkowski et al. |
| 9,089,474 B2 | 7/2015 | Cederschiöld |
| 9,089,647 B2 | 7/2015 | Haenggi et al. |
| 9,101,717 B2 | 8/2015 | Mansour et al. |
| 9,114,242 B2 | 8/2015 | Fangrow et al. |
| 9,132,062 B2 | 9/2015 | Fangrow |
| 9,132,063 B2 | 9/2015 | Lev et al. |
| 9,139,316 B2 | 9/2015 | Husnu et al. |
| 9,144,646 B2 | 9/2015 | Barron, III et al. |
| 9,149,576 B2 | 10/2015 | Bullington et al. |
| 9,198,832 B2 | 12/2015 | Moy et al. |
| 9,211,231 B2 | 12/2015 | Mansour et al. |
| 9,212,762 B2 | 12/2015 | Duncan |
| 9,220,661 B2 | 12/2015 | Garfield et al. |
| D747,472 S | 1/2016 | Bradley et al. |
| 9,227,048 B2 | 1/2016 | Frattini |
| 9,241,875 B2 | 1/2016 | Davis et al. |
| 9,242,039 B2 | 1/2016 | Valk et al. |
| 9,270,890 B2 | 2/2016 | Okuma et al. |
| 9,345,640 B2 | 5/2016 | Mosler |
| 9,345,641 B2 | 5/2016 | Kraus et al. |
| 9,345,643 B2 | 5/2016 | Okiyama |
| 9,381,135 B2 | 7/2016 | Reynolds et al. |
| 9,381,137 B2 | 7/2016 | Garfield et al. |
| 9,382,021 B2 | 7/2016 | Tribble et al. |
| 9,402,786 B2 | 8/2016 | Petrone |
| 9,408,966 B2 | 8/2016 | Kamen |
| 9,466,088 B2 | 10/2016 | Perazzo et al. |
| 9,474,690 B2 | 10/2016 | Ranalletta et al. |
| 9,475,019 B2 | 10/2016 | Kaucky et al. |
| 9,481,477 B2 | 11/2016 | Kjar |
| D774,192 S | 12/2016 | Fuchs |
| D775,325 S | 12/2016 | Larson et al. |
| 9,511,989 B2 | 12/2016 | Lopez et al. |
| 9,561,893 B2 | 2/2017 | Root et al. |
| 9,579,255 B2 | 2/2017 | Eliuk et al. |
| 9,615,997 B2 | 4/2017 | Fangrow |
| 9,629,955 B2 | 4/2017 | Bresina et al. |
| 9,744,102 B2 | 8/2017 | Kubo |
| 9,770,388 B2 | 9/2017 | Noike et al. |
| 9,775,778 B2 | 10/2017 | Qiu et al. |
| 9,801,787 B2 | 10/2017 | Py |
| 9,802,171 B2 | 10/2017 | Konrad, Jr. et al. |
| 9,802,172 B2 | 10/2017 | Konrad, Jr. et al. |
| D803,396 S | 11/2017 | Oberkircher et al. |
| 9,827,163 B2 | 11/2017 | Lopez et al. |
| 9,827,680 B2 | 11/2017 | Davey et al. |
| D804,651 S | 12/2017 | Loonan |
| 9,833,605 B2 | 12/2017 | Sanders et al. |
| 9,849,236 B2 | 12/2017 | Hachey et al. |
| 9,883,987 B2 | 2/2018 | Lopez et al. |
| 9,930,297 B2 | 3/2018 | Alexander et al. |
| 9,931,276 B2 | 4/2018 | Lopez et al. |
| D819,414 S | 6/2018 | Solomon |
| 10,106,278 B2 | 10/2018 | Chang et al. |
| 10,143,985 B2 | 12/2018 | Brown et al. |
| D837,983 S | 1/2019 | Fangrow |
| 10,181,186 B2 | 1/2019 | Kriheli et al. |
| 10,188,849 B2 | 1/2019 | Fangrow |
| 10,189,616 B2 | 1/2019 | Kraft |
| D846,146 S | 4/2019 | Amos et al. |
| 10,259,608 B2 | 4/2019 | Fianchini et al. |
| D851,745 S | 6/2019 | Shauver et al. |
| 10,307,338 B2 | 6/2019 | Hellenbrand |
| 10,314,764 B2 | 6/2019 | Lopez et al. |
| 10,314,765 B2 | 6/2019 | Lopez et al. |
| 10,315,174 B2 | 6/2019 | Konrad, Jr. et al. |
| 10,327,987 B1 | 6/2019 | Bochenko et al. |
| 10,327,988 B2 | 6/2019 | Tribble et al. |
| 10,336,477 B2 | 7/2019 | Perazzo et al. |
| 10,417,758 B1 | 9/2019 | Alexander |
| 10,420,927 B2 | 9/2019 | Fangrow |
| 10,494,126 B2 | 12/2019 | Joplin |
| 10,503,873 B2 | 12/2019 | Prince et al. |
| 10,512,885 B2 | 12/2019 | Janders et al. |
| D874,644 S | 2/2020 | Shauver et al. |
| 10,554,937 B2 | 2/2020 | Alexander et al. |
| 10,556,062 B2 | 2/2020 | Simpson et al. |
| 10,576,211 B2 | 3/2020 | Hang et al. |
| D887,577 S | 6/2020 | Shor et al. |
| 10,791,975 B2 | 10/2020 | Wilkinson et al. |
| D905,228 S | 12/2020 | Shauver et al. |
| 11,007,119 B2 | 5/2021 | Lopez et al. |
| 11,020,541 B2 | 6/2021 | Fangrow et al. |
| 11,033,459 B2 | 6/2021 | Ariagno et al. |
| 11,135,416 B2 | 10/2021 | Fangrow |
| D943,732 S | 2/2022 | Shauver et al. |
| D948,044 S | 4/2022 | Fangrow |
| 11,439,570 B2 | 9/2022 | Lopez et al. |
| 11,439,571 B2 | 9/2022 | Lopez et al. |
| 11,541,171 B2 | 1/2023 | Hachey et al. |
| 11,583,637 B2 | 2/2023 | Fangrow et al. |
| 11,806,308 B2 | 11/2023 | Lopez et al. |
| 11,865,295 B2 | 1/2024 | Fangrow |
| D1,018,849 S | 3/2024 | Fangrow |
| 11,951,293 B2 | 4/2024 | Fangrow et al. |
| 12,023,304 B2 | 7/2024 | Lopez et al. |
| 2002/0017328 A1 | 2/2002 | Loo |
| 2002/0064880 A1 | 5/2002 | Merten et al. |
| 2002/0085952 A1 | 7/2002 | Ellingboe et al. |
| 2002/0095121 A1 | 7/2002 | Norton et al. |
| 2002/0179544 A1 | 12/2002 | Johnson et al. |
| 2002/0189712 A1 | 12/2002 | Safabash |
| 2003/0023226 A1 | 1/2003 | Lopez |
| 2003/0153895 A1 | 8/2003 | Leinsing |
| 2003/0188897 A1 | 10/2003 | Ludi et al. |
| 2003/0236500 A1 | 12/2003 | Scheu |
| 2004/0031756 A1 | 2/2004 | Suzuki et al. |
| 2004/0035743 A1 | 2/2004 | Tighe et al. |
| 2004/0073161 A1 | 4/2004 | Tachibana |
| 2004/0087888 A1 | 5/2004 | Digianfilippo et al. |
| 2004/0116891 A1 | 6/2004 | Curutcharry |
| 2004/0118477 A1 | 6/2004 | Desmond |
| 2004/0138627 A1 | 7/2004 | Forrest |
| 2004/0225274 A1 | 11/2004 | Jansen et al. |
| 2005/0033260 A1 | 2/2005 | Kubo et al. |
| 2005/0059952 A1 | 3/2005 | Giuliano et al. |
| 2005/0096627 A1 | 5/2005 | Howard |
| 2005/0131357 A1 | 6/2005 | Denton et al. |
| 2005/0230575 A1 | 10/2005 | Zelenski et al. |
| 2005/0252572 A1 | 11/2005 | Khan et al. |
| 2005/0252574 A1 | 11/2005 | Khan et al. |
| 2005/0267413 A1 | 12/2005 | Wang et al. |
| 2006/0048844 A1 | 3/2006 | Merrill |
| 2006/0064053 A1 | 3/2006 | Bollish et al. |
| 2006/0169348 A1 | 8/2006 | Yigal |
| 2006/0259195 A1 | 11/2006 | Eliuk et al. |

(56) References Cited

U.S. PATENT DOCUMENTS

| | | |
|---|---|---|
| 2007/0007478 A1 | 1/2007 | Leinsing et al. |
| 2007/0017583 A1 | 1/2007 | Fangrow |
| 2007/0088252 A1 | 4/2007 | Pestotnik et al. |
| 2007/0088313 A1 | 4/2007 | Zinger et al. |
| 2007/0106244 A1 | 5/2007 | Mosler et al. |
| 2007/0151984 A1 | 7/2007 | Baker et al. |
| 2007/0169836 A1 | 7/2007 | Djurle et al. |
| 2007/0244447 A1 | 10/2007 | Capitaine et al. |
| 2007/0287953 A1 | 12/2007 | Ziv et al. |
| 2008/0059228 A1 | 3/2008 | Bossi et al. |
| 2008/0065006 A1 | 3/2008 | Roger et al. |
| 2008/0077116 A1 | 3/2008 | Dailey et al. |
| 2008/0086088 A1 | 4/2008 | Malcom |
| 2008/0086094 A1 | 4/2008 | Peters |
| 2008/0114328 A1 | 5/2008 | Doherty et al. |
| 2008/0125897 A1 | 5/2008 | DiGianfilippo et al. |
| 2008/0169043 A1 | 7/2008 | Osborne et al. |
| 2008/0169044 A1 | 7/2008 | Osborne et al. |
| 2008/0172024 A1 | 7/2008 | Yow |
| 2008/0177222 A1 | 7/2008 | Roger |
| 2008/0195416 A1 | 8/2008 | Tribble et al. |
| 2008/0199353 A1 | 8/2008 | Mlodzinski et al. |
| 2008/0269680 A1 | 10/2008 | Ibranyan et al. |
| 2008/0287920 A1 | 11/2008 | Fangrow et al. |
| 2009/0012449 A1 | 1/2009 | Lee et al. |
| 2009/0050216 A1 | 2/2009 | Trocki et al. |
| 2009/0067973 A1 | 3/2009 | Eliuk et al. |
| 2009/0069743 A1 | 3/2009 | Krishnamoorthy et al. |
| 2009/0082649 A1 | 3/2009 | Muller et al. |
| 2009/0088687 A1 | 4/2009 | Yardimci et al. |
| 2009/0099547 A1 | 4/2009 | Radmer |
| 2009/0101576 A1 | 4/2009 | Rohde et al. |
| 2009/0126825 A1 | 5/2009 | Eliuk et al. |
| 2009/0145509 A1 | 6/2009 | Baker et al. |
| 2009/0149743 A1 | 6/2009 | Barron et al. |
| 2009/0154764 A1 | 6/2009 | Khan et al. |
| 2009/0163860 A1 | 6/2009 | Patrick et al. |
| 2009/0177149 A1 | 7/2009 | Childers et al. |
| 2009/0198215 A1 | 8/2009 | Chong et al. |
| 2009/0223592 A1 | 9/2009 | Procyshyn et al. |
| 2009/0223990 A1 | 9/2009 | Bailey et al. |
| 2009/0254031 A1 | 10/2009 | Lee |
| 2009/0270832 A1 | 10/2009 | Vancaillie et al. |
| 2009/0306621 A1 | 12/2009 | Thome, Jr. et al. |
| 2010/0024904 A1 | 2/2010 | Hoffman et al. |
| 2010/0049157 A1 | 2/2010 | Fangrow |
| 2010/0121246 A1 | 5/2010 | Peters et al. |
| 2010/0245056 A1 | 9/2010 | Braun et al. |
| 2010/0276034 A1 | 11/2010 | Gonnelli et al. |
| 2010/0280430 A1 | 11/2010 | Caleffi et al. |
| 2010/0286606 A1 | 11/2010 | Ding |
| 2011/0004143 A1 | 1/2011 | Beiriger et al. |
| 2011/0004187 A1 | 1/2011 | Beiriger |
| 2011/0067781 A1 | 3/2011 | Osborne |
| 2011/0087164 A1 | 4/2011 | Mosler et al. |
| 2011/0152757 A1 | 6/2011 | Beck et al. |
| 2011/0175347 A1 | 7/2011 | Okiyama |
| 2011/0178493 A1 | 7/2011 | Okiyama |
| 2011/0196304 A1 | 8/2011 | Kramer et al. |
| 2011/0204144 A1 | 8/2011 | Waugh et al. |
| 2011/0229517 A1 | 9/2011 | Strahlendorf et al. |
| 2011/0276031 A1 | 11/2011 | Hoang et al. |
| 2011/0305545 A1 | 12/2011 | Davis et al. |
| 2012/0157914 A1 | 1/2012 | Stroup |
| 2012/0067429 A1 | 3/2012 | Mosler et al. |
| 2012/0109077 A1 | 5/2012 | Ryan |
| 2012/0123298 A1 | 5/2012 | Mendels et al. |
| 2012/0302986 A1 | 11/2012 | Brem et al. |
| 2013/0006214 A1 | 1/2013 | Garfield et al. |
| 2013/0018356 A1 | 1/2013 | Prince et al. |
| 2013/0053815 A1 | 2/2013 | Mucientes et al. |
| 2013/0085439 A1 | 4/2013 | Sansoucy et al. |
| 2013/0102772 A1 | 4/2013 | Eshima et al. |
| 2013/0211332 A1 | 8/2013 | Beiriger et al. |
| 2013/0218121 A1 | 8/2013 | Waller et al. |
| 2013/0220484 A1 | 8/2013 | De Marco |
| 2013/0292004 A1 | 11/2013 | Ducret et al. |
| 2014/0020790 A1 | 1/2014 | Yuyama et al. |
| 2014/0039392 A1 | 2/2014 | Geipel et al. |
| 2014/0124087 A1 | 5/2014 | Anderson et al. |
| 2014/0135732 A1 | 5/2014 | Spronken et al. |
| 2014/0136229 A1 | 5/2014 | Levine et al. |
| 2014/0150925 A1 | 6/2014 | Sjogren et al. |
| 2014/0261727 A1 | 9/2014 | Mansour et al. |
| 2014/0261860 A1 | 9/2014 | Heath |
| 2014/0261877 A1 | 9/2014 | Ivosevic et al. |
| 2014/0263614 A1 | 9/2014 | Keefe et al. |
| 2014/0276386 A1 | 9/2014 | Mansour et al. |
| 2014/0276649 A1 | 9/2014 | Ivosevic et al. |
| 2014/0323970 A1 | 10/2014 | Duncan |
| 2014/0350949 A1 | 11/2014 | Utech et al. |
| 2015/0000784 A1 | 1/2015 | Jamaledine |
| 2015/0008664 A1 | 1/2015 | Tachizaki |
| 2015/0025453 A1 | 1/2015 | Ledford et al. |
| 2015/0040987 A1 | 2/2015 | Reichert et al. |
| 2015/0040988 A1 | 2/2015 | Reichert et al. |
| 2015/0041531 A1 | 2/2015 | Vavala et al. |
| 2015/0045772 A1 | 2/2015 | Reichert et al. |
| 2015/0082746 A1 | 3/2015 | Ivosevic et al. |
| 2015/0101707 A1 | 4/2015 | Ranalletta et al. |
| 2015/0119820 A1 | 4/2015 | Kanamoto |
| 2015/0123398 A1 | 5/2015 | Sanders et al. |
| 2015/0126958 A1 | 5/2015 | Sanders et al. |
| 2015/0133879 A1 | 5/2015 | Kanamoto et al. |
| 2015/0151041 A1 | 6/2015 | Yodfat et al. |
| 2015/0157536 A1 | 6/2015 | Qiu et al. |
| 2015/0161354 A1 | 6/2015 | Blomquist |
| 2015/0202382 A1 | 7/2015 | Juretich et al. |
| 2015/0202383 A1 | 7/2015 | Juretich et al. |
| 2015/0202384 A1 | 7/2015 | Juretich et al. |
| 2015/0202385 A1 | 7/2015 | Juretich et al. |
| 2015/0209230 A1 | 7/2015 | Lev et al. |
| 2015/0209233 A1 | 7/2015 | Fukuoka |
| 2015/0209495 A1 | 7/2015 | Biset et al. |
| 2015/0209510 A1 | 7/2015 | Burkholz et al. |
| 2015/0250680 A1 | 9/2015 | Browka et al. |
| 2015/0250681 A1 | 9/2015 | Lev et al. |
| 2015/0257977 A1 | 9/2015 | Bochenko et al. |
| 2015/0265500 A1 | 9/2015 | Russo et al. |
| 2015/0297451 A1 | 10/2015 | Mariei et al. |
| 2015/0297453 A1 | 10/2015 | Kim et al. |
| 2015/0297454 A1 | 10/2015 | Sanders et al. |
| 2015/0297456 A1 | 10/2015 | Mariei et al. |
| 2015/0297459 A1 | 10/2015 | Sanders et al. |
| 2015/0297460 A1 | 10/2015 | Mansour et al. |
| 2015/0297839 A1 | 10/2015 | Sanders et al. |
| 2015/0297881 A1 | 10/2015 | Sanders et al. |
| 2015/0314066 A1 | 11/2015 | Shimizu |
| 2015/0320992 A1 | 11/2015 | Bonnet et al. |
| 2015/0346013 A1 | 12/2015 | Feng et al. |
| 2015/0359709 A1 | 12/2015 | Kriheli et al. |
| 2015/0366758 A1 | 12/2015 | Noguchi et al. |
| 2016/0000653 A1 | 1/2016 | Kramer |
| 2016/0001003 A1 | 1/2016 | Perazzo et al. |
| 2016/0038373 A1 | 2/2016 | Ohlin |
| 2016/0038374 A1 | 2/2016 | Merhold et al. |
| 2016/0051446 A1 | 2/2016 | Lev et al. |
| 2016/0058666 A1 | 3/2016 | Strahlendorf et al. |
| 2016/0058667 A1 | 3/2016 | Kriheli |
| 2016/0081878 A1 | 3/2016 | Marks et al. |
| 2016/0101020 A1 | 4/2016 | Guala |
| 2016/0114922 A1 | 4/2016 | Bonhora et al. |
| 2016/0136051 A1 | 5/2016 | Lavi |
| 2016/0136412 A1 | 5/2016 | McKinnon et al. |
| 2016/0140315 A1 | 5/2016 | Diaz et al. |
| 2016/0158104 A1 | 6/2016 | Ali et al. |
| 2016/0158437 A1 | 6/2016 | Biasi et al. |
| 2016/0206511 A1 | 7/2016 | Garfield et al. |
| 2016/0213861 A1 | 7/2016 | Whitaker et al. |
| 2016/0213862 A1 | 7/2016 | Whitaker et al. |
| 2016/0256632 A1 | 9/2016 | Fangrow |
| 2016/0262981 A1 | 9/2016 | Carrez et al. |
| 2016/0310362 A1 | 10/2016 | Lane et al. |
| 2016/0331893 A1 | 11/2016 | Yeh et al. |

(56) References Cited

U.S. PATENT DOCUMENTS

| | | |
|---|---|---|
| 2016/0354281 A1 | 12/2016 | O'Neill et al. |
| 2017/0007501 A1 | 1/2017 | Schuldt-Lieb et al. |
| 2017/0020428 A1 | 1/2017 | Rogers et al. |
| 2017/0081168 A1 | 3/2017 | Seay et al. |
| 2017/0128666 A1 | 5/2017 | Davis |
| 2017/0129763 A1 | 5/2017 | Fangrow, Jr. |
| 2017/0146381 A1 | 5/2017 | Eckel et al. |
| 2017/0165435 A1 | 6/2017 | Green |
| 2017/0165436 A1 | 6/2017 | Haddad et al. |
| 2017/0255760 A1 | 9/2017 | Lee et al. |
| 2017/0312716 A1 | 11/2017 | Konrad, Jr. et al. |
| 2017/0354571 A1 | 12/2017 | David et al. |
| 2018/0028403 A1 | 2/2018 | Fangrow |
| 2018/0043323 A1 | 2/2018 | Janders et al. |
| 2018/0055738 A1 | 3/2018 | Chen et al. |
| 2018/0065097 A1 | 3/2018 | Konrad, Jr. et al. |
| 2018/0133667 A1 | 5/2018 | Lee et al. |
| 2018/0161244 A1 | 6/2018 | Lopez |
| 2018/0168930 A1 | 6/2018 | Tunesi |
| 2018/0168935 A1 | 6/2018 | Chen et al. |
| 2018/0177940 A1 | 6/2018 | Hachey et al. |
| 2018/0194505 A1 | 7/2018 | Amano et al. |
| 2018/0207063 A1 | 7/2018 | Lopez |
| 2018/0232497 A1 | 8/2018 | Hoffman et al. |
| 2018/0263850 A1 | 9/2018 | Schneider et al. |
| 2018/0344572 A1 | 12/2018 | Zollinger et al. |
| 2018/0353381 A1 | 12/2018 | Pak et al. |
| 2018/0353382 A1 | 12/2018 | Zollinger et al. |
| 2018/0354662 A1 | 12/2018 | Feith et al. |
| 2018/0357476 A1 | 12/2018 | Klumph |
| 2018/0360689 A1 | 12/2018 | Zollinger et al. |
| 2019/0019576 A1 | 1/2019 | DeCiccio et al. |
| 2019/0021947 A1 | 1/2019 | Bomgaars et al. |
| 2019/0056419 A1 | 2/2019 | Procyshyn et al. |
| 2019/0070405 A1 | 3/2019 | Fangrow |
| 2019/0091639 A1 | 3/2019 | Brown et al. |
| 2019/0105619 A1 | 4/2019 | Wilson et al. |
| 2019/0151569 A1 | 5/2019 | Fangrow et al. |
| 2019/0152663 A1 | 5/2019 | Kraft |
| 2019/0163876 A1 | 5/2019 | Remme et al. |
| 2019/0170663 A1 | 6/2019 | Pirkle et al. |
| 2019/0216683 A1 | 7/2019 | Yaegashi |
| 2019/0244466 A1 | 8/2019 | Berg et al. |
| 2019/0247280 A1 | 8/2019 | Hellenbrand |
| 2019/0262790 A1 | 8/2019 | Konrad, Jr. et al. |
| 2019/0275243 A1 | 9/2019 | Deck et al. |
| 2019/0307643 A1 | 10/2019 | Tribble et al. |
| 2019/0388302 A1 | 12/2019 | Schobel et al. |
| 2020/0016037 A1 | 1/2020 | Oda et al. |
| 2020/0066389 A1 | 2/2020 | Prince et al. |
| 2020/0093699 A1 | 3/2020 | Oda et al. |
| 2020/0113784 A1 | 4/2020 | Lopez et al. |
| 2020/0113785 A1 | 4/2020 | Lopez |
| 2020/0206492 A1 | 7/2020 | Fangrow |
| 2020/0289370 A1 | 9/2020 | Lopez |
| 2020/0297581 A1 | 9/2020 | Lopez et al. |
| 2021/0002008 A1 | 1/2021 | Min et al. |
| 2021/0121363 A1 | 4/2021 | Oda et al. |
| 2021/0259921 A1 | 8/2021 | Lopez et al. |
| 2021/0308012 A1 | 10/2021 | Tagliamento |
| 2022/0008711 A1 | 1/2022 | Fangrow |
| 2022/0054766 A1 | 2/2022 | Fangrow et al. |
| 2022/0379697 A1 | 12/2022 | Lopez |
| 2023/0390490 A1 | 12/2023 | Hachey |
| 2024/0033447 A1 | 2/2024 | Fangrow et al. |

FOREIGN PATENT DOCUMENTS

| | | |
|---|---|---|
| CN | 106860003 A | 6/2017 |
| CN | 107198658 A | 9/2017 |
| CN | 108210332 A | 6/2018 |
| DE | 202 16 791 U | 2/2003 |
| DE | 20 2004 014 868 | 11/2004 |
| EP | 0 577 354 | 1/1994 |
| EP | 0 521 460 B1 | 9/1995 |
| EP | 0 974 330 | 1/2000 |
| EP | 1 533 597 | 5/2005 |
| EP | 1 563 819 | 8/2005 |
| EP | 1 997 471 | 12/2008 |
| EP | 3 375 427 A1 | 9/2018 |
| JP | S55-156750 | 11/1980 |
| JP | 55-173339 | 12/1980 |
| JP | 56-95247 A | 8/1981 |
| JP | 62-189072 A | 8/1987 |
| JP | 06-343706 | 12/1994 |
| JP | 10-118158 A | 5/1998 |
| JP | 2001-190689 A | 7/2001 |
| JP | 2002-238979 A | 8/2002 |
| JP | 2002-355318 | 12/2002 |
| JP | 2003-144546 | 5/2003 |
| JP | 2003-199823 | 7/2003 |
| JP | 2003-225305 A | 8/2003 |
| JP | 2004-049497 | 2/2004 |
| JP | 2007-14618 A | 1/2007 |
| JP | 2007-215775 A | 8/2007 |
| KR | 2011-0019800 | 3/2011 |
| KR | 10-1574194 B1 | 12/2015 |
| WO | WO 1997/14493 | 4/1997 |
| WO | WO 1998/23353 | 6/1998 |
| WO | WO 1999/19012 | 4/1999 |
| WO | WO 1999/63547 | 12/1999 |
| WO | WO 2000/41751 | 7/2000 |
| WO | WO 2001/03757 | 1/2001 |
| WO | WO 2001/039874 | 6/2001 |
| WO | WO 2002/04065 | 1/2002 |
| WO | WO 2002/013890 | 2/2002 |
| WO | WO 2005/041846 | 5/2005 |
| WO | WO 2005/110007 | 11/2005 |
| WO | WO 2005/123162 | 12/2005 |
| WO | WO 2007/033013 | 3/2007 |
| WO | WO 2007/061424 | 5/2007 |
| WO | WO 2007/062315 | 5/2007 |
| WO | WO 2007/079305 | 7/2007 |
| WO | WO 2007/148708 | 12/2007 |
| WO | WO 2008/051998 | 5/2008 |
| WO | WO 2008/052140 | 5/2008 |
| WO | WO 2008/128074 | 10/2008 |
| WO | WO 2008/144447 | 11/2008 |
| WO | WO 2009/060419 | 5/2009 |
| WO | WO 2009/130147 | 10/2009 |
| WO | WO 2009/140511 | 11/2009 |
| WO | WO 2010/111546 | 9/2010 |
| WO | WO 2011/002853 | 1/2011 |
| WO | WO 2011/012313 | 2/2011 |
| WO | WO 2011/014525 | 2/2011 |
| WO | WO 2011/058545 | 5/2011 |
| WO | WO 2011/058548 | 5/2011 |
| WO | WO 2011/091542 | 8/2011 |
| WO | WO 2011/091543 | 8/2011 |
| WO | WO 2011/104711 | 9/2011 |
| WO | WO 2011/104712 | 9/2011 |
| WO | WO 2011/150037 | 12/2011 |
| WO | WO 2012/119225 | 9/2012 |
| WO | WO 2013/096911 | 6/2013 |
| WO | WO 2014/122643 | 8/2014 |
| WO | WO 2014/126473 | 8/2014 |
| WO | WO 2014/177347 | 11/2014 |
| WO | WO 2014/181320 | 11/2014 |
| WO | WO 2015/029020 | 3/2015 |
| WO | WO 2015/077184 | 5/2015 |
| WO | WO 2015/077466 | 5/2015 |
| WO | WO 2015/122921 | 8/2015 |
| WO | WO 2016/010909 | 1/2016 |
| WO | WO 2017/096072 | 6/2017 |
| WO | WO 2018/009996 | 1/2018 |
| WO | WO 2018/022640 | 2/2018 |

(56) References Cited

FOREIGN PATENT DOCUMENTS

| WO | WO 2019/018195 | 1/2019 |
|----|----------------|--------|
| WO | WO 2021/201884 | 10/2021 |

OTHER PUBLICATIONS

U.S. Appl. No. 29/586,575, filed Dec. 5, 2016, Fangrow.
Abbott "Plum A+," System Operating Manual (For use with List 11971-04) in 85 pages, May 2001.
Autoyec 50, from KRZ, Dec. 6, 2007.
B. Braun Medical Inc. Two-Bag Irrigation Set, Two Non-vented Spikes, dated Jul. 2012, in 1 page.
*Baxa Corp.* v. *McGaw Inc.* 981 F. Supp. 1348 (1997), Memorandum Opinion and Order, 14 pages.
BioExpert International Inc., Company overview, credentials for Rabih Jamaleddine, Nabil Kereknawi, and Danica Robillard Corso, copyright 2010 BioExpert International Inc. in 3 pages [retrieved on Jan. 6, 2015; Publication Date Unknown]; accessed on the world wide web at http://bioexpert.ca/about.html.
Burrows, et al., "Intravenous (IV) Fluidmaker IV. A Disposable Device for Preparation of Sterile Water for Injection in a Field Setting," Fort Detrick, US Army Biomedical Research & Development Laboratory, Sep. 1991. https://apps.dtc.mil/dtic/tr/fulltest/u2/a247385.pdf.
Canadian Office Action, re CA Application No. 2,768,985, dated Jun. 27, 2016.
Cato (Computer Aided Therapy for Oncology)—Reference Manual—Vienna, May 2005, 255 pgs.
Clearlink Needleless IV Access System, dated Aug. 2007, in 2 pages.
Cytocare, by Health Robotics, Brochure, Date Unknown, downloaded on May 25, 2012 from http://www.health-robotics.com/smartedit/downloads/en/cytocare7.pdf, 6 pages.
Exacta-Mix 2400, from Baxa, which appears to have a date of 2007, 2 pages.
Flickinger, Bruce, "Misperceptions Cloud the Issue of Sterile Drug Compounding," Jun. 2007.
Fox, Brent I., "Pharmacy Automation and Technology: Automated Intravenous Preparation: Robots for the Pharmacy," Hospital Pharmacy, vol. 44, Mar. 2009, pp. 255-257.
Grifols International, S.A., "PHOCUS Rx, Remote IV Compounding Validation" product brochure and "Product Description Sheet" in 13 pages [Publication Date unknown but may be May 29, 2013].
Healthmark, "Hospital Medication Preparation, Packaging and Dispensing" in 1 page [retrieved on Jan. 6, 2015; Publication Date Unknown]; accessed on the world wide web at http://www.healthmark.ca/2-en-Hospital-Medication-Preparation-Packaging-and-Dispensing.html.
Healthmark, "Hospital Medication Preparation, Packaging and Dispensing," Chemo Drug Preparation/Administration in 2 pages [retrieved on Jan. 6, 2015; Publication Date Unknown]; accessed on the world wide web at http://www.healthmark.ca/2-36-88-Chemo-Drug-Preparation-Administration_en.html.
Healthmark, "Hospital Medication Preparation, Packaging and Dispensing," Chemosphere, Sterile Chemo Compounding (Isolator) in 1 page [retrieved on Jan. 6, 2015; Publication Date Unknown]; accessed on the world wide web at http://www.healthmark.ca/2-36-10-ChemoSphere_en.html?ProductID=244.
Healthmark, "Hospital Medication Preparation, Packaging and Dispensing," Oncology Preparation and Administration in 1 page [retrieved on Jan. 6, 2015; Publication Date Unknown]; accessed on the world wide web at http://www.healthmark.ca/2-36-10-COMPANY-PROFILEHospital-en.html.
Healthmark, "Hospital Medication Preparation, Packaging and Dispensing, "Phocus—RX (Camera Verification System), Remote Rx Checking of admixtures in 2 pages [retrieved on Jan. 6, 2015; Publication Date Unknown]; accessed on the world wide web at http://www.healthmark.ca/2-36-10-PHOCUS-Rx-Camera-Verification-System-_en.html?ProductID=229.
Healthmark, "New Product Items" in 1 page [retrieved on Jan. 6, 2015; Publication Date Unknown]; accessed on the world wide web at http://www.healthmark.ca/home.html.
Healthmark, "Introducing the Precifill Dispensing Pump" product brochure in 2 pages [Publication Date Unknown].
Integra Brochure, from Eurospital, Brochure acquired in Mar. 2012.
International Invitation to Pay Additional Fees (with cited art), re PCT Application No. PCT/US 17/43761, mailed Sep. 21, 2017.
International Preliminary Report on Patentability, re PCT Application No. PCT/US 17/43761, issued Jan. 29, 2019.
International Search Report and Written Opinion, re PCT Application No. PCT/US 17/43761, mailed Nov. 17, 2017.
ISO/Tech Design, QC, Canada, "Chemosphere," product brochure, in 2 pages [Publication Date Unknown].
Neo Care Medical Products: Product Catalog, dated Jun. 2008, in 38 pages.
Pinnacle TPN Management System, from B Braun, downloaded May 5, 2009 from http://www.bbraunusa.com/index.cfm?uuid=7386ADF065B05CD0D22AF700339AA4092, 1 page.
"Precifill," Trademark search (TESS) in 1 page, [retrieved on Jan. 6, 2015; Application Filing Date of Sep. 30, 2011]; accessed on the world wide web at http://tmsearch.uspto.gov/bin/showfield?f=doc&state=4807:gz67gx.3.1.
Product detail for "NAMIC® Closed Fluid Systems" from Navilyst Medical, downloaded on May 11, 2010 from http://www.navilystmedical.com/Products/index.cfm/19, 2 pages.
Product detail for "RapidFill™ Automated Syringe Filler," from Baxa, downloaded on Mar. 31, 2010 from http://www.baxa.com/PharmacyProducts/AutomatedFillingSystems/ProductDetail/?id=B1, 2 pages.
Product detail for "Summit Medical DirectFlow" micro infusion extension set from Summit Medical Technologies, downloaded on May 10, 2010 from http://summitmedtech.com/p6line.php, 1 page.
Riva, downloaded in Apr. 2009 from http://www.rivasystem.com, 6 pages.
SmartSite Safety Disposables, with copyright notice dated 2004.
Smith, "Lifesaving Cancer Drugs May Put Workers' Lives at Risk," downloaded on Jul. 12, 2010 from http://www.msnbc.msn.com/id/38114586/ns/health-cancer, 7 pages.
Spiros—Closed Male Connector, published Jan. 22, 2008.
Technical Data sheet for Analog Amplifiers Type VA, models V8-C and V8-D, STM Sensors dated Dec. 2007, 4 pages.
Technical Data sheet for Through Beam Sensors Type G2, 1480 nm, STM Sensors dated Dec. 2009, 2 pages.
Technical Data sheet for Through Beam Sensors Type G2, 645 nm, STM Sensors dated Sep. 2008, 2 pages.
User Guide for medOC 1xx Basic, Neo Care Medical Products GmbH, Version Jun. 2008, 23 pages.
User Manual for medOC 3xx /6xx /8xx, Neo Care Medical Products GmbH, Version May 2008, 44 pages.

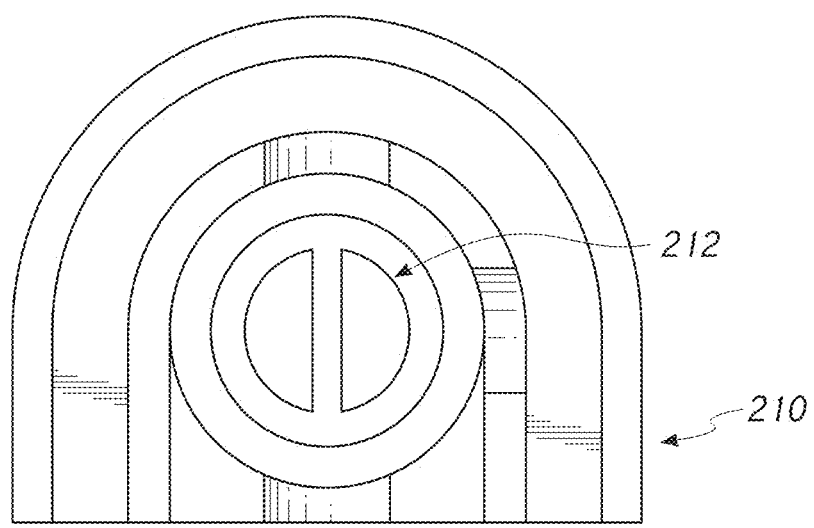
FIG. 2D_i

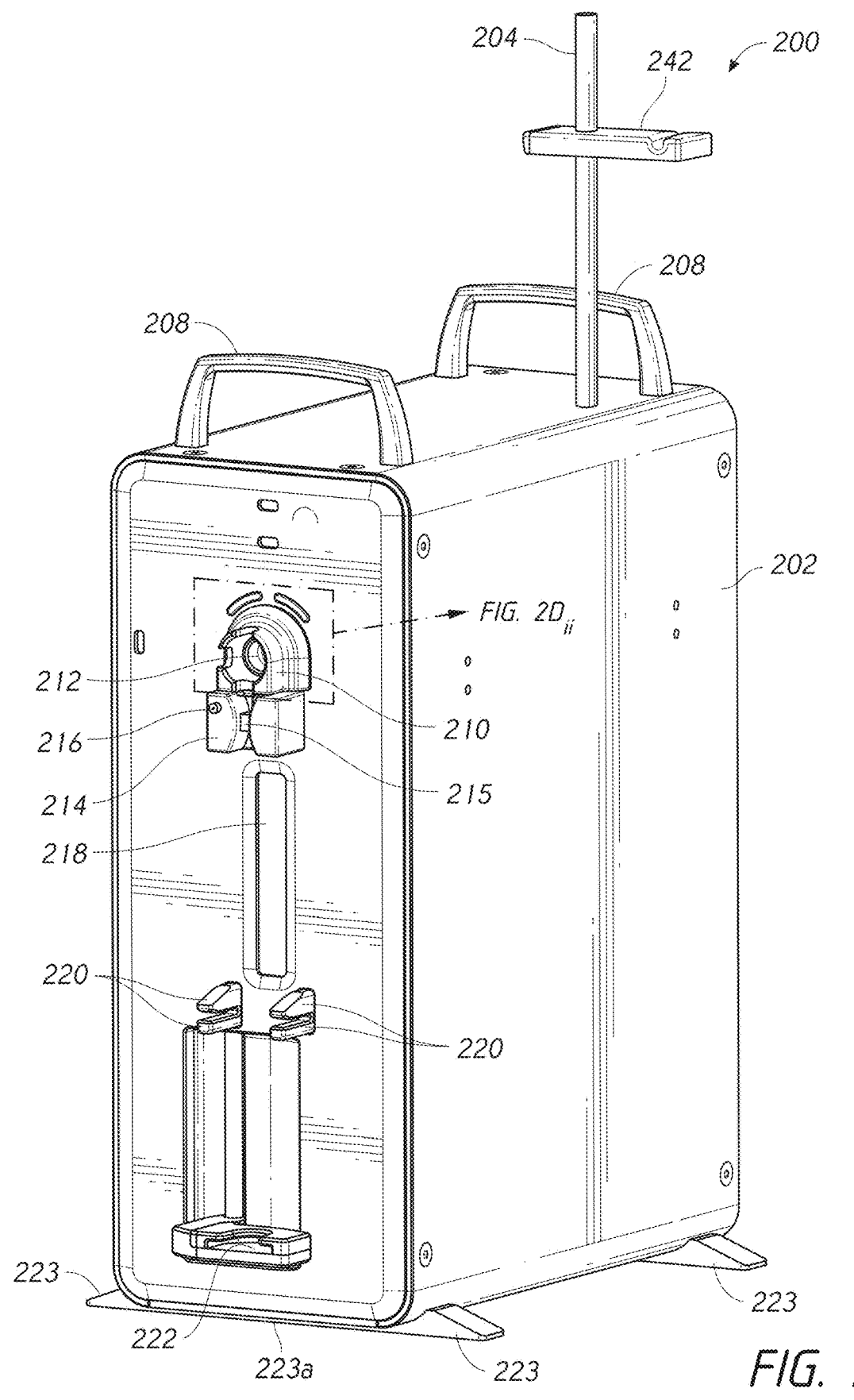
FIG. 2A_ii

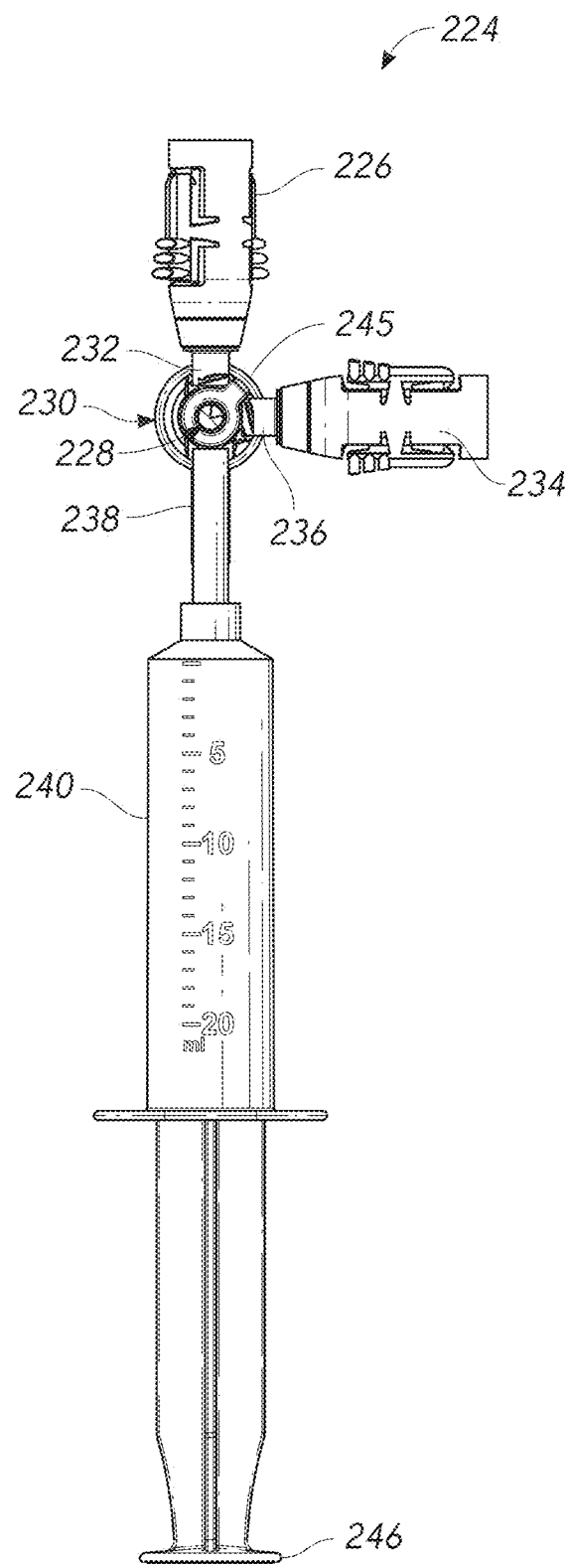
FIG. 2B ii

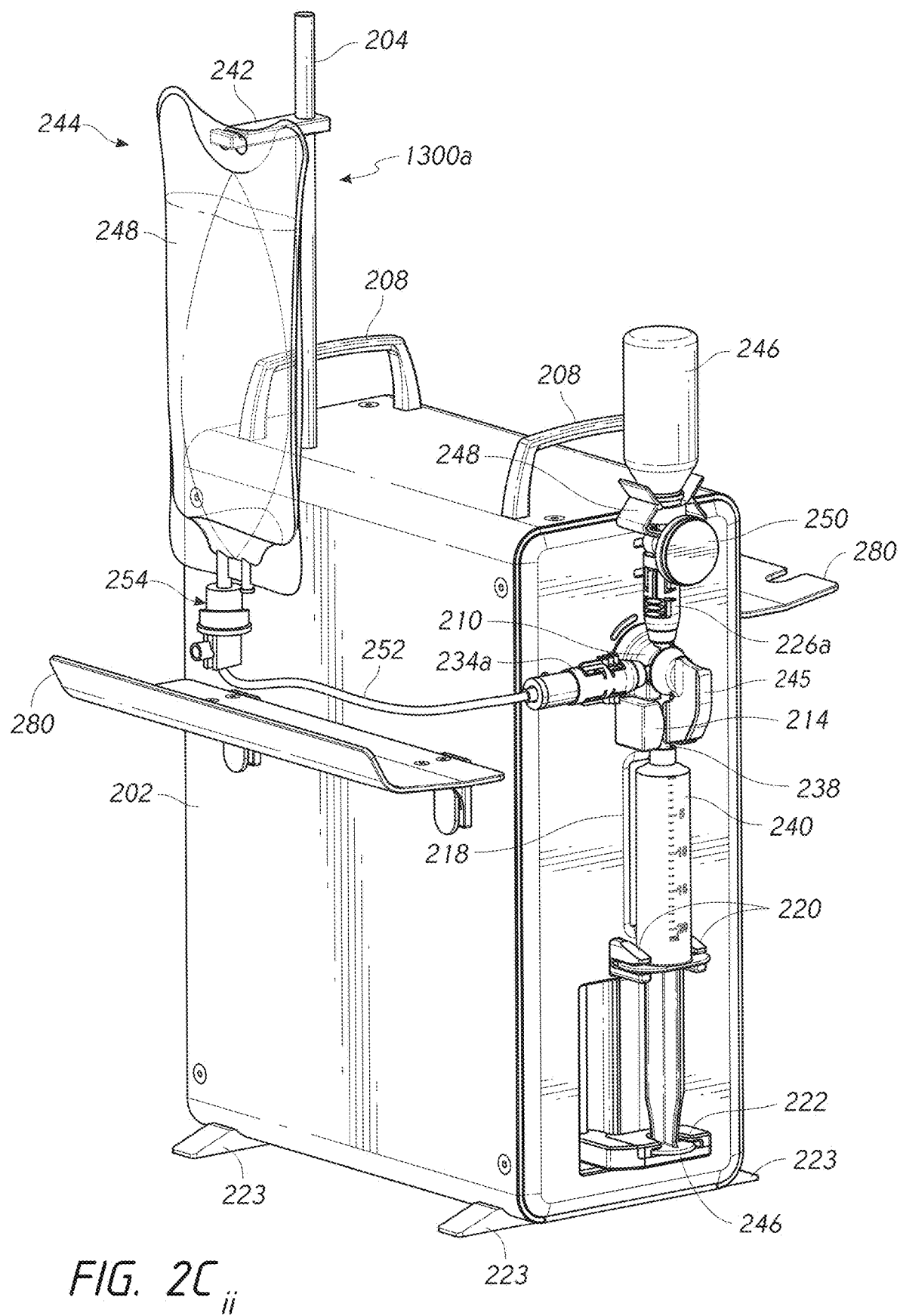
FIG. 2C ii

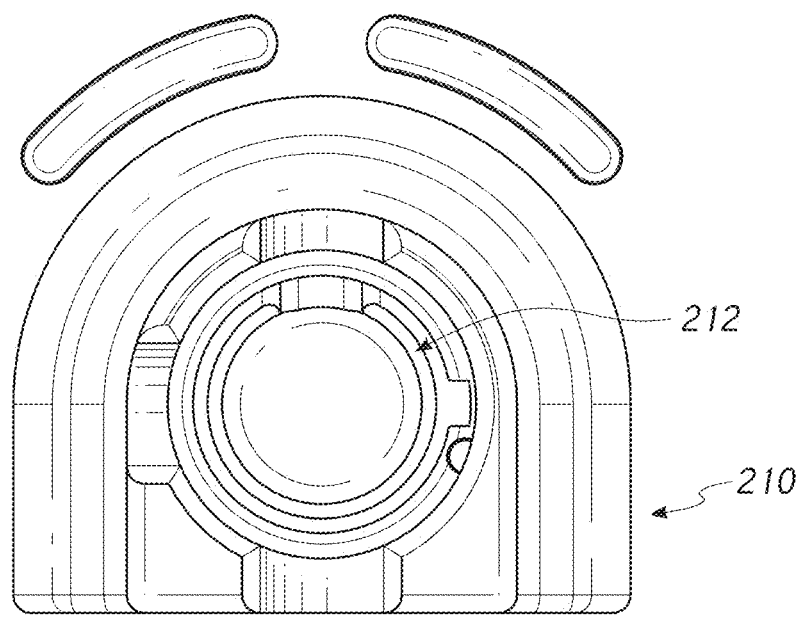
FIG. 2D$_{ii}$

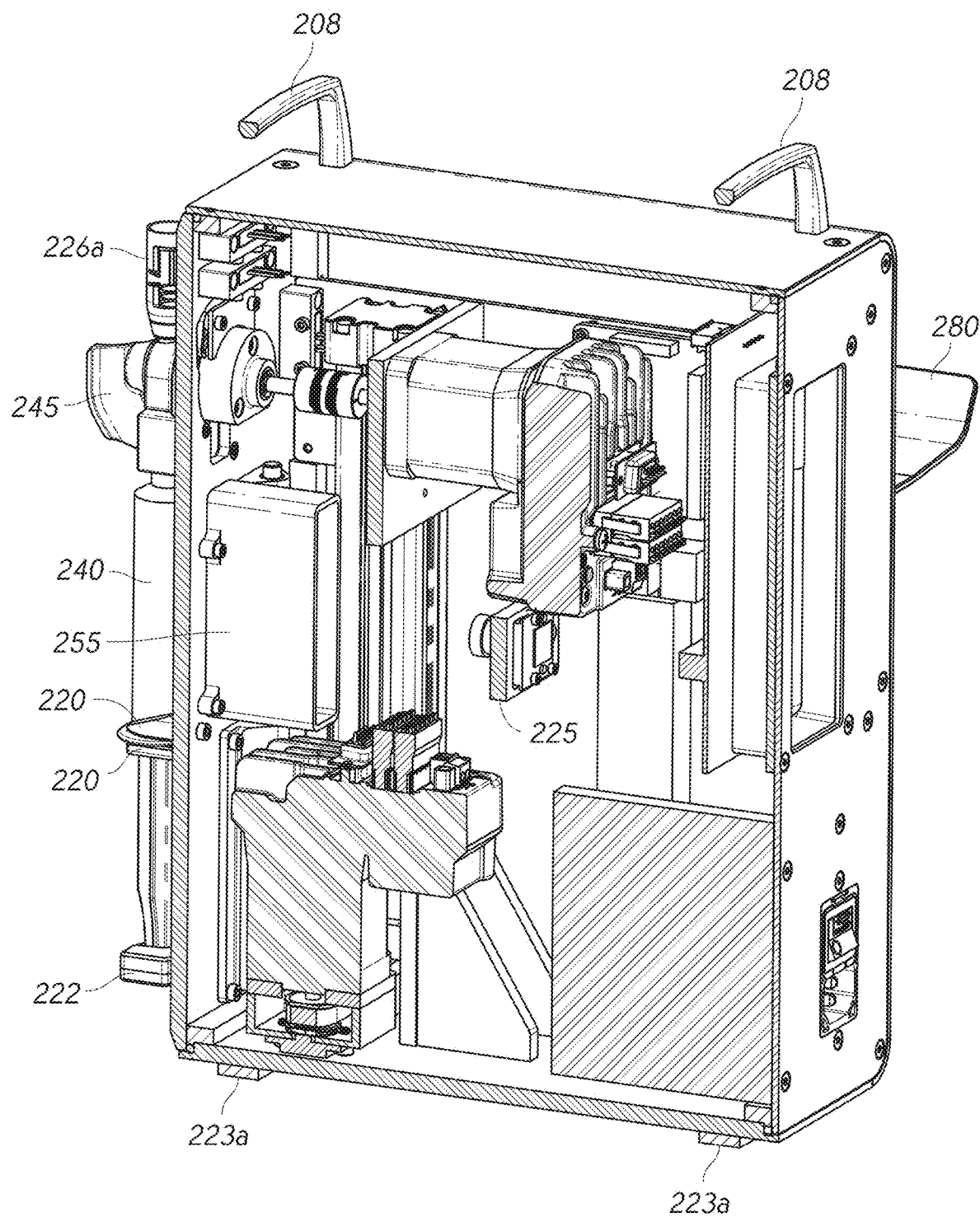
FIG. 2E_ii

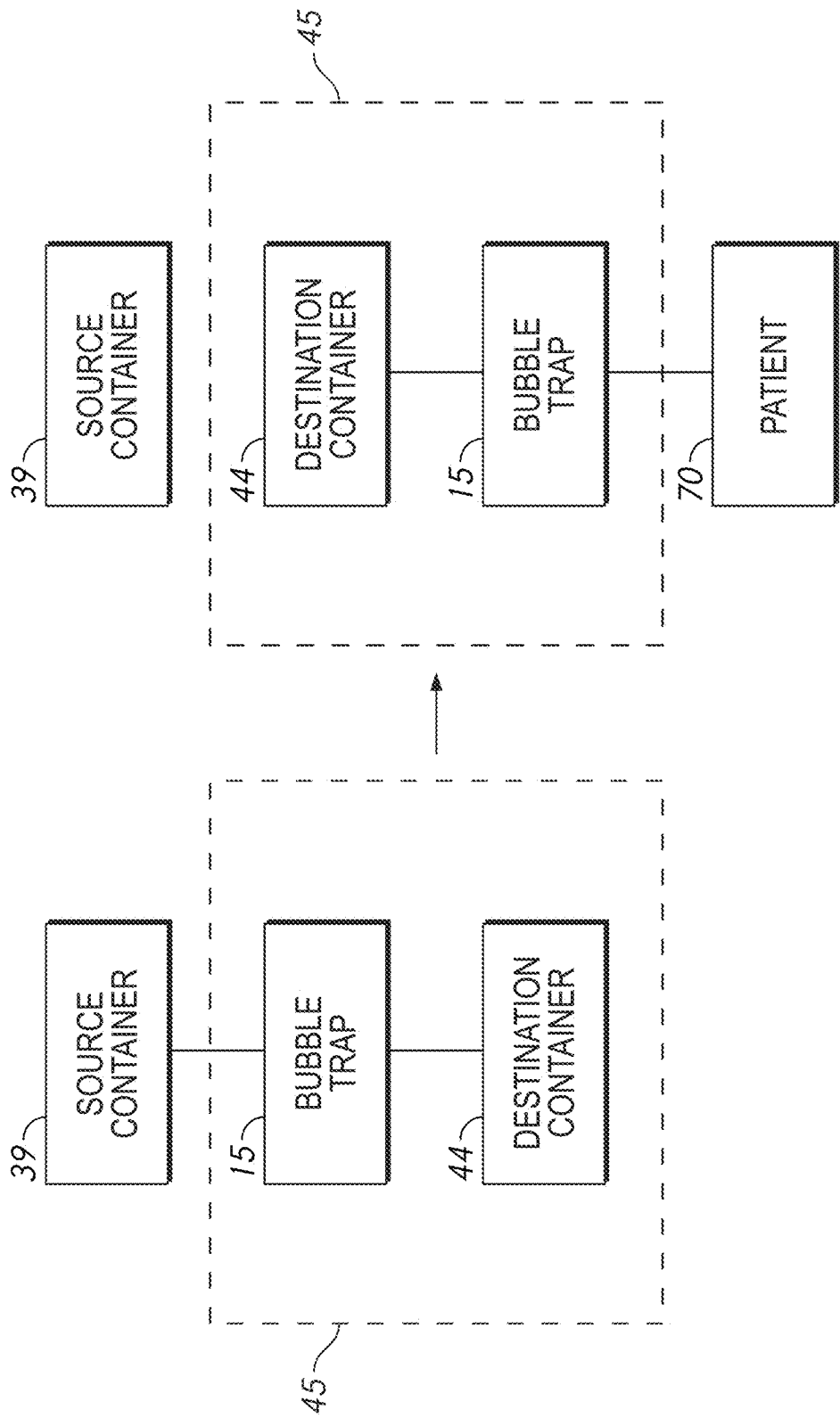

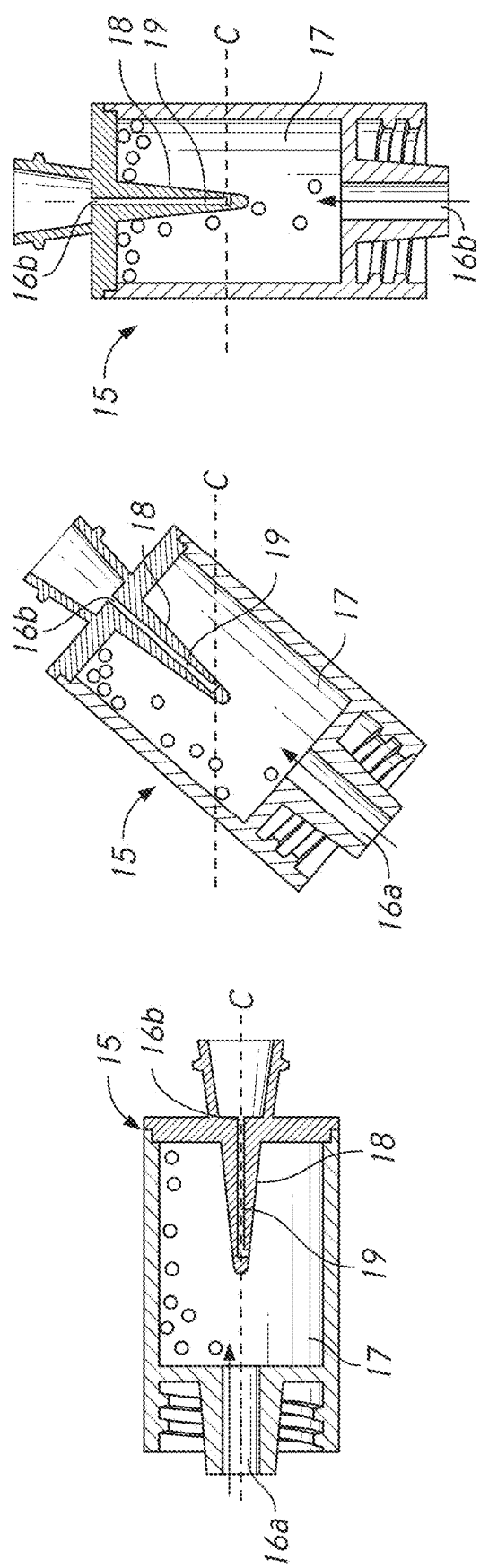
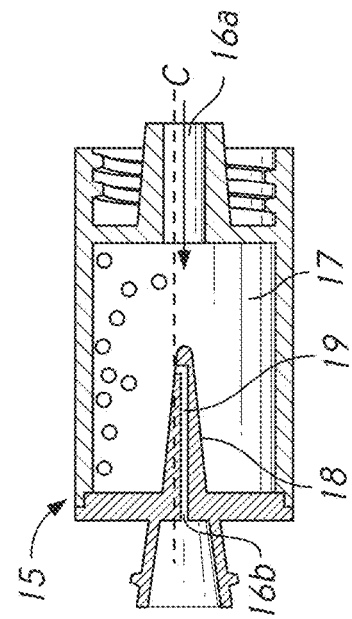
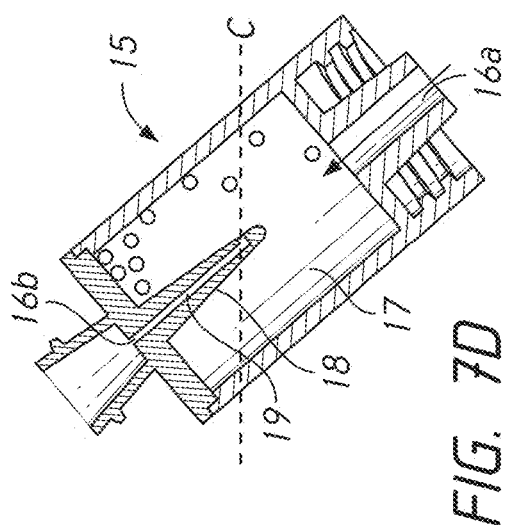
FIG. 7A  FIG. 7B  FIG. 7C  FIG. 7D  FIG. 7E

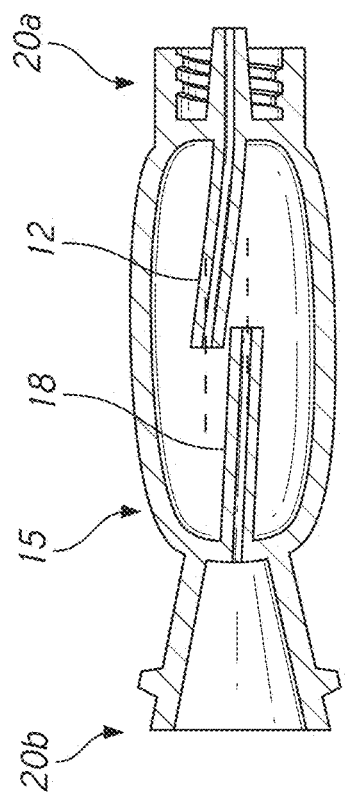
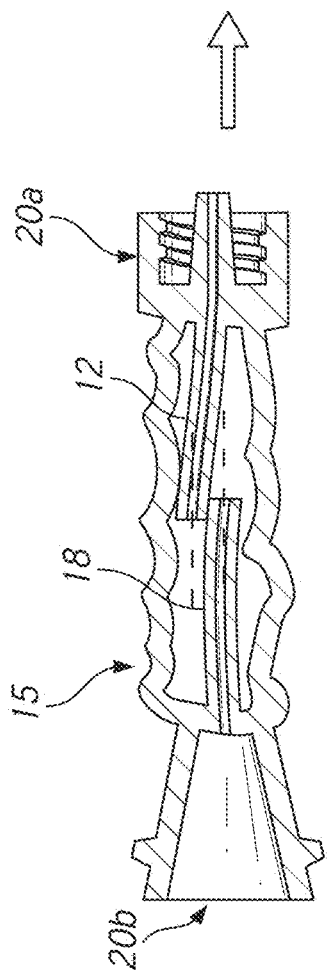
FIG. 8A
FIG. 8B

SYSTEMS, METHODS, AND COMPONENTS FOR TRAPPING AIR BUBBLES IN MEDICAL FLUID TRANSFER MODULES AND SYSTEMS

CROSS-REFERENCE TO RELATED APPLICATIONS

This application is a continuation of U.S. patent application Ser. No. 18/170,838, filed on Feb. 17, 2023, pending, which is a continuation of U.S. patent application Ser. No. 17/240,021, filed on Apr. 26, 2021, and issued as U.S. Pat. No. 11,583,637 on Feb. 21, 2023, which is a continuation of U.S. patent application Ser. No. 16/255,710, filed on Jan. 23, 2019, and issued as U.S. Pat. No. 11,020,541 on Jun. 1, 2021, which claims the benefit under 35 U.S.C. § 120 and 35 U.S.C. § 365 (c) as a continuation of International Application No. PCT/US2017/043761, designating the United States, with an international filing date of Jul. 25, 2017, entitled "SYSTEMS, METHODS, AND COMPONENTS FOR TRAPPING AIR BUBBLES IN MEDICAL FLUID TRANSFER MODULES AND SYSTEMS," which claims priority to U.S. Application No. 62/366,509, filed Jul. 25, 2016, titled "SYSTEMS, METHODS, AND COMPONENTS FOR TRAPPING AIR BUBBLES IN MEDICAL FLUID TRANSFER MODULES AND SYSTEMS," the entire contents of each of which are incorporated by reference herein and made a part of this specification.

BACKGROUND

Field

This invention relates to controlling the transfer of medical fluids and, more particularly, to limiting the transmission of gas bubbles within the medical fluids.

Description of the Related Art

Many types of medical fluids are routinely used to treat patients, including chemotherapy drugs, antibiotics, immunosuppressive drugs, antiviral drugs, hydrating fluids, nourishing fluids, anticoagulants, pain management drugs, contrast fluids for medical imaging, etc. All of these fluids, in turn, come in many different varieties with advantages and disadvantages for various types of diseases, conditions, injuries, or therapies. Moreover, particular patients require optimized dosages, concentrations, and combinations of these drugs or other medical fluids to address their specific medical needs. As a result, medical facilities are required to provide many different types of customized medical fluids on a continual basis to meet individual patient needs. In meeting these needs, a small amount of air is often present in the medical fluids that are prepared.

Systems and methods disclosed herein address various challenges related to medical fluid transfer systems and the presence of air in medical fluids.

SUMMARY

In some embodiments, a bubble trap for use in a medical fluid line is disclosed.

In some embodiments, a medical fluid bubble trap system is disclosed. The system can include a bubble trap configured to be in fluid communication with at least one of a source container and a destination container. The bubble trap can be configured to trap gas that flows into the bubble trap.

In some embodiments, a medical fluid bubble trap system is disclosed. The system can include a source container and a fluid transfer module comprising a bubble trap and a destination container. The bubble trap can be configured to trap gas that flows into the bubble trap.

In some embodiments, a medical fluid transfer module comprising a bubble trap configured to trap gas in a chamber is disclosed.

In some embodiments, an electronic medical fluid transfer device comprising a bubble trap configured to trap gas in a chamber is disclosed.

In some embodiments, an inline bubble trap device is configured to be in fluid communication with a medical fluid line to inhibit a flow of gas from an inlet to an outlet. The bubble trap device can comprise an inlet comprising an inlet opening having an inlet opening center axis, an outlet comprising an outlet opening having an outlet opening center axis, and a chamber. The inlet opening center axis and the outlet opening center axis can be different from one another such that the inlet opening is misaligned from the outlet opening. In some embodiments, the misalignment of the inlet opening from the outlet opening breaks up a fluid path from the inlet opening to the outlet opening. The chamber can be configured to trap gas that flows into the bubble trap. The chamber can be located between the inlet and the outlet.

In some embodiments, an outlet can comprise an outlet projection. The outlet projection can comprise an outlet opening and a channel in fluid communication with the outlet. The outlet projection can extend into the chamber away from an inner surface of the chamber. The outlet opening of the outlet projection can be positioned near or at the center of the chamber. The outlet opening of the outlet projection can be positioned on a side of the outlet projection.

In some embodiments, an inlet comprises an inlet projection. The inlet projection can comprise an inlet opening and a channel in fluid communication with the inlet. The inlet projection can extend into the chamber away from an inner surface of the chamber. The inlet opening can be positioned near or at the center of the chamber. The inlet opening can be positioned on a side of the inlet projection.

In some embodiments, an inlet projection and an outlet projection can extend past each other such that inlet opening is positioned closer to an outlet than the outlet opening.

In some embodiments, every flow path from an inlet opening to an outlet opening includes a bend. An inlet and an outlet can be on opposite ends of a chamber.

In some embodiments, a bubble trap can include a resilient housing at least partially defining a chamber with a rest volume. The housing can be configured to at least partially collapse when subjected to a vacuum so as to reduce the volume of the chamber and configured to return to the rest volume when the vacuum is removed.

In some embodiments, a medical fluid transfer system is configured to trap air during the transfer of medical fluids. The medical fluid transfer system can comprise a fluid transfer device configured to transfer fluid from a fluid source to a fluid destination and an inline bubble trap, as described herein. The inline bubble trap can comprise a female luer end and a male luer end. The bubble trap can be configured to be in fluid communication with at least one of the fluid transfer device, a fluid source, and a fluid destination. The bubble trap can be configured to inhibit a transfer of gas from the fluid source, through the outlet of the bubble trap, and into the fluid destination. The bubble trap can be in fluid communication with the fluid source. The bubble trap can be in fluid communication with the fluid destination. The female luer end can be adjacent to the outlet. The male luer end can be adjacent to the inlet.

In some embodiments, a method of transferring fluids from a source container to a destination container can comprise the step of obtaining a fluid transfer module configured to inhibit a transfer of gas from the source container to the destination container. The fluid transfer module can comprise an inline bubble trap. The bubble trap can comprise a chamber, an inlet opening having an inlet center axis, and an outlet opening having an outlet center axis different from the inlet center axis such that the inlet opening is misaligned from the outlet opening. The method of transferring fluids can further comprise the steps of ensuring the fluid transfer module is in fluid communication with the source container and the destination container and transferring fluid from the source container, through the fluid transfer module, and into the destination container. The method can further comprise the step of initiating a vacuum in the destination container and the fluid transfer module such that a volume defined by the chamber of the fluid transfer module is reduced prior to initiating the transferring step. The inlet opening being misaligned from the outlet opening can break up a fluid path from the inlet opening to the outlet opening. The fluid transfer module can further comprise an outlet projection having the outlet opening and a channel in fluid communication with the outlet. The outlet projection can extend into the chamber away from an inner surface of the chamber. The outlet opening of the outlet projection can be positioned on a side of the outlet projection. The fluid transfer module can further comprise an inlet projection having the inlet opening and a channel in fluid communication with the inlet. The inlet projection can extend into the chamber away from an inner surface of the chamber. The inlet opening can be positioned on a side of the inlet projection. The method can further comprise disconnecting the fluid transfer module from the source container and the destination container.

In some embodiments, an inline bubble trap device is configured to be in fluid communication with a medical fluid line to inhibit a flow of gas from an inlet to an outlet. The bubble trap device can comprise a chamber comprising an inner surface and an outer surface, an inlet comprising an inlet projection extending into the chamber, the inlet projection having an inlet channel and an inlet opening being displaced away from the inner surface of the chamber, an outlet comprising an outlet projection extending into the chamber, the outlet projection having an outlet channel and an outlet opening being displaced away from the inner surface of the chamber. The inlet opening and the outlet opening can be oriented away from each other such that fluid moving between the openings need take an indirect path. At least one of the inlet and the outlet channels can comprise a curve that misaligns the inlet opening from the outlet opening and breaks up a fluid path from the inlet opening to the outlet opening through the chamber. The chamber can be configured to trap gas that flows into the bubble trap. The chamber can be collapsible. The outlet opening of the outlet projection can be positioned near or at the center of the chamber. The inlet opening can be positioned near or at the center of the chamber. The inlet projection and the outlet projection can project past each other within the chamber.

In some embodiments, a patient source bag is for use with a medical fluid infusion pump. The patient source bag can comprise a chamber, an outlet comprising an outlet region in fluid communication with the chamber, and a barrier defining an air collection region in fluid communication with the outlet. The barrier can be configured to maintain air within the air collection region. The barrier can be configured inhibit the transfer of gas through the outlet region. The air collection region can be located outside a continuous fluid flow path between the chamber and the outlet region. The air collection region can be spaced apart from the outlet. The outlet can be located on an upper region of the chamber. The outlet can be configured to permit the passage of fluid into and out of the chamber. The patient source bag can further comprise a port configured to permit the removal of air from the chamber. The patient source bag can further comprise at least one access port. The access port can be a closeable female luer connector. The access port can be a closeable male luer connector. The patient source bag can further comprise a bubble trap outside the chamber an in fluid communication with the chamber.

BRIEF DESCRIPTION OF THE DRAWINGS

Embodiments will now be described with reference to the following drawings, which are provided by way of example, and not limitation. Like reference numerals indicate identical or functionally similar elements.

FIG. $2A_i$ is a front perspective view of an example of an electromechanical system for transferring medical fluid.

FIG. $2B_i$ is a rear view of an example of a fluid transfer device.

FIG. $2C_i$ is a front perspective view of the electromechanical system for transferring medical fluid of FIG. $2A_i$ with the fluid transfer device of FIG. $2B_i$ attached to it.

FIG. $2D_i$ is a magnified partial front view of the electromechanical system of FIG. $2A_i$ which illustrates an example of a driver.

FIG. $2A_{ii}$ is a front perspective view of an example of an electromechanical system for transferring medical fluid according to another embodiment.

FIG. $2B_{ii}$ is a rear view of an example of a fluid transfer device according to another embodiment.

FIG. $2C_{ii}$ is a front perspective view of the electromechanical system for transferring medical fluid of FIG. $2A_{ii}$ with the fluid transfer device of FIG. $2B_{ii}$ attached to it.

FIG. $2D_{ii}$ is a magnified partial front view of the electromechanical system of FIG. $2A_{ii}$ which illustrates an example of a driver.

FIG. $2E_{ii}$ is a rear perspective cross-sectional view of the electromechanical system and fluid transfer device shown FIG. $2C_{ii}$.

Figure 3:

FIG. 3 is a front plan view of an example of a user control device.

Figure 4:
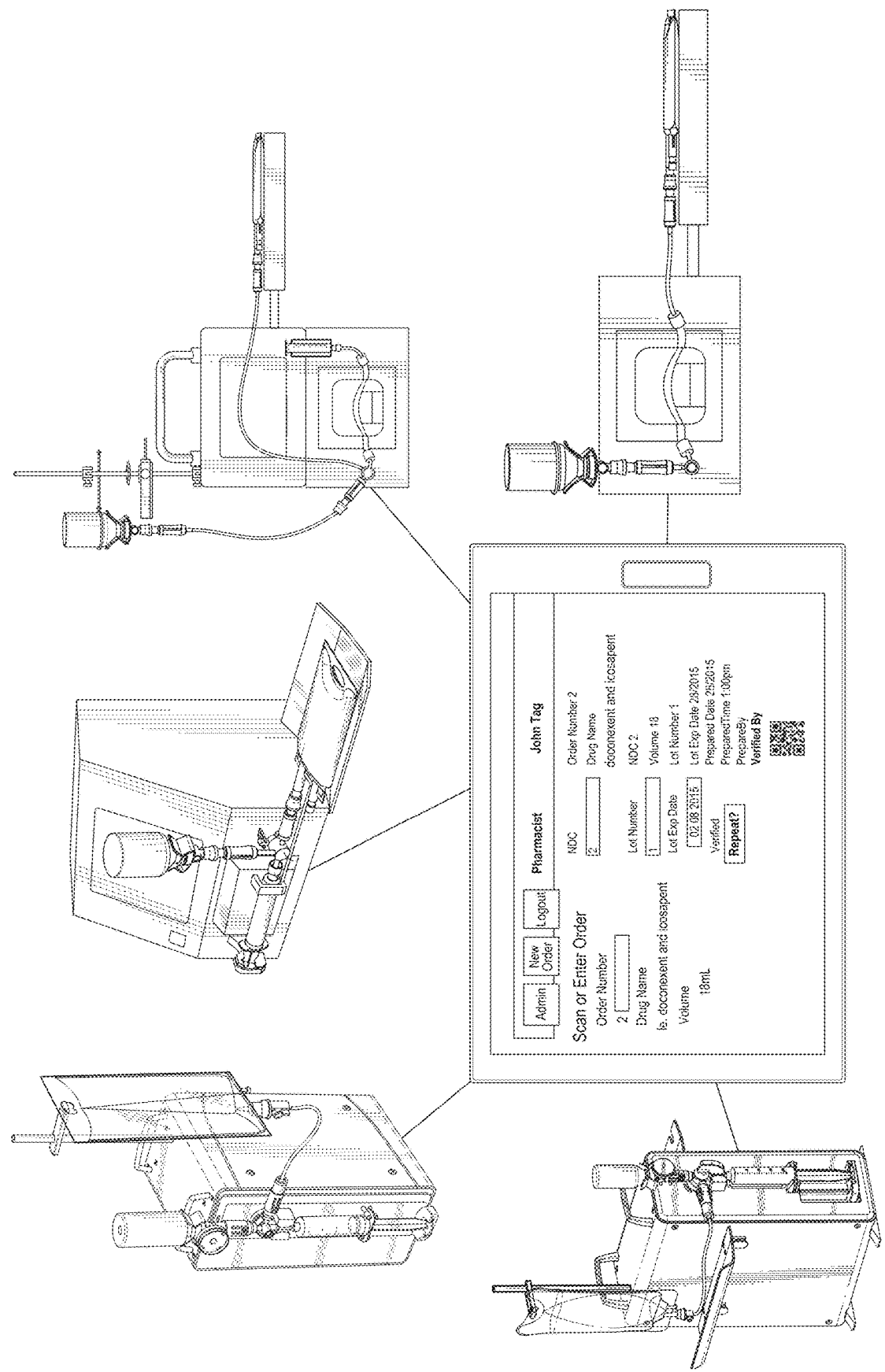

FIG. 4 is a schematic illustration of a user interface configured to electronically communicate with a plurality of different types of medical fluid transfer devices.

FIG. 5A is a schematic of a fluid transfer module having a bubble trap in fluid communication with a source container.

FIG. 5B is a schematic of the fluid transfer module of FIG. 5A disconnected from the source container and in fluid communication with a patient.

Figure 1A:
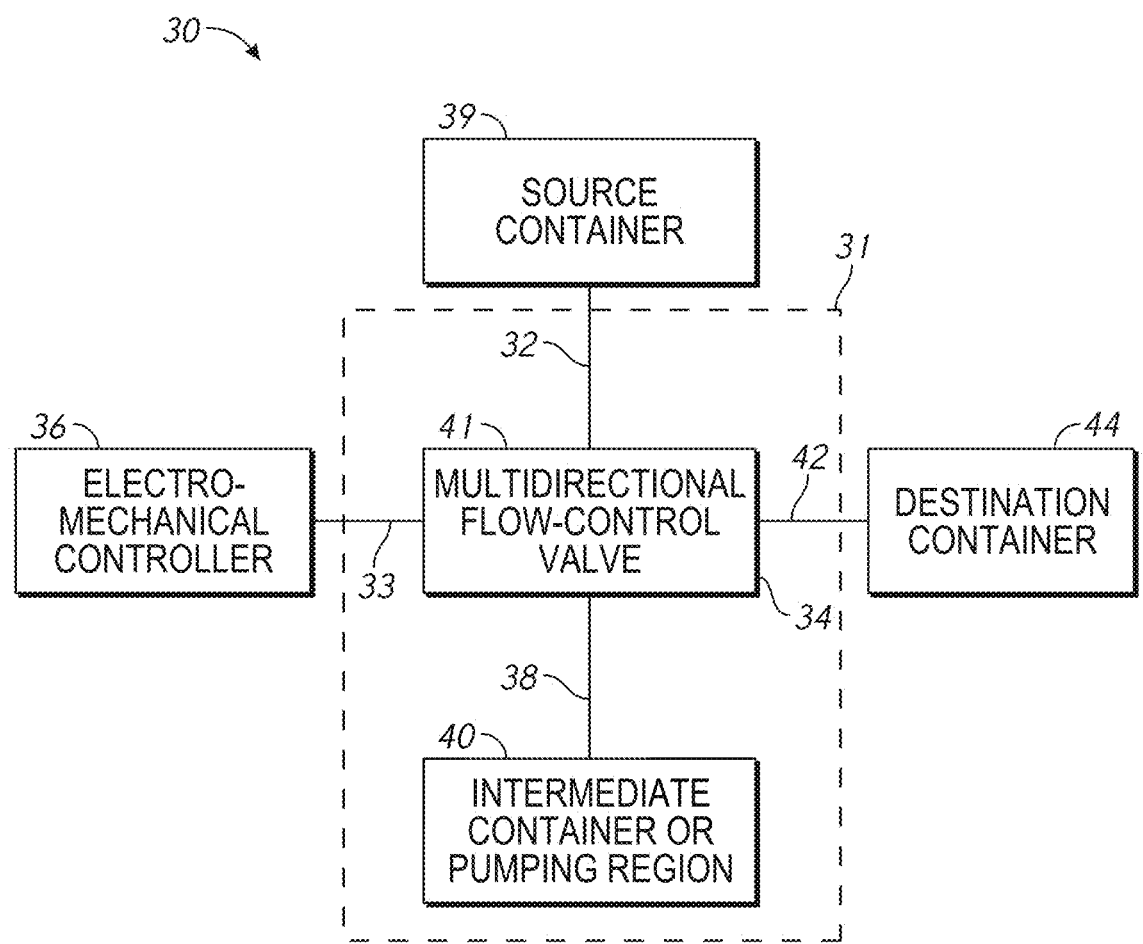
FIG. 1A is a schematic illustration of an example of a fluid transfer device removably attached to and/or in selective communication with other components of a fluid transfer system.
Figure 5C:
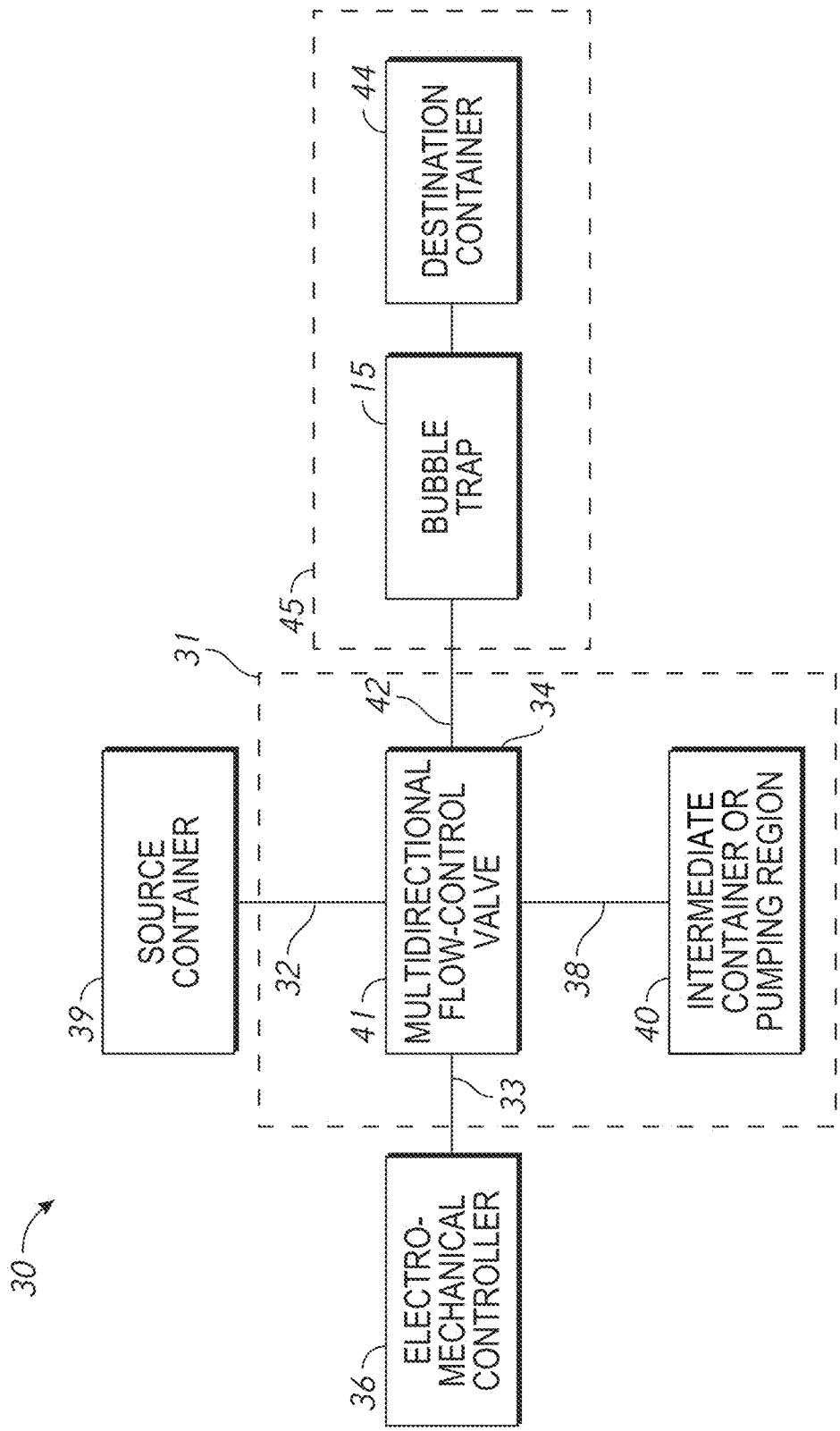

FIG. 5C is a schematic of a fluid transfer module having a bubble trap in fluid communication with the fluid transfer device of FIG. 1A.

Figure 6A:
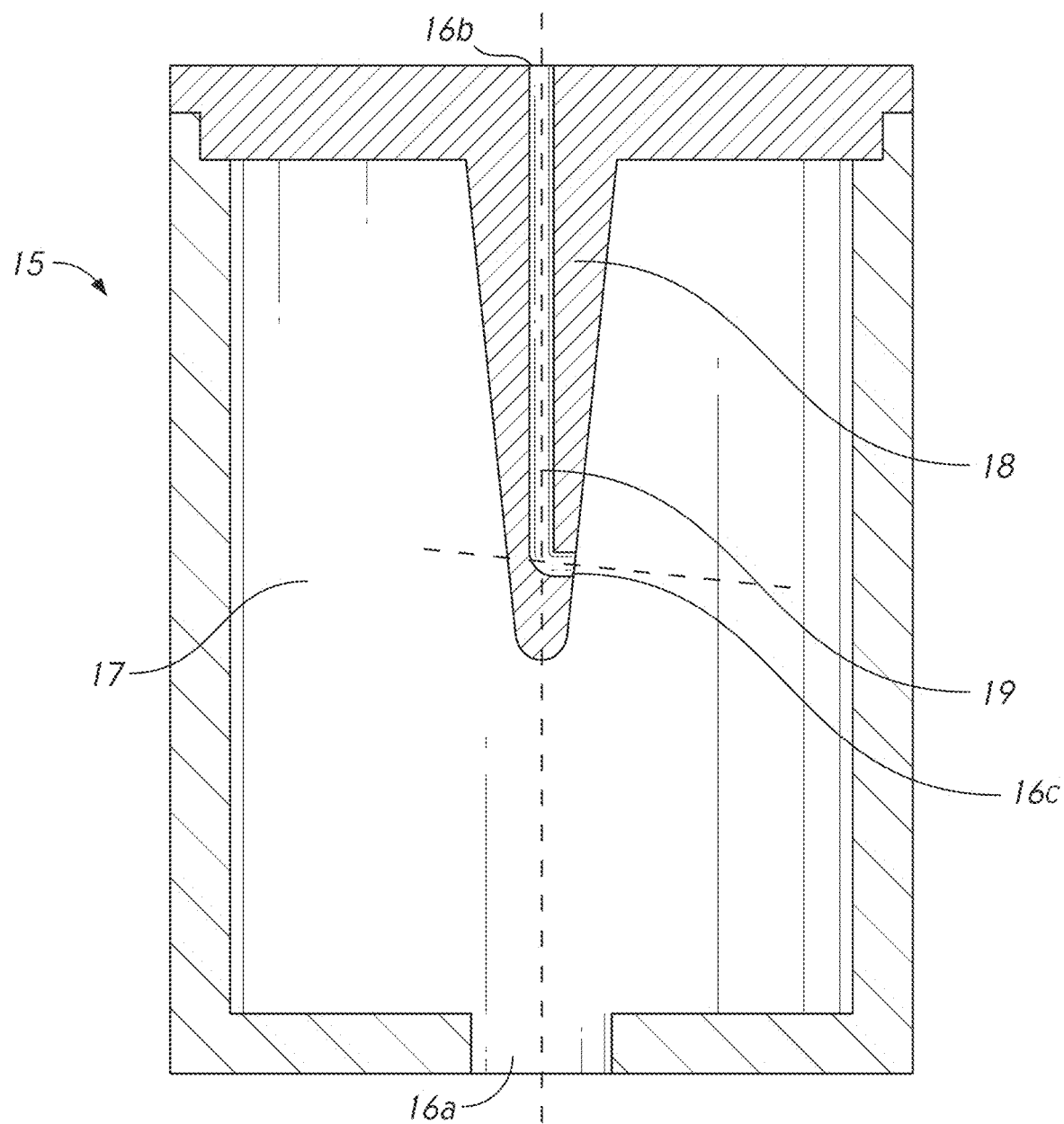
Figure 6A:
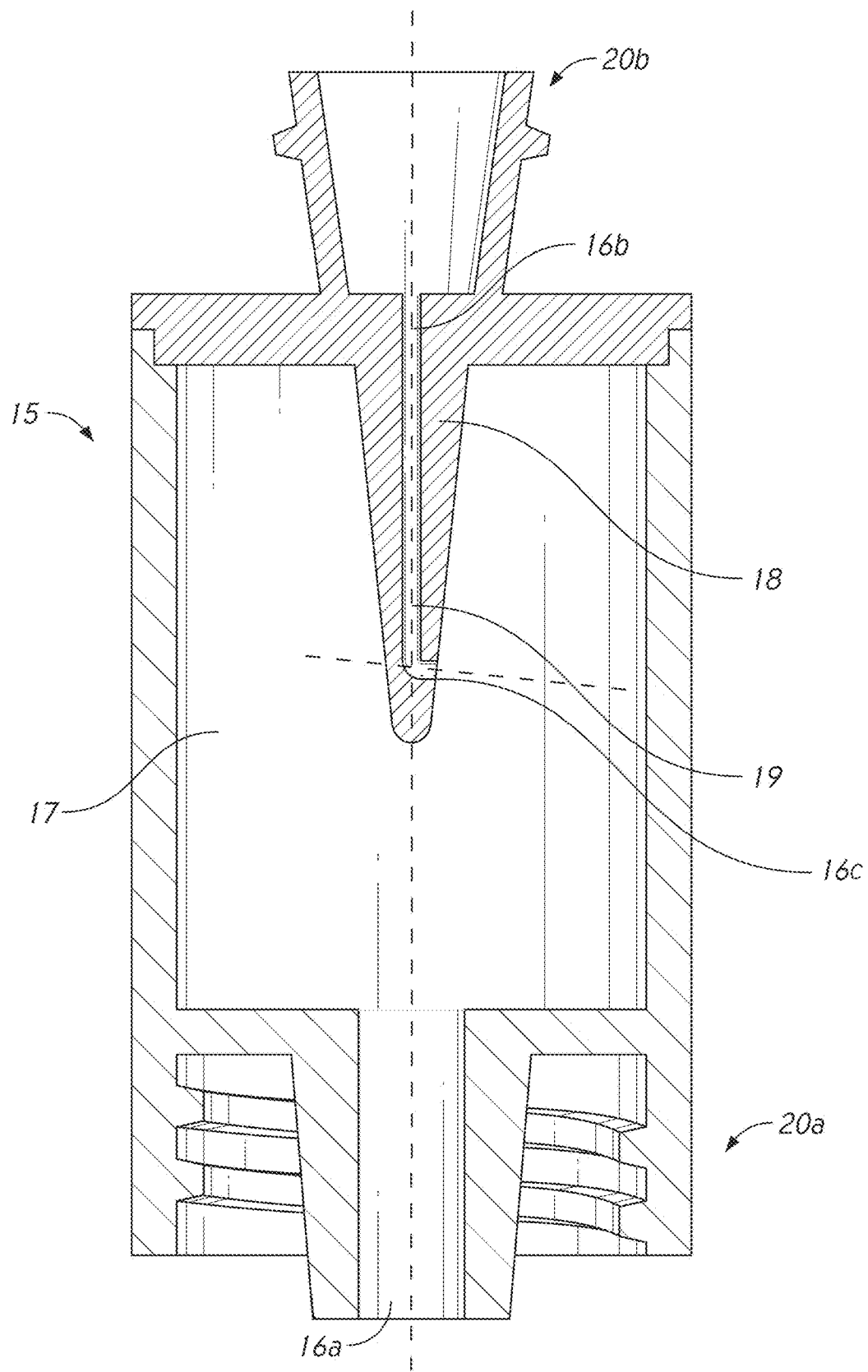

FIG. 6A is a schematic of a bubble trap, according to some embodiments.

FIG. 6A' is a schematic of the bubble trap of FIG. 6A with luer connectors.

Figure 6B:
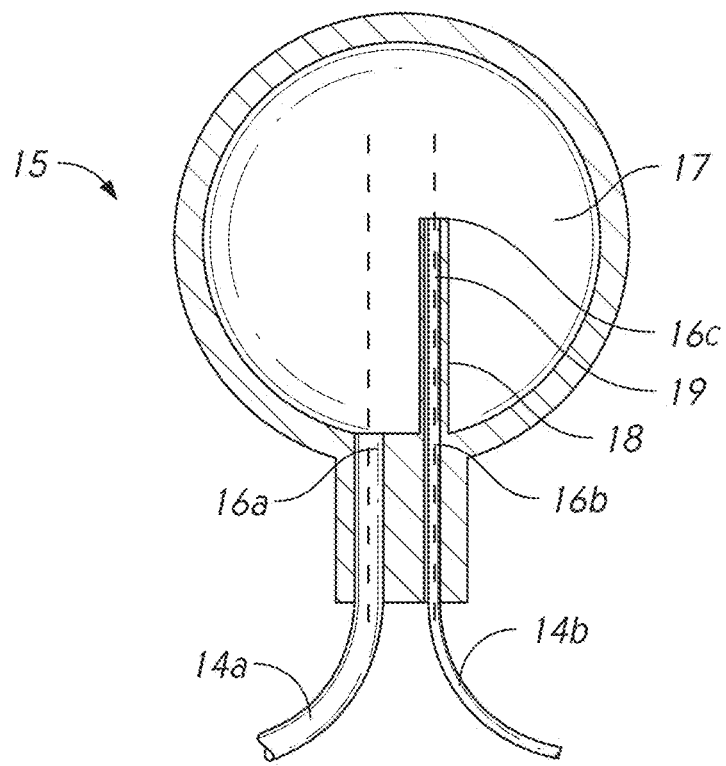

FIG. 6B is another schematic of a bubble trap, according to some embodiments.

Figure 6C:
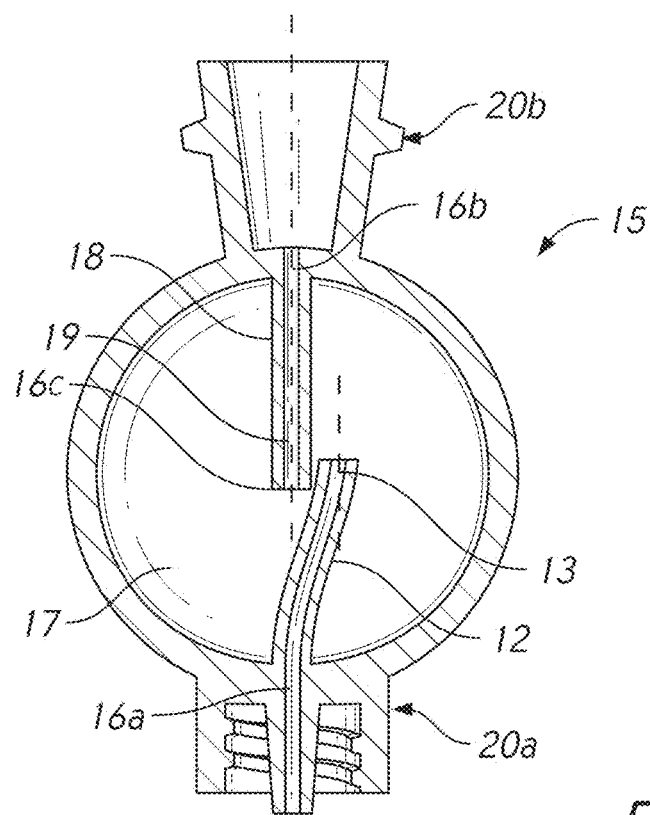

FIG. 6C is another schematic of a bubble trap, according to some embodiments.

FIG. 7A is a schematic of a bubble trap with fluid flow in a first position, according to some embodiments.

FIG. 7B is a schematic of the bubble trap of FIG. 7A rotated 45 degrees counterclockwise.

FIG. 7C is a schematic of the bubble trap of FIG. 7B rotated 45 degrees counterclockwise.

FIG. 7D is a schematic of the bubble trap of FIG. 7C rotated 45 degrees counterclockwise.

FIG. 7E is a schematic of the bubble trap of FIG. 7D rotated 45 degrees counterclockwise.

Figures 7F, 7G, 7H:
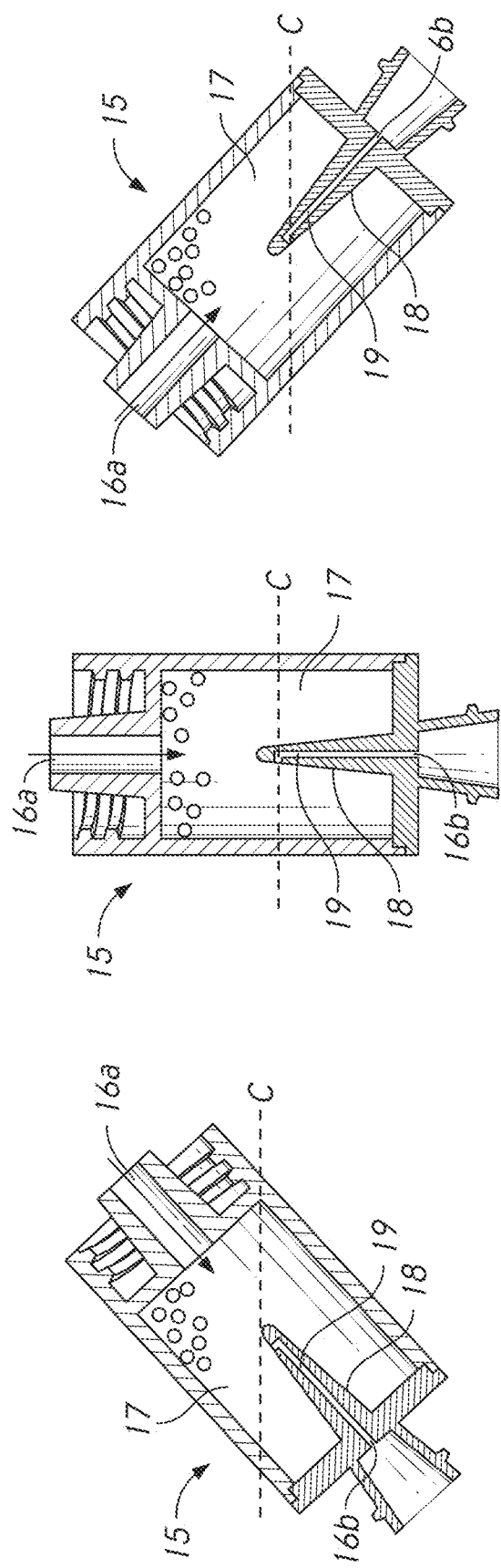

FIG. 7F is a schematic of the bubble trap of FIG. 7E rotated 45 degrees counterclockwise.

FIG. 7G is a schematic of the bubble trap of FIG. 7F rotated 45 degrees counterclockwise.

FIG. 7H is a schematic of the bubble trap of FIG. 7G rotated 45 degrees counterclockwise.

FIG. 8A is a schematic of a bubble trap with a vacuum applied, according to some embodiments.

FIG. 8B is a schematic of the bubble trap of FIG. 8A filled with fluid.

Figure 9A:
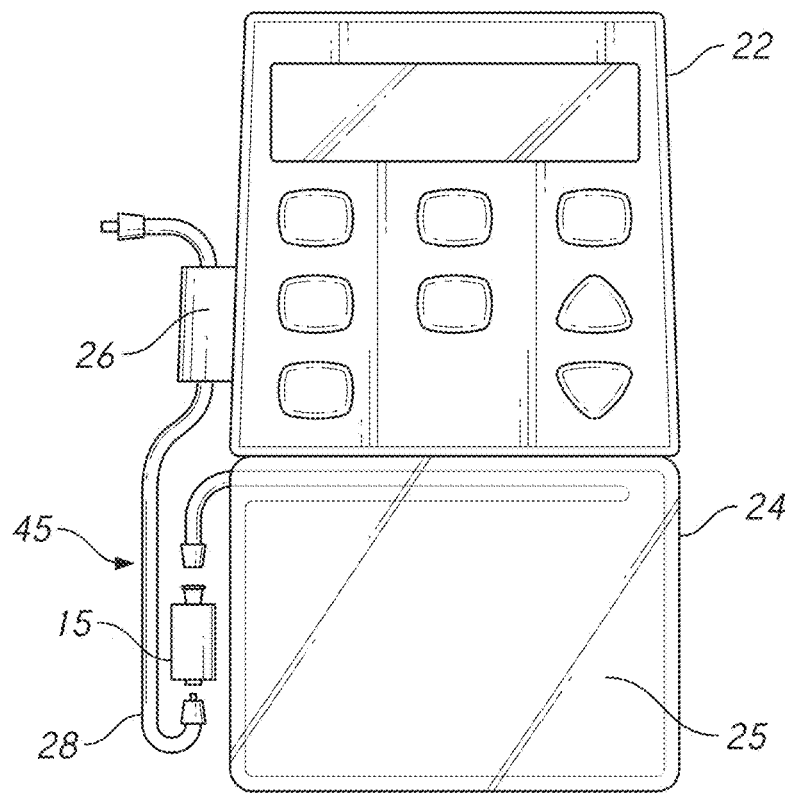

FIG. 9A is a schematic of a bubble trap attached to a cassette with a reservoir, according to some embodiments.

Figure 9B:
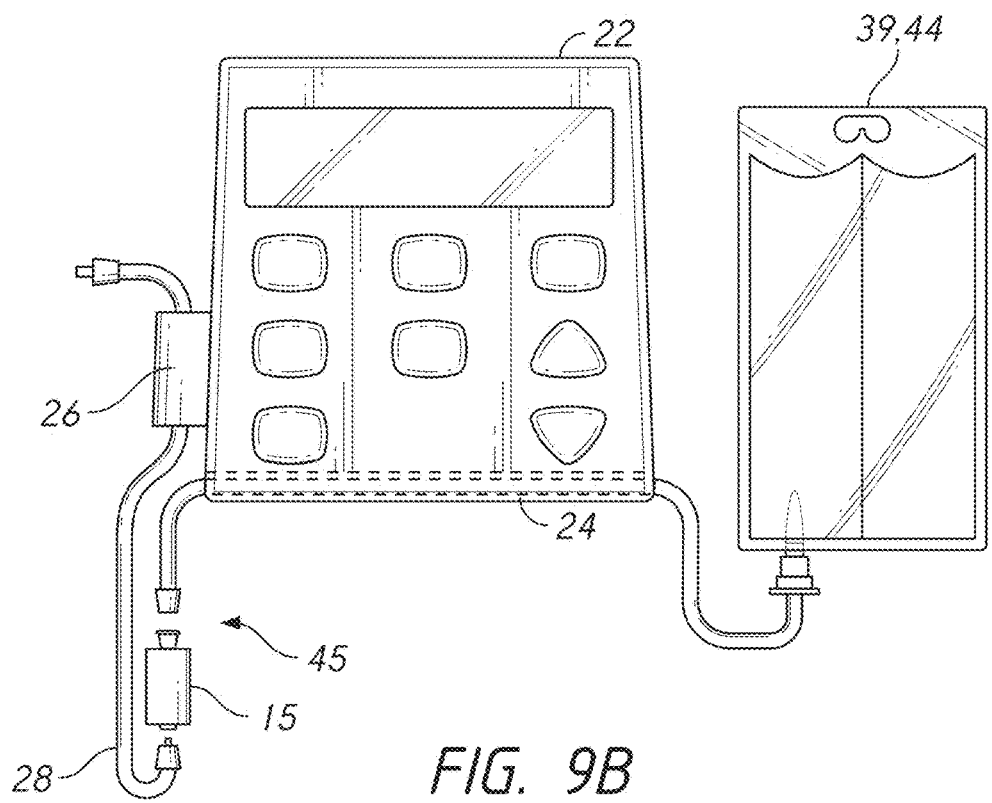

FIG. 9B is a schematic of a bubble trap attached to a cassette without a reservoir, according to some embodiments.

Figure 9C:
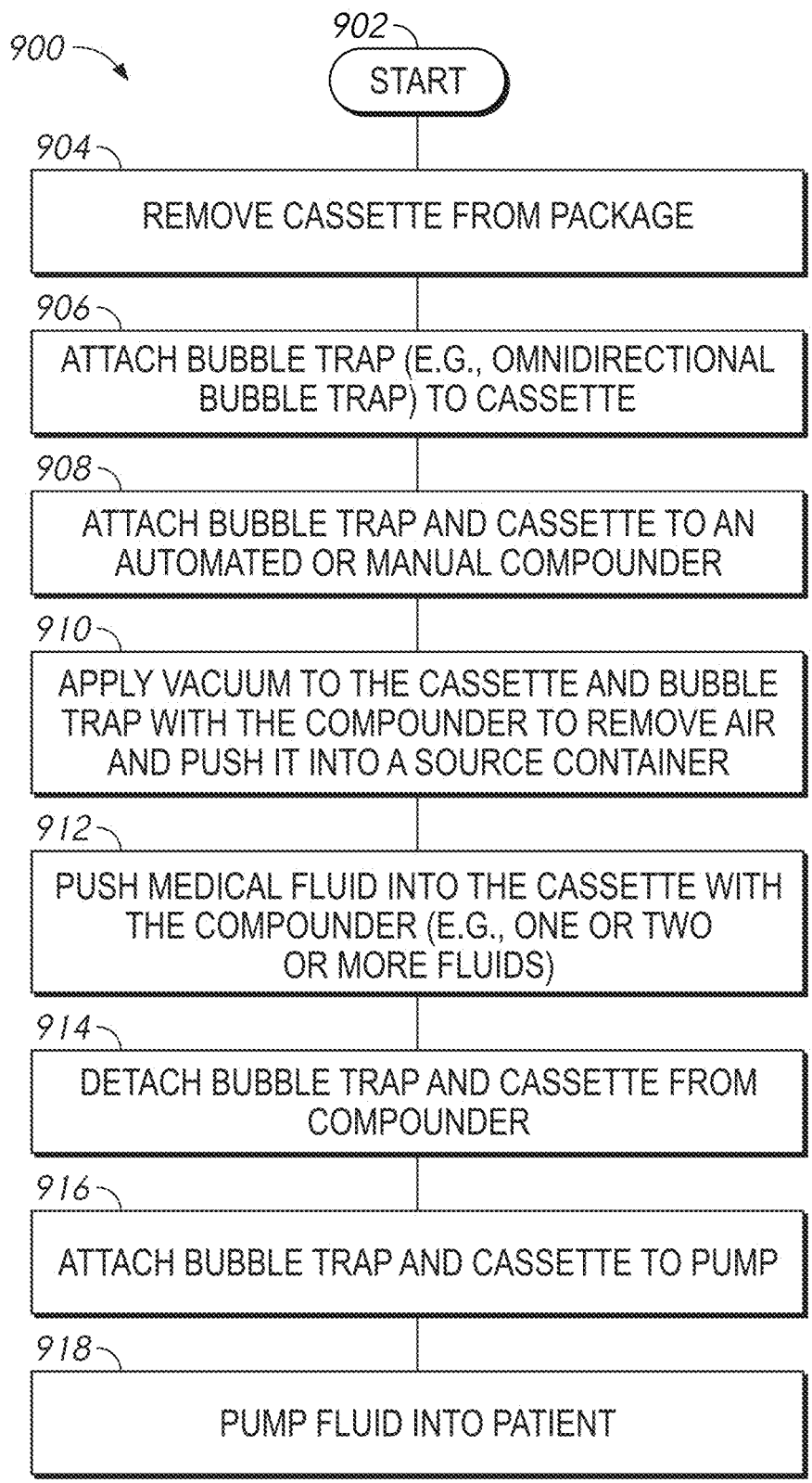

FIG. 9C is an example protocol for filling the cassette of FIG. 9A with medical fluid.

Figure 10A:
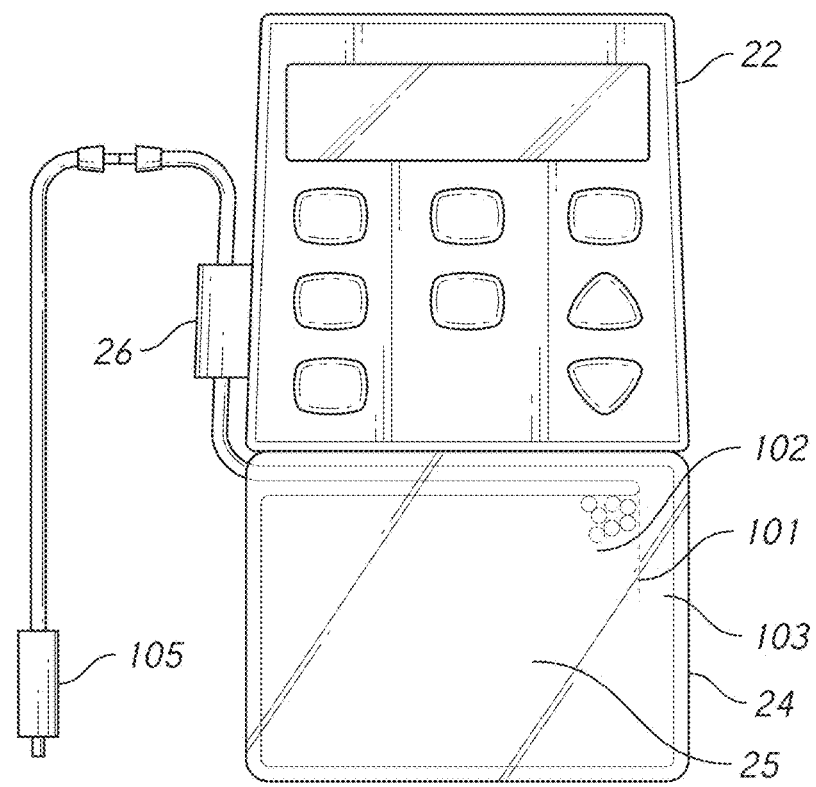

FIG. 10A is a schematic of a cassette configured to trap air, according to some embodiments.

Figure 10B:
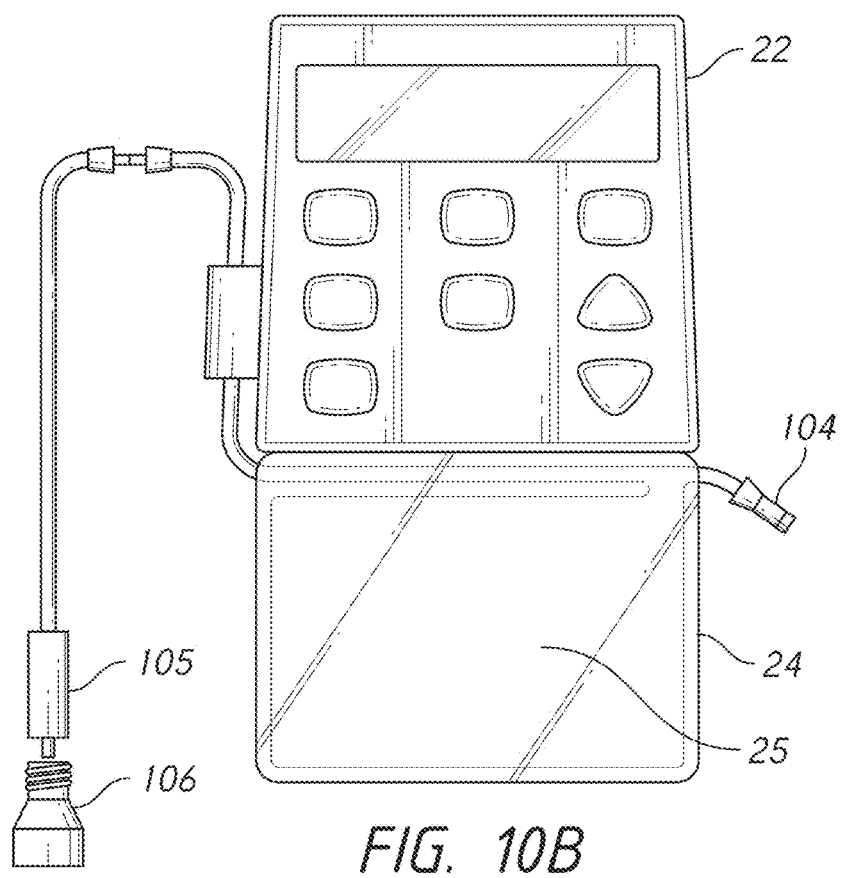

FIG. 10B is another schematic of a cassette configured to trap air, according to some embodiments.

DETAILED DESCRIPTION

Various systems, methods, and components can be used in different embodiments of the inventions. Some embodiments are illustrated in the accompanying figures; however, the figures are provided for convenience of illustration only, and should not be interpreted to limit the inventions to the particular combinations of features shown. Rather, any feature, structure, material, step, or component of any embodiment described and/or illustrated in this specification can be used by itself, or with or instead of any other feature, structure, material, step, or component of any other embodiment described and/or illustrated in this specification. Nothing in this specification is essential or indispensable.

FIG. 1A is an example of a schematic illustration of a fluid transfer device 30 removably attached to and/or in selective communication with other components of a fluid transfer system. In some embodiments, a fluid transfer device 30 can comprise a source container 39, a fluid transfer module 31, an electromechanical controller 36, and a destination container 44. The source container 39 and the fluid destination container 44 can each comprise any suitable device for holding or supplying medical fluids, such as a vial, a bottle, a bag, a hose, a tube, a tank, a canister, etc. In some embodiments, the fluid destination container 44 is a type of container that is selected to be particularly well suited in size and structure for easy and convenient storage or transportation from a fluid transfer station to a patient treatment location, such as an intravenous fluid storage bag or IV bag, to provide an individual-patient, single-dosage supply of medical fluid. In some embodiments, the source container 39 is a type of container that is sufficiently large to provide multiple single-patient doses to be transferred into multiple destination containers 44 (either serially or in parallel). Some examples of fluid transfer devices 30 are illustrated and described in U.S. Pat. No. 8,522,832; U.S. Patent Application Publication No. 2014/0299221; PCT International Application No. US2015/040174; and U.S. Patent Application Publication No. 2015/0283322, all of which are incorporated by reference in their entireties and made a part of this specification, and any feature, structure, material, step, or component of any embodiment described and/or illustrated in any of these can be used with or instead of any other feature, structure, material, step, or component of any embodiment described and/or illustrated elsewhere in this specification.

The fluid transfer module 31 can comprise a multidirectional flow-control valve 41 and an intermediate container or pumping region 40, as well as any connector(s) and/or conduit(s) that may extend between or among these or any other components of the fluid transfer module 31, and/or any connectors and/or conduits that may extend between or among the fluid transfer module 31 and the source container 39 and/or the destination container 44. For example, the fluid transfer module 31 can comprise an inlet fluid connector 32 and tubing that can be configured to removably attach the multidirectional flow-control valve to the source container 39; and/or the fluid transfer module 31 can comprise an outlet fluid connector 42 and tubing that can be configured to removably attach the multidirectional flow control valve to the destination container 44.

As shown in FIG. 1A, the fluid transfer module 31 can comprise an intermediate fluid connector 38 that fluidly connects the multidirectional flow-control valve 41 and the intermediate container or pumping region 40. In some embodiments, the intermediate fluid connector 38 is a conduit and/or a tube attached by an appropriate permanent, fluid-tight method (e.g., adhesive, bonding, ultrasonic welding, etc.) between the multidirectional flow-control valve 41 and the intermediate container or pumping region 40. The intermediate container or pumping region 40 can comprise any suitable container or region that is configured to hold and measure fluids and/or to assist in providing an impetus for fluid-flow along a fluid conveying path. For example, in some embodiments, the intermediate container or pumping region 40 can be a syringe or a region of a conduit that is configured to interface with a peristaltic pump, or any other suitable intermediate device. Not all fluid transfer modules 31 will include all of the components or features illustrated or described in this specification; rather, one or more components or features can be omitted in any suitable embodiment.

The multidirectional flow-control valve 41 can be configured to mechanically attach to or interface with the electromechanical controller 36. For example, in some embodiments, the multidirectional flow-control valve 41 can comprise a driving interface 33 that is configured to attach with and/or interface with a corresponding electromechanical driver (see, e.g., FIGS. $2A_i$, $2D_i$, $2A_{ii}$, $2D_{ii}$) of the electromechanical controller 36. The electromechanical controller 36 can actuate the multidirectional flow-control valve 41 under the control of one or more algorithms or instructions provided by a computer processor or a plurality of computer processors in the fluid transfer management system 74 (see FIG. 1B) that is or are configured to send one or more electronic signals to the electromechanical controller 36 to select among a plurality of functional positions on the multidirectional flow-control valve 41; however, any suitable computer processing arrangement capable of controlling the multidirectional flow-control valve 41 can be used and is envisioned and contemplated herein. Any disclosure in this specification of a single computer processor applies to and can be used with a plurality of computer processors.

In some embodiments, the multidirectional flow-control valve 41 can comprise a stopcock with a plurality of functional positions, such as a first position that enables fluid communication between the outlet fluid connector 42 and the intermediate container or pumping region 40 (but not the inlet fluid connector 32, in some embodiments); a second position that enables fluid communication between the inlet fluid connector 32 and the intermediate container or pumping region 40 (but not the outlet fluid connector 42, in some embodiments); and a third position that enables fluid communication between the outlet fluid connector 42 and the inlet fluid connector 32 (but not the intermediate container or pumping region 40, in some embodiments). For example, in some embodiments, when the stopcock is in the first position, fluid can flow from the intermediate container or pumping region 40 to the destination container 44 or vice versa; when the stopcock is in the second position, fluid can flow from the source container 39 to the intermediate container or pumping region 40 or vice versa; and when the stopcock is in the third position, fluid can flow from the source container 39 to the destination container 44 or vice versa. Further, in some embodiments, when the stopcock is in the first position, the intermediate fluid connector 38, the stopcock, and the outlet fluid connector 42 can comprise at least a portion of a flow path between the intermediate container or pumping region 40 and the destination container 44; when the stopcock is in the second or fourth position, the inlet fluid connector 32, the stopcock, and the intermediate fluid connector 38 can comprise at least a portion of a flow path between the source container 39 and the intermediate container or pumping region 40; and when the stopcock is in the third position, the inlet fluid connector 32, the stopcock, and the outlet fluid connector 42 can comprise at least a portion of a flow path between the source container 39 and the destination container 44. In some embodiments, the stopcock can comprise at least a portion of one or more flow paths between or among two or more containers (e.g., the source container 39, the intermediate container or pumping region 40, and/or the destination container 44) without the use of any connectors (e.g., the inlet fluid connector 32, the intermediate fluid connector 38, and/or the outlet fluid connector 42) when in the first, second, third, and/or fourth position. Other arrangements can be used are also appreciated and contemplated herein, including, for example, stopcocks configured to have more or less than three positions (e.g., stopcocks configured to have 2, 4, 5, or more positions).

In some embodiments, the fluid transfer module 31 can be a single-use or limited-use, disposable device that is configured to be periodically removed from and replaced within the fluid transfer device 30, such as after a single dosage of medication for a particular patient has been transferred and/or after one particular type of medication has passed through the fluid transfer module 31 (e.g., to avoid mixing of medications when not desired).

Figure 1B:
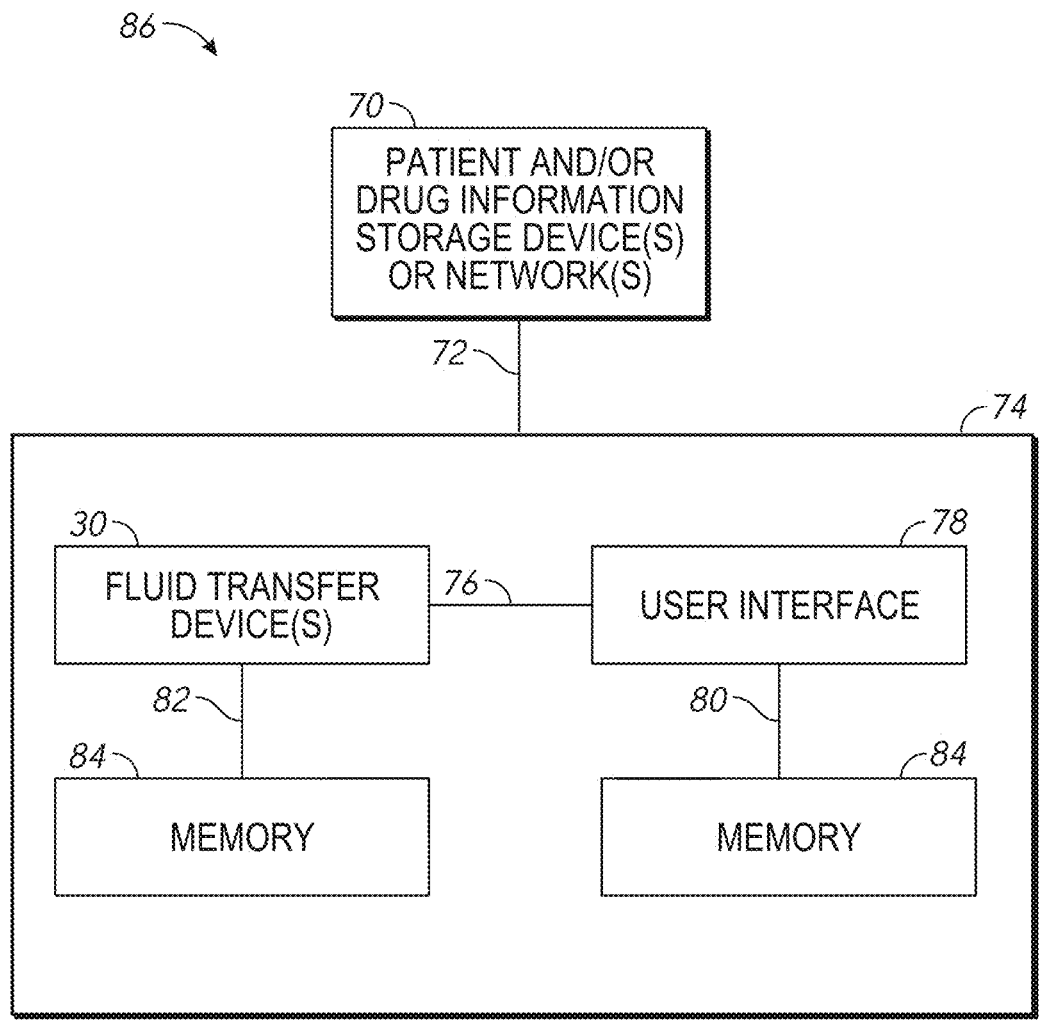
FIG. 1B is a schematic illustration of an example of a system for transferring medical fluid that includes the fluid transfer device of FIG. 1A.

FIG. 1B is a schematic illustration of a fluid transfer system 86 for transferring medical fluid that includes the fluid transfer device 30 of FIG. 1A, according to some embodiments. For example, as shown in FIG. 1B, one or more fluid transfer devices 30 can form part of a fluid transfer system 86 that can include one or more of the following components that can be selectively positioned in electronic communication between or among each other: one or more electronic patient and/or drug information storage devices or networks 70; one or more fluid transfer management systems 74 comprising one or more fluid transfer devices 30, a user interface 78, and/or one or more memories 84. In some embodiments, the one or more electronic patient and/or drug information storage devices or networks 70 can be physically remote from the fluid transfer management system 74. For example, in a health clinic or hospital, the one or more electronic patient and/or drug information storage devices or networks 70 can comprise a remote patient information management system with a database that can be queried to provide information about a particular patient's needs for medical fluids (e.g., a drug prescription) that may include the type, dosage, lot number, expiration date, and/or concentration of one or more drugs or other medical fluids to be provided to a patient, and/or identifying information regarding one or more health care provider who prescribed, requested, and/or filled the destination container, and/or the time and/or date associated with any or all of these activities. Any medical information, such as any of the foregoing medical information, can be provided by the one or more fluid transfer devices 30 for recording and storage in the patient information management system.

The various components of the fluid transfer system 86 can communicate between or among themselves in any suitable manner, as identified in FIG. 1B. For example, as illustrated, the one or more patient and/or drug information storage device(s) or network(s) 70 can electronically communicate with the fluid transfer management system 74, or any components thereof, by way of an electronic communication link 72, formed by any suitable electronic communication device, such as a wired connection, a local area network, a wide area network, the Internet, and/or a wireless connection (including, e.g., Wi-Fi, Bluetooth, Ant+, ZigBee, cellular, etc.), or any other electronic communication device (collectively referred to as "electronic communicators"). The fluid transfer management system 74 may comprise a wireless communication console, such as a Wi-Fi box that is configured to send and/or receive data, including patient data, data regarding a fluid transfer, data regarding the type, dosage, concentration, volume, image, technician, physician, and/or time of a fluid transfer, and/or data to control the electronic fluid transfer system 86, etc. The fluid transfer device 30 can communicate with a memory 84 by any suitable electronic connection, such as a wired connection, or any other electronic communicators. In some embodiments, the memory 84 is part of the fluid transfer device 30, in that a common housing is provided for containing or supporting both.

The user interface 78 can communicate with one or more fluid transfer devices 30 and/or with one or more patient and/or drug information storage device(s) or network(s) 70 by way of any suitable electronic communication device 76, including by way of any wireless device or by way of any other of the electronic communicators. In some embodiments of the fluid transfer management system 74 in which there are multiple fluid transfer devices 30, a single user interface 78 can electronically communicate with a plurality of fluid transfer devices 30 to control and/or monitor multiple fluid transfers operating generally simultaneously or generally in parallel. In some embodiments of the fluid transfer management system 74 in which there are multiple fluid transfer devices 30, one or more user interfaces 78 can electronically communicate with a plurality of fluid transfer devices 30 to control and/or monitor multiple fluid transfers operating generally simultaneously or generally in parallel. The user interface 78, like the fluid transfer device 30, can electronically communicate with or include a memory 84 by way of a wired connector 80 or any other of the electronic communicators. The memory 84 of the user interface 78 can be part of the user interface 78 in that a common housing can be provided for containing or supporting both. Each of the components of the fluid transfer management system 74 as shown in FIG. 1B (e.g., the fluid transfer device(s) 76, the user interface 78, and the memory or memories 84) can be provided in a single housing, or can be provided as discrete components or discrete collections of components.

FIGS. $2A_i$-$2D_i$ illustrate various features, components, and arrangements that can be included in some embodiments of the fluid transfer device 30 and fluid transfer module 31 shown in FIG. 1A and the fluid transfer management system 74 shown in FIG. 1B. As will be described in more detail below, FIG. $2A_i$ illustrates an example of an electromechanical system 200 (also referred to as a fluid transfer unit 200); FIG. $2B_i$ illustrates an example of a fluid transfer module 31 in the form in this example of a fluid pump assembly 224; FIG. $2C_i$ illustrates the fluid pump assembly 224 of FIG. $2B_i$ removably attached to the fluid transfer unit 200 of FIG. $2A_i$; and FIG. $2D_i$ illustrates an example of a portion of an electro-mechanical controller 36 in the form in this example of a driver 212. Unless otherwise noted, like reference numerals among FIGS. $2A_i$-$2D_i$ indicate identical or functionally and/or structurally similar elements, and reference numerals in the below discussion corresponding to elements labeled in FIGS. 1A and 1B refer to elements that are the same as or generally similar to the elements of FIGS. 1A and 1B.

Turning to FIG. $2A_i$, this figure illustrates an example of a portion of a fluid transfer management system 74 with a remote user interface 78. For example, in some embodiments, FIG. $2A_i$ illustrates a front perspective view of a fluid transfer unit 200 for transferring medical fluid. In some embodiments, the fluid transfer unit 200 is an example of a portion of the fluid transfer device 30 shown in FIG. 1A or the fluid transfer system 86 shown in FIG. 1B. As shown in the figures, the fluid transfer management system 74 can comprise a fluid transfer unit 200 that comprises a housing 202, one or more carrying handles 208, one or more base supports 223, a destination-container support (e.g., a generally vertical pole stand 204 and/or a generally horizontal support arm 242), and one or more supports configured to receive and retain at least a portion of the fluid transfer module 31 (e.g., the intermediate container or pumping region 40). In some embodiments, the supports can include one or more protruding holders 220, one or more receptacles 218 (such as a recess 218, as illustrated); one or more sensor devices 214 with one or more channels that include one or more sensors 215; one or more movable platforms 222 for receiving at least a portion of the fluid transfer module 31 and/or for facilitating the transfer of fluid; and/or one or more attachment regions 210 for attaching to or receiving a multidirectional flow-control valve 41. As will be described in more detail below, the fluid transfer device 30 or the fluid transfer unit 200 can include a driver 212, which can form part of the electro-mechanical controller 36 of FIG. 1A, and the one or more sensor devices 214 can include one or more indicators 216. The one or more base supports 223 can be attached to or integrally formed with the housing 202 to help stabilize the fluid transfer unit 200 (e.g., to help prevent it from tipping over). Although not shown in FIG. $2A_i$, in some embodiments, the one or more base supports 223 can extend across an underside of the housing 202.

In some embodiments, at least one or more portions of the housing 202, such as the one or more receptacles 218 (e.g., the recess 218 illustrated in FIG. $2A_i$), can be transparent to enable one or more measuring instruments positioned inside of the housing 202 to capture an image or other data on the outside of the housing. For example, a volume sensor (see FIG. $2E_{ii}$) can determine the volume of liquid being transferred to one or more containers (e.g., source container 39, intermediate container or pumping region 40, and/or destination container 44). For example, in some embodiments, the volume sensor can be configured to sense the volume in the intermediate container or pumping region 40 through the transparent recess 218. It will be understood that this same volume sensor or one or more other volume sensors can be configured to sense the volume of one or more other containers in addition to or in lieu of the intermediate container or pumping region 40 (e.g., the source container 39 and/or the destination container 44, among others), for example, through one or more transparent receptacles 218 and/or through one or more other sections of the housing 202 that are transparent. The volume sensor can comprise, for example, any appropriate sensor or combination of sensors to provide information about the volume of the liquid in a container, such as an optical sensor (e.g., a camera or a break-beam sensor), an infrared sensor, an acoustic sensor (e.g., an ultrasonic sensor), and/or a mass or weight sensor, among others.

The volume sensor can be used, for example, to control and/or to provide a record of the volume and/or type of fluid transferred to a patient, such as, for example, by sensing and/or recording the volume and/or one or more other characteristics (e.g., color, viscosity, concentration, lot number, expiration date, etc.) of the liquid in a container (e.g., the intermediate container, or pumping region 40, and/or the source container 39 and/or the destination container 44) before, during, and/or after it is transferred to a patient. For example, in some embodiments, a camera can be used to capture an image of the intermediate container or pumping region 40 to confirm or measure the volume therein. A data file can then be created and stored in a memory 84 which has one of more items of information, such as patient identifying information, the date and time the liquid was transferred and/or the volume or other characteristic(s) of the liquid was or were confirmed and recorded, the type (name, brand, and/or concentration, etc.) of medical fluid transferred, the volume of medical fluid transferred, and/or one or more images of the intermediate container or pumping region 40 with liquid inside, etc. The same or a similar data file can be created for any one of the suitable volume sensors described above. In some embodiments, the fluid transfer unit 200, the fluid transfer device 30, and/or the fluid transfer system 86 can include one or more measuring instruments, such as one or more volume sensors. In some embodiments, the one or more measuring instruments or volume sensors can be internal and/or external to the fluid transfer unit 220, or partially external and partially internal, such as when a portion of the instrument or sensor is inside of the housing 212 and a portion of the sensor protrudes from the housing 212.

Figure 2A:
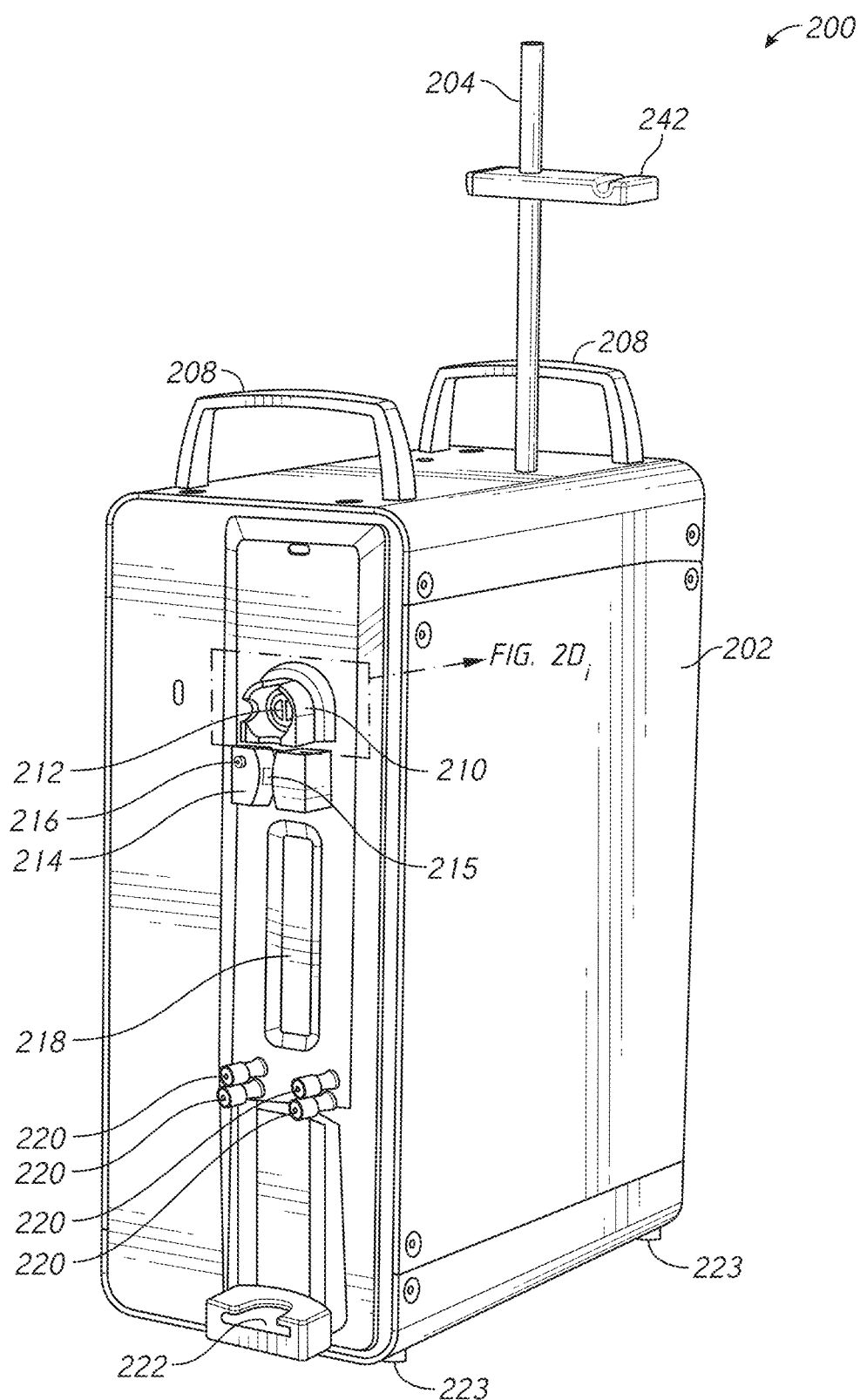
Figure 2B:
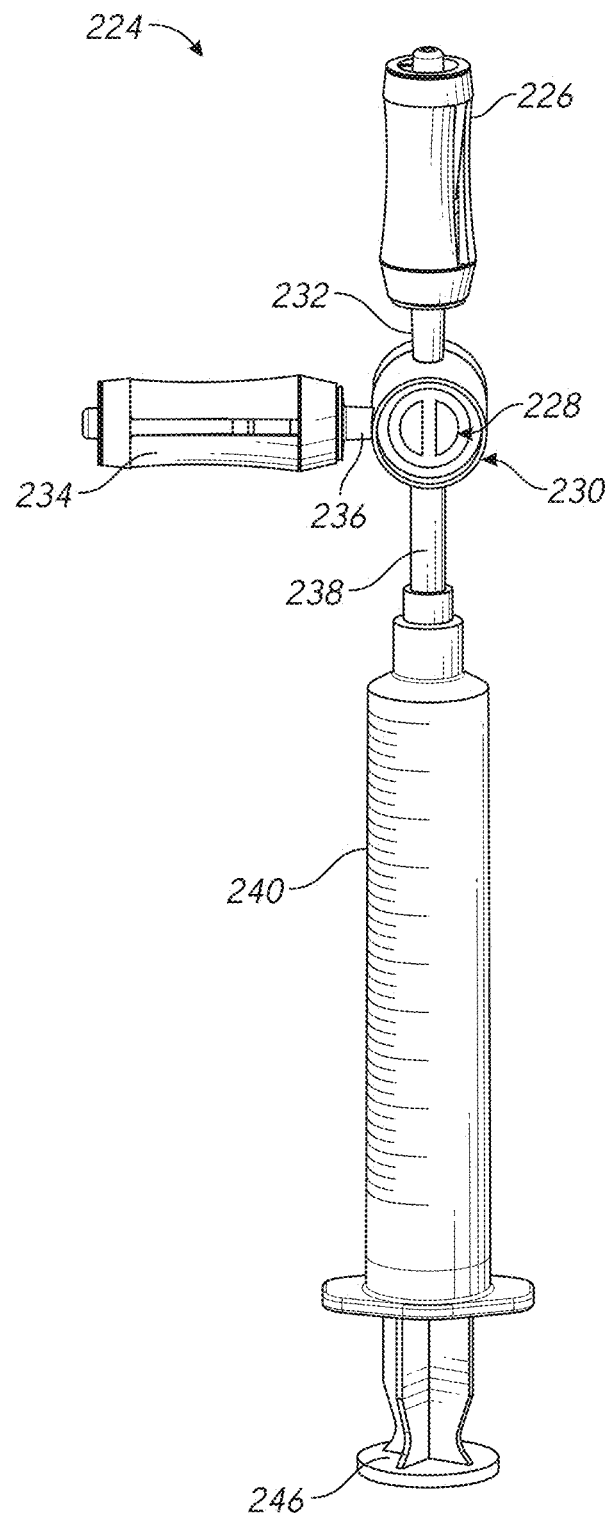

FIG. 2B$_i$ illustrates a rear view of an example of a fluid transfer module 31 of FIG. 1A in the form in this example of a fluid pump assembly 224, such as a multi-stroke fluid pump assembly 224. As shown in the figures, in some embodiments, the fluid pump assembly 224 comprises: an inlet fluid connector 32 in the form in this example of a conduit 232 and a selectively openable and closeable fluid connector 226; a multidirectional flow-control valve 41 in the form in this example of a fluid stopcock 230; an outlet fluid connector 42 in the form in this example of a conduit 236 and a selectively openable and closeable fluid connector 234; and an intermediate container 40 in the form in this example of a syringe pump 240 that is attached (e.g., bonded) to the fluid stopcock 230 via a conduit 238. The fluid pump assembly 224 can be a limited-use or single-use, disposable device that is configured to be routinely removed, discarded, and replaced with a new disposable device in position on the fluid transfer unit 200.

A multidirectional flow-control valve 41, such as a fluid stopcock 230, can be particularly useful in some embodiments because it can permit variability and control of the direction and/or orientation of the fluid pathway within the fluid transfer module 31. In some embodiments, the flow-control valve 41 can be configured, as illustrated throughout this specification, to selectively enable a plurality of discrete settings, each setting enabling fluid connections within the fluid pathway of the fluid transfer module 31 among two or more different components of the fluid transfer module 31, and closing-off or isolating one or more other fluid connections of one or more other components from the fluid pathway of the fluid transfer module 31. The flow-control valve 41 can be configured to change between the plurality of discrete settings.

In some embodiments, as illustrated, such change or changes of settings or connections within the flow-control valve 41 can be accomplished electronically and independently of changes to fluid pressure within the fluid transfer module 31. For example, in some embodiments, a pressure differential can arise between two or more parts or components of the fluid transfer module 31 without causing any change of connections within the fluid transfer module 31 and/or without enabling fluid communication between different portions of the fluid transfer module 31 that, before such pressure differential, were not previously in fluid communication with each other.

In some embodiments, the multidirectional flow-control valve 41 is not a one-way valve or a series of one-way valves; rather, the multidirectional flow-control valve 41, in each particular electronically selectable setting, can provide a full two-way fluid pathway between two or more components of the fluid transfer module 31. For example, in some embodiments, in one or a plurality of discrete, electronically selectable settings, the flow-control valve 41 can provide a two-way fluid pathway between the inlet fluid connector 226 and the outlet fluid connector 234; and/or a two-way fluid pathway between the inlet fluid connector 226 and the intermediate container 40 or syringe pump 240; and/or a two-way fluid pathway between the intermediate container 40 or syringe pump 240 and the outlet fluid connector 234. In some embodiments, the multidirectional flow-control valve 41 can enable fluid withdrawn from a source container 39 to be partially or fully returned to a source container 39, in some situations, which can be particularly advantageous, such as, for example, during priming and/or purging of a fluid transfer module 31, although other situations in which this type of fluid flow are also contemplated and can be used.

In some embodiments, either or both of the fluid connectors 226, 234 can be industry standard medical connectors (e.g., luer connectors complaint with ISO 594 or compliant with any other industry standard) that are resealable and fluid-tight, such as the Clave® female medical connector or the Spiros® male medical connector or either of the male or female sides of a Chemolock® medical connector system, all sold by ICU Medical, Inc. Examples of embodiments of these and other devices, among many others, that can be used as fluid connectors 226, 234, or as any portions thereof, are included in U.S. Pat. Nos. 5,873,862; 7,998,134; and U.S. Published Patent Application No. 2014/0246616, all of which are incorporate by reference in this specification in their entireties. Any feature, structure, material, step, or component described and/or illustrated in any of the foregoing patents or published application can be used with or instead of any feature, structure, material, step, or component described and/or illustrated in any other portion of this specification.

In some embodiments, the fluid stopcock 230 can comprise a device that selectively permits fluid communication between and/or among multiple apertures and/or channels in the stopcock 230. For example, as shown in FIG. 2B; and as described above, the fluid stopcock 230 can selectively permit fluid communication between any two of the inlet fluid connector 226, the outlet fluid connector 234, and the intermediate container 40 or syringe pump 240. The selection between and/or among the multiple apertures and/or channels in the stopcock 230 can be accomplished by actuating the stopcock 230, such as by utilizing an electromechanical controller 36 in the fluid transfer unit 200 to actuate a driving interface 33 on the stopcock 230, such as in the form in this example of a rotatable actuator 228. As described above, the electromechanical controller 36 can be controlled by sending one electronic signal or a series of electronic signals from one or more computer processors associated with the fluid transfer device 30. As shown in FIG. 2B$_i$, the rotatable actuator 228 can include one or more recesses and/or protrusions that are configured to interface with a driver 212 of a fluid transfer unit, such as a driver 212 that includes one or more recesses and/or protrusions that comprise one or more shapes that are complementary with or generally match or correspond with the recesses and/or protrusions of the actuator 228. The driver 212 may be controlled via a driver motor and driver shaft. The electromechanical controller 36 may send a signal activating driver motor and driver shaft to initiate driver 212 movement, and/or to continue and/or stop driver 212 movement. When a rotatable actuator interfaces with the driver 212, the driver 212 may allow the electromechanical controller to select between and/or among the multiple apertures and/or channels in the stopcock 230. As in every embodiment in this specification, any component, structure, feature, or step that is illustrated and/or described in connection with FIG. 2E$_{ii}$ (including the internal components) can be used with or instead of any component, structure, feature, or step that is illustrated and/or described in connection with any other figure or embodiment in this specification.

FIG. 2D$_i$ is a magnified partial front view of the fluid transfer unit 200 of FIG. 2A$_i$, which illustrates an attachment region 210 and the recesses and/or protrusions of the driver 212, according to some embodiments. However, it will be understood that many different types and/or patterns of recesses and/or protrusions can be used, depending, for example, upon functional and aesthetic preferences. In some embodiments, one or more of the types and/or patterns of recesses and/or protrusions, and/or one or more of the types of materials (such as a tacky or slide-resistant material with a high coefficient of friction) can provide resistance to rotational disengagement or slipping during actuation.

Returning to FIG. $2B_i$, this figure also illustrates an example of a syringe pump 240. In some embodiments, the syringe pump 240 includes an actuator, such as an actuating stem 241, that can be reciprocated back-and-forth or up-and-down to move an internal plunger, thereby decreasing or increasing the fluid-carrying volume inside of the syringe pump 240. A first stroke of the multi-stroke fluid pump assembly 224 in the form in this example of a syringe pump 240 can be accomplished by drawing the actuating stem 241 at least partially out of the body of the syringe pump 240, thereby drawing fluid into the syringe pump 240, and then reversing the direction of the syringe pump 240, pushing the actuating stem 241 back toward the body of the syringe pump 240, thereby expelling the drawn-in fluid out of the syringe pump 240.

In some embodiments, as shown, for example, in FIG. $2B_i$, the conduit 238 of the multi-stroke pump assembly 224 can be longer than the conduits 232, 236 extending between the fluid stopcock 230 and the fluid connectors 226, 235. The conduit 238 can be permanently coupled to the fluid stopcock 230 on one end, and to the syringe pump 240 on the other end. Other arrangements are also contemplated and can be used.

As illustrated, in some embodiments, the fluid transfer module 31 (such as the fluid pump assembly 224) can form part of or constitute a closed system, in that: (i) liquid, or fluid, and/or vapors contained or sealed within the fluid transfer module 31 are prevented from exiting or escaping from the fluid transfer module 31, and/or (ii) the exiting or escaping of liquid, or fluid, and/or vapors is resisted in a clinically significant manner to diminish or avoid one or more clinical risks or negative outcomes, when the fluid transfer module 31 is disconnected from other components of the fluid transfer device 30. As shown, in some embodiments, the entire fluid pathway within the fluid transfer device 30 can constitute a closed system or a seal system. As used in this specification, the term "closed system" or "sealed" or any similar terms are used in accordance with their customary meanings in the field of medical infusion, and these terms include the requirement that fluids stay inside of the fluid transfer module 31 or the fluid transfer device 30 (or components thereof) under normal conditions or use such that any small amount of escaping fluid or vapors would not have any significant adverse clinical effects under normal conditions or use. In some embodiments, as shown in FIGS. 1A and $2B_i$, the fluid transfer module 31 can be automatically closeable and resealable at each terminal end of the module 31 (e.g., at the inlet fluid connector 32, at the intermediate fluid connector 38, and/or at the outlet fluid connector 42). When either or both of the fluid transfer module 31 and/or the fluid transfer device 30 are sealed and/or constitute part of a closed system, the risk of ingress of harmful substances (e.g., bacteria or viruses or other microbes) into the fluid pathway is diminished, and the risk of egress of harmful substances (e.g., chemotherapy or immunosuppressive drugs) from the fluid transfer device 30 or the fluid transfer module 31 into the surrounding environment of a healthcare facility is diminished.

FIG. $2C_i$ is a front perspective view of another type of fluid transfer module 31 that is removably attached to the fluid transfer unit 200 of FIG. $2A_i$. The fluid transfer module 31 is identical to the fluid pump assembly 224 of FIG. $2B_i$, except that Chemolock connectors 234a, 226a are used rather than Spiros connectors, in this example. Any suitable type of connector or combination of connectors can be used. As illustrated in FIG. $2C_i$, the fluid transfer module 31 (also referred to as a multi-stroke fluid pump assembly 224) can be removably attached to the fluid transfer unit 200, such as by using one or more of the supports on the fluid transfer unit 200. For example, as shown in FIG. $2C_i$, a flat portion or end of the actuating stem 241 can be inserted into or coupled with a receiving region of the movable platform 222; one or more tabs on the syringe pump 240 can be positioned on or inserted between one or more of the protruding holders 220; the body of the syringe pump 240 can be received in the receptacle 218; the conduit 238 can be inserted into or on the sensor device 214, such as in a channel within the sensor device 214 that includes one or more sensors 215 (also referred to as one or more sensing regions 215; and/or the body of the fluid stopcock 230 can be positioned in or on or inserted into the attachment region 210 of the fluid transfer unit 200. In some embodiments, the fluid transfer device 30, such as in the form in this example of a multi-stroke fluid pump assembly 224, can be attached to the fluid transfer unit 200 in a single motion by simply advancing the transfer device 30 into contact with a face on the fluid transfer unit 200 that includes one or more of the supports 220. The fluid transfer device 30 can be removably retained on the fluid transfer unit 200 by any suitable attachment structure, including a snap-fit, a friction fit, a clasp, a clip, a retaining arm or door, an elastic band, or any other attachment structure.

When the fluid transfer module 31 (e.g., the fluid pump assembly 224) is removably attached to the fluid transfer unit 200, a fluid-observation region on the conduit 238 of the fluid transfer device 30 can be positioned adjacent to or within an appropriate sensing distance from the one or more sensors 215. In the illustrated example, the fluid-observation region of the fluid transfer device 30 is at least a portion of the conduit 238 positioned between the multidirectional flow-control valve 41 (e.g., the fluid stopcock 230) and/or the intermediate container or pumping region 40 (e.g., the syringe pump 240). In some embodiments, the fluid-observation region of the fluid transfer device 30 can comprise a portion of the conduit 238 positioned between the multidirectional flow-control valve 41 (e.g., the fluid stopcock 230) and/or the intermediate container or pumping region 40 (e.g., the syringe pump 240). In some embodiments, the fluid-observation region can be positioned in another position on the fluid transfer device 30, or there can be multiple fluid-observation regions 30 located at a plurality of positions on the fluid transfer device 30.

In some embodiments, the one or more sensors 215 can be configured to determine whether there is liquid, gas (e.g., one or more bubbles), and/or a vacuum or partial vacuum, within a particular region or regions of the fluid transfer module 31 (e.g., fluid pump assembly 224). For example, as illustrated in the figures, the one or more sensors 215 can be configured to determine whether there is a medical fluid within at least a portion of the conduit 238 or whether there is a gas (e.g., ambient air or air bubbles) or a vacuum or partial vacuum within the conduit 238. In some embodiments, the one or more sensors 215 can determine whether there is a medical fluid within a portion of the conduit 238 or whether there is a gas (e.g., ambient air) or a vacuum or partial vacuum within a portion of the conduit 238. The one or more sensors 215 can be any suitable type of sensor, including but not limited to one or more acoustic sensors (e.g., ultrasonic sensors), infrared sensors, laser sensors, visual-spectrum optical sensors, motion flow sensors, or any other suitable sensors. One or more indicators 216, such as an indicator light or indicator speaker or other indicator, can be positioned on the sensor device 214 to indicate when the sensor device 214 is sensing a particular condition, such as when liquid is present in the fluid observation-region.

Figure 2C:
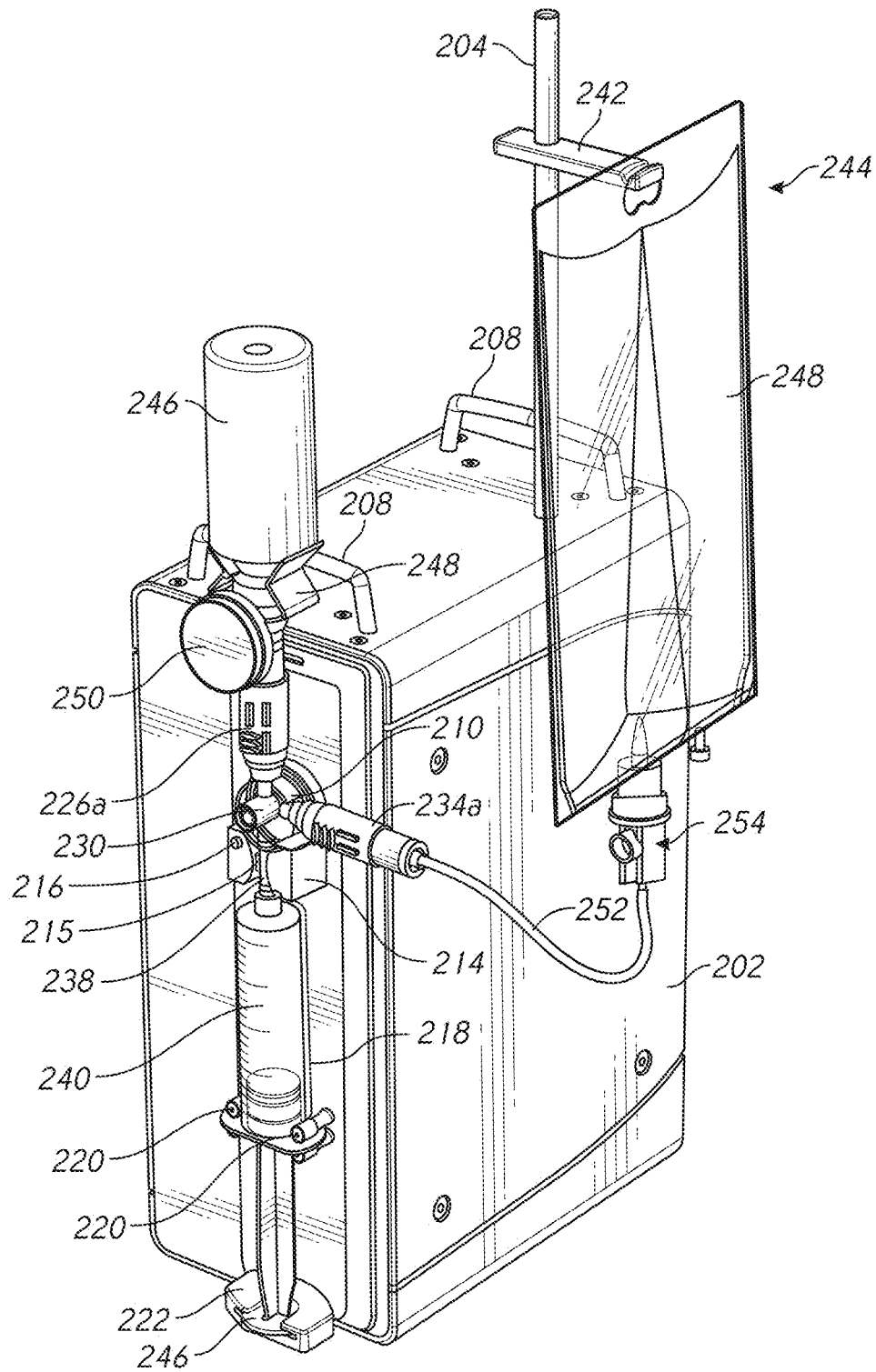

FIG. 2C$_i$ also illustrates a fluid source container 39 in the form in this example of an inverted vial 246 attached to a vial adaptor 248 that is in turn attached to an inlet connector 32 in the form in this example of a male fluid connector 226a with a longitudinal locking mechanism. In some embodiments, the vial adaptor 248 comprises a filtered fluid inlet and/or outlet 250 and securing arms that are configured to securely receive the vial. FIG. 2C$_i$ also illustrates a fluid destination container 44 in the form in this example of an IV bag 244 attached to a conduit or hose 252 (in this example by way of a bag spike 254 or other fluid connection point) that is in turn attached to the outlet connector 42 of the fluid transfer module 31. The outlet connector in FIG. 2C$_i$ is in the form in this example of a male fluid connector 234a with a longitudinal locking mechanism. The IV bag 244 is suspended from the pole stand 204 by the support arm 242.

FIGS. 2A$_{ii}$-2D$_{ii}$ illustrate various features, components, and arrangements that can be included in some embodiments of the fluid transfer device 30 shown in FIG. 1A and the fluid transfer system 86 shown in FIG. 1B. Similar to FIGS. 2A$_i$-2D$_i$, FIG. 2A$_{ii}$ illustrates an example of an electromechanical system 200 (also referred to as a fluid transfer unit 200), FIG. 2B$_{ii}$ illustrates an example of a fluid transfer module 31 in the form in this example of a fluid pump assembly 224; FIG. 2C$_{ii}$ illustrates the fluid pump assembly 224 of FIG. 2B$_{ii}$ removably attached to the fluid transfer unit 200 of FIG. 2A$_{ii}$; and FIG. 2D$_{ii}$ illustrates an example of a driver 212. Unless otherwise noted, reference numerals in FIGS. 2A$_{ii}$-2D$_{ii}$ refer to elements that are the same as or generally similar to the components of FIGS. 1A-2D$_i$. For example, the fluid transfer unit 200 of FIG. 2A$_{ii}$ is generally similar to the fluid transfer unit 200 shown in FIG. 2A$_i$, except that the one or more base supports 223 extend across an underside of the housing 202 at base support region 223a. FIG. 2A$_{ii}$ also illustrates one or more trays 280 attached to the housing 202 configured to support one or more containers and/or conduits described and contemplated herein. The one or more trays 280 may comprise any one of various structures to support containers and/or conduits. For example, in some embodiments, the one or more trays 280 may comprise one or more racks with one or more slots capable of holding vials. In some embodiments, the one or more trays 280 may be configured to support a source bag and/or an IV bag, such as a saline or diluent bag and/or a bag containing therapeutic or medicinal liquid. The one or more trays 280 may be removably attached to the housing 202. In some embodiments, one tray 280 can be configured to support a saline or diluent source container and another tray 280 can be configured to support a source container with therapeutic or medicinal liquid. Among other structural differences, the supports 220 in FIG. 2A$_{ii}$ are shaped differently from those shown in FIG. 2A$_i$, albeit their function is the same or similar. As with all embodiments in this specification, any feature, structure, material, step, or component of any embodiment described and/or illustrated in connection with FIGS. 2A$_i$-2D$_i$ can be used by itself, or with or instead of any other feature, structure, material, step, or component of any other embodiment described and/or illustrated in connection with FIGS. 2A$_{ii}$-2E$_{ii}$.

As another example, FIGS. 2B$_{ii}$ and 2C$_{ii}$ also illustrate an example of a stopcock handle 245. In particular, FIG. 2B$_{ii}$ illustrates a rear view of the stopcock handle 245 attached to the fluid pump assembly 224 and FIG. 2C$_{ii}$ illustrates a front perspective view of the stopcock handle 245 attached to the fluid pump assembly 224 and removably attached to the fluid transfer unit 200. In some embodiments, the stopcock handle 245 comprises an aid for grasping the fluid pump assembly and/or positioning the fluid pump assembly 224 relative to the fluid transfer unit 200. For example, in some embodiments, the stopcock handle 245 can be configured to help position (e.g., attach, engage, remove, and/or disengage) the fluid pump assembly 224 to and/or from one or more features of the fluid transfer unit 200. The stopcock handle 245 can, for example, help engage or disengage the rotatable actuator 228 to or from the driver 212, help push the conduit 238 into or on the sensor device 214, help remove the conduit 238 from the sensor device 214, help attach or remove the actuating stem 246 to or from the receiving region of the movable platform 222, help position the one or more tabs on the syringe pump 240 on or between one or more of the protruding holders 220, help position the body of the syringe pump 240 into the one or more receptacles 218, and/or help position the body of the stopcock 230 into or on the attachment region 210, among any other suitable uses.

In some embodiments, the stopcock handle 245 can be removably attached to the stopcock 230. In some embodiments, the handle is configured to be manipulated (e.g., rotated, slid, pushed, and/or pulled) to manually actuate the stopcock into the various positions described above with reference to, for example, FIG. 1A. It will be understood that the stopcock handle 245 can be utilized in any embodiment illustrated and contemplated herein, including, for example, the embodiments shown in FIGS. 1A, 1B, and 2A$_i$-2D$_i$.

FIG. 2E$_{ii}$ is a rear perspective cross-sectional view of the fluid transfer unit 200 and the fluid pump assembly 224 shown in FIG. 2C$_{ii}$, and illustrates various internal and external functional components. For example, as shown in FIG. 2E$_{ii}$, in some embodiments, a measuring instrument such as a sensor 225 (e.g., a camera) can be positioned within the housing 202 to determine one or more features of the contents of the fluid transfer module 31 or fluid pump assembly 224, such as the volume, or type, or concentration, or color, and/or viscosity of fluid in the intermediate container or pumping region 40 (e.g., by capturing an image of the fluid transfer module 31 or fluid pump assembly 224) to provide a data file as described above. In some embodiments, a shroud 255 can be positioned adjacent to or near or generally around the one or more transparent receptacles 218 to advantageously resist the entry of undesired light from aberrant sources in order to increase the accuracy of the sensor 225. For example, in some embodiments, the shroud 255 can be configured to direct light that passes through the one or more transparent receptacles 218 toward the sensor 225, thereby increasing the amount of light available to the sensor 225. When the sensor 225 is a camera, the shroud 255 can help make the images more accurate and easier and faster to process by the processor(s) of the fluid transfer unit 200.

The fluid transfer unit 200 may comprise one or more computer processors 297, 298, which can form part of or be in electronic communication with any or all of the electromechanical controller 36 of FIG. 1A, the sensor 214, the volume sensor 225, the stopcock motor 290, and/or the platform motor 296, etc. in some embodiments, the one or more computer processors 297, 298 may comprise a pi box and/or a control board. The fluid transfer unit 200 may contain or support a power supply 295 configured to provide power to one or more components of the fluid transfer unit 200. The housing 202 may comprise a seal 293 configured to resist or prevent the entrance into and/or escape of fluid from the housing 202.

In some embodiments, the fluid transfer unit 200 may comprise one or more presence sensors 294*a*, 294*b*, 294*c*. The one or more sensors 294*a*, 294*b*, 294*c* can be positioned within and/or on the housing 202 and can determine the presence or absence of one or more structures. In some embodiments, one or more of the sensors 294*a*, 294*b*, 294*c* can be infrared sensors or any other suitable sensor. One or more of the sensors 294*a*, 294*b* can determine whether the fluid source container 39 (such as vial 246), the source adapter 250, and/or the source fluid connector are present and/or connected to the fluid transfer unit 200. In some embodiments, sensor 294*a* may determine if a source container 246 connector, such as a male or female side of a Chemolock® medical connector system, is properly engaged with a corresponding connector on the fluid transfer unit 200, such as a Chemolock® connector 226*a*. The sensor 294*b* may determine if an intermediate container 40, such as fluid pump assembly 224, and/or connector 226*a*, such as a male or female side of a Chemolock® connector, is present and/or properly engaged with the housing 202 and/or a corresponding connector on a source container 246. The sensor 294*c* may determine whether the destination container 44, such as IV bag 244, and/or destination fluid connector are present and/or connected to the fluid transfer unit 200. In some embodiments, sensor 294*c* may determine if a destination container 44 connector, such as a male or female side of a Chemolock® medical connector system, is properly engaged with a corresponding connector on the fluid transfer unit 200, such as a Chemolock® connector 234*a*. In some embodiments, if any of sensor 294*a*, 294*b*, 294*c* determine that a component of the fluid transfer unit 200 is not present, the sensor 294*a*, 294*b*, 294*c* may send a signal to the controller 36 to prevent initiation of the fluid transfer process and/or terminate an ongoing fluid transfer. The sensor 294*a*, 294*b*, 294*c* may trigger an indicator signaling to a user that not all components are present or properly engaged with the fluid transfer unit 200.

As shown in FIGS. 2A$_i$, 2A$_{ii}$, and 2C$_{ii}$, in some embodiments, one or more apertures in the housing can permit one or more of the presence sensors 294*a*, 294*b*, 294*c* to communicate essentially or completely unimpeded from within the housing to a region outside of the housing. As illustrated, one or more of the presence sensors 294*a*, 294*b*, 294*c* can be positioned in substantially a collinear manner with each other and/or with the primary longitudinal axis of the fluid transfer module 31 (e.g., presence sensors 294*a*, 294*b*), and/or one or more other of the presence sensors 294*a*, 294*b*, 294*c* can be positioned in a non-collinear manner or at an angle or perpendicular to the primary longitudinal axis of the fluid transfer module 31 (e.g., presence sensor 294*c*). In some embodiments, as shown, one or more or all of the sensors are positioned and/or recessed inside of the housing of the electronic fluid transfer system, such that a panel through which the sensors are configured to detect items is essentially or substantially or entirely planar. As illustrated, one or more of the sensors does not include and/or is not attached by any external wires outside of the housing of the electronic fluid transfer system.

In some embodiments, one or more of the sensors 294*a*, 294*b*, 294*c* can be configured to detect the presence or absence of at least a portion of a fluid transfer module attached to the electronic fluid transfer device, such as a connector on the fluid transfer device. In some embodiments, one or more of the sensors (e.g., 294*a*, 294*b*) can be configured to additionally or alternatively detect the presence or absence of or connection with at least a portion of a fluid source system, such as a connector or vial adaptor or vial or bag or conduit that forms part of or is connected to a fluid source system. In some embodiments, one or more of the sensors (e.g., 294*c*) can be configured to additionally or alternatively detect the presence or absence of or connection with at least a portion of a fluid destination system, such as a connector or bag or conduit that forms part of or is connected to a fluid destination system. In some embodiments, the detection of one or more of the fluid transfer module 31, the detection of the connection to the fluid source system, and/or the detection to the connection to the fluid destination system can be a gating step or a required step for the computer processor or other component of the electro-mechanical controller to permit fluid transfer to begin or continue.

FIG. 3 illustrates a user interface 78 that can be used with the fluid transfer unit 200 in the form in this example of a remote tablet. The user interface 78 can comprise a rechargeable internal battery, a touch-sensitive screen to enable user selection and input by way of the screen, and one or more additional or alternative user inputs 256, such as a button (as shown) or a knob or a slider or a rocking switch, or a rolling dial, or any other user input. The user interface 78 can communicate electronically with one or more fluid transfer units 200 and/or with one or more patient and/or drug information storage devices or networks 70 utilizing any suitable electronic protocols or electronic communicators. In some embodiments, the user interface 78 is fixed to the fluid transfer unit 200, such as being attached to or contained at least partially within the housing of the fluid transfer unit 200.

The user interface 78 can display or convey various items of information between a user and an electronic storage medium and/or can convey one or more executable instructions to a computer processor in the fluid transfer unit 200, or to electromechanical hardware in the fluid transfer unit 200, to perform one or more actions relating to fluid transfer. For example, the user interface 78 can receive and/or store (e.g., by user input or electronic transmission) the identity of the pharmacist or technician who is performing the fluid transfer, the identity of the patient, the name of the medical fluid, the volume of medical fluid to be transferred, the lot number, the expiration date of the medical fluid, and/or the date and time on which the fluid transfer was performed, etc. Also, as other examples, the user interface 78 can assist in controlling the fluid transfer by receiving and conveying commands from the user via the user interface 78 and/or displaying messages from the fluid transfer unit 200 regarding the progress and/or status of the fluid transfer, such as commands initiating the fluid transfer and/or halting the fluid transfer, and/or one or more messages demonstrating the amount of fluid transferred at any given moment, or the history of fluid transfers for a particular patient or pharmacist over a particular period, or one or more error messages indicating that the fluid transfer was not completed or that the fluid source container 39 is not connected or is empty, or the fluid destination container 44 is not connected or is full, or any other useful message.

As shown in FIG. 4, in some embodiments, the user interface 78 can be universally compatible with a plurality of different fluid transfer devices 30 and a plurality of different types of fluid transfer devices 30. For example, a single user interface 78 can be configured to electronically communicate with (e.g., by transferring data to and/or from) a plurality of different fluid transfer devices 30 of the same type, or a plurality of different fluid transfer devices 30 of a different type, that are performing separate fluid transfer operations, such as filling destination containers with a plurality of different therapeutic fluids and/or for a plurality of different patients. The user interface 78 can be configured to simultaneously or generally concurrently control and/or record information from any or a plurality or all of such operations. The user interface 78 can comprise a plurality of different communication capabilities, including a plurality of different electronic communicators and/or a plurality of different communication protocols for use with any of such electronic communicators. The user interface 78 can be updated electronically to enable it to communicate electronically using protocols that are not originally used or installed on the user interface, which can enable the user interface 78 to become compatible with future or different types of fluid transfer devices 30, without requiring replacement of the fundamental components of the electronic communication system.

FIGS. 5A-5C are various schematics of fluid transfer modules 45, according to some embodiments. FIG. 5A is a schematic of a fluid transfer module 45 having a bubble trap 15 in fluid communication with a source container 39. FIG. 5B is a schematic of the fluid transfer module 45 of FIG. 5A disconnected from the source container 39 and in fluid communication with a patient 70. FIG. 5C is a schematic of a fluid transfer module 45 having a bubble trap 15 in fluid communication with the fluid transfer module 31 of FIG. 1A. Unless otherwise noted, reference numerals in FIGS. 5A-5C refer to components that are the same as or generally similar to the components in the preceding figures.

As shown in FIG. 5A, the fluid transfer module 45 can include a bubble trap 15 and a destination container 44 in fluid communication with a source container 39. The destination and source containers 44, 39 can comprise any suitable container as described above with reference to FIG. 1A. For example, in some embodiments, the source container 39 can be a vial or a syringe and the destination container 44 can be an IV bag or a cassette reservoir (e.g., a CADD® cassette reservoir). Although not shown in FIG. 5A, the bubble trap 15 can be connected to the destination and source containers 44, 39 with any suitable connector or arrangement of connectors. For example, an inlet of the bubble trap 15 can be configured to attach to a needless connector (e.g., a NEUTRON CLAVE® connector, a MICROCLAVE® Neutral Displacement connector, and the like) and the opposite end of the needless connector can be configured to attach to, for example, a syringe. As another example, an outlet of the bubble trap 15 can be configured to attach to, for example, an open female hub at the end of a fluid line of a CADD® cassette. It will be appreciated that the open female hub can be any closed connector (luer or not), including, for example, a CLAVE® connector, among others.

In some embodiments, the bubble trap 15 can be provided as an adapter to be coupled to a container (e.g., the destination and source containers 44, 39). For example, in some embodiments, the bubble trap 15 can be provided in a package with a container. For example, in some embodiments, the bubble trap 15 can be provided in a package with a syringe, with a cassette, with a fluid bag, with a fluid line, etc. It will be appreciated that the package can include more or less components, assembled or disassembled.

With further reference to FIG. 5A, medical fluid can be transferred from the source container 39, through the bubble trap 15, and into the destination container 44. Because the source container 39 and various components of the fluid module 45 (e.g., connectors and fluid lines) often contain gas (e.g., air), when medical fluid is transferred from the source container 39, gas is often transferred as well, either from the source container 39 or from one of the various components along the way. However, the presence of gas is undesirable in the destination container 44 as it poses a risk to the patient if it ever enters their blood stream (e.g., air embolisms can cause medical complications ranging from discomfort to death). As a result, considerable effort is typically spent manually removing all of the gas from the destination container 44 before it is fluidically connected to a patient. Advantageously, the bubble trap 15 in FIG. 5A can be configured to prevent or otherwise inhibit the flow of gas into the destination container 44. As will be described in more detail below, the bubble trap 15 can be configured to both capture gas and allow liquid to flow through.

In some embodiments, once the destination container 44 is filled with fluid, the fluid transfer module 45 can be disconnected from the fluid source 39 and then connected to a patient. For example, FIG. 5B is an example schematic of the fluid transfer module 45 of FIG. 5A disconnected from the source container 39 and in fluid communication with a patient 70. The source container 39 is shown disconnected from the fluid transfer module 45. It will be appreciated that the destination container 44 in FIG. 5B is acting as a source container and that its name was not adjusted to reflect this so that modularity of the fluid transfer module 45 could be emphasized and illustrated. In FIG. 5B, the bubble trap 15 can be configured to trap (also referred to as capture) air that is discharged from the destination container 44 or fluid lines before it reaches the patient. Although not shown in FIG. 5B, in some embodiments an air detection system can positioned between the bubble trap 15 and the patient 70 to sound an alarm and/or stop the transfer of fluid if it detects gas or a bubble.

FIG. 5C is a schematic of a fluid transfer module 45 having a bubble trap 15 in fluid communication with the fluid transfer module 31 of FIG. 1A. In some embodiments, the fluid transfer module 45 can be removably attached to the fluid transfer module 31 such that the fluid transfer module 45 can be connected to a patient as shown, for example, in FIG. 5B.

FIGS. 6A-6C are various schematics of bubble traps 15, according to some embodiments. FIG. 6A is a schematic of a bubble trap 15 having an elongated chamber 17 and an outlet projection 18. FIG. 6A' is a schematic of the bubble trap 15 of FIG. 6A with inlet and outlet luer connectors 20a, 20b. FIG. 6B is a schematic of a bubble trap 15 having a curved chamber 17 and an outlet projection 18. FIG. 6C is a schematic of a bubble trap 15 having a curved chamber 17 and inlet and outlet projections 12, 18. Unless otherwise noted, reference numerals in FIGS. 6A-6C refer to components that are the same as or generally similar to the components in the preceding figures.

As shown in FIG. 6A, the bubble trap 15 can include an inlet 16a, an outlet 16b, and a chamber 17. The chamber 17 can include one or more flow paths between the inlet 16a and the outlet 16b. In some embodiments, the inlet 16a and the outlet 16b can be positioned on opposite ends of the chamber 17, although any suitable arrangement is appreciated (e.g., on the same side, etc.). In some embodiments, the chamber 17 can be configured to trap gas (e.g., air) that flows in from the inlet 16a. To help trap air that flows into the chamber 17, the inlet 16a and/or outlet 16b can include one or more projections that extend into the chamber 17. This can advantageously position an opening of the inlet 16A and/or the outlet 16b away from a wall of the chamber where bubbles typically come to rest and/or accumulate during flow. In this way, the bubble trap 15 can be configured to trap air by confining it to a peripheral region of the chamber 17.

As shown in FIG. 6A, the trap 15 can include an outlet projection 18, including, for example, an outlet projection channel 19 in fluid communication with the outlet 16b. In such embodiments, the bubble trap 15 can define a flow path in which fluid can be forced to flow through the chamber 17 and the outlet projection channel 19 before it reaches and flows past the outlet 16b. In some embodiments, the one or more projections (e.g., projection 18) can be configured to inhibit bubbles from flowing directly from the inlet 16a to the outlet 16b. Since air tends to move upward against the force of gravity when in a liquid, bubbles tend to move toward the perimeter of the chamber 17 regardless of the bubble trap's orientation during flow. Advantageously, when the outlet 16b is positioned away from the periphery of the chamber 17, such as, for example, via the outlet projection 18, the bubble trap 15 can become an omnidirectional trap such that it is configured to trap air in the chamber 17 regardless of its orientation with respect to fluid flow or frame of reference (e.g., a neutral position). Although the projection channel is discussed herein and illustrated as being in fluid communication with the outlet 16a, it will be understood that any projection channel discussed herein may be an inlet projection channel in fluid communication with the inlet 16a In some embodiments, the one or more projections can be configured to maximize the air trapping ability and/or capability of the chamber 17. For example, in some embodiments, one or more projections (e.g., projection 18) can be positioned so that the opening 16c of the outlet projection channel 19 is near or in the center of the chamber 17. This can advantageously minimize the chance of air (e.g., one or more air bubbles) entering the outlet 16b after it comes to rest somewhere along the periphery of the chamber 17. In some embodiments, as shown in the drawings, the opening 16c of the outlet projection channel 19 may have an outlet center axis that is misaligned and/or offset from an inlet center axis of the inlet 16a. For example, as shown in the drawings, the opening 16c may have a center axis that is generally perpendicular to a plane defined by the opening 16c. In some embodiments, the center axis of the opening 16c may be offset from at least one of a center axis of the inlet 16a and a center axis of the outlet 16b. The opening 16c being misaligned from one or more of the inlet 16a and the outlet 16b breaks up a fluid pathway from the inlet 16a to the outlet 16b, thereby causing any air bubbles to rest along a periphery of the chamber 17. This may facilitate the collection of air within the bubble trap 15. As shown in FIG. 6A, in some embodiments, the outlet projection channel 19 can have a curved region near the tip of the outlet projection 18 such that the opening 16c of the outlet projection channel 19 is on the side of the outlet projection 18. This can further reduce the possibility of air entering the outlet projection channel 19 by removing all or the majority of direct paths from the inlet 16a to the opening 16c of the outlet projection channel 19, including, for example, the path that would otherwise exist from the inlet 16a to the outlet 16b in FIG. 6A (e.g., straight up) if the outlet projection channel 19 was instead straight and opened on the tip of the outlet projection 18 facing the inlet 16a. It will be appreciated that the outlet projection channel 19 can extend any suitable distance into the outlet projection 18 and that the curved region can be positioned along any suitable portion thereof.

In some embodiments, as shown in the drawings the opening 16c of the outlet projection channel 19 may be smaller relative to the inlet 16a of the bubble trap 15. The smaller size of the opening 16c can advantageously minimize that amount of air that is transferred through the outlet projection channel 19. The size of the opening 16c may increase the force required to push fluid into and/or through the outlet projection channel 19. The bubble trap 15 may be used with an automated compounder, as described herein, to drive fluid through the opening 16c of the bubble trap 15. However, it will be understood that the opening 16c of the bubble trap 15 may comprise any suitable size and/or shape to permit the transfer of fluid into and/or through the outlet projection channel 19. For example, the opening 16c of the outlet projection channel 19 may be configured to permit the transfer of fluid with the use of a manual compounder (e.g. a syringe). It will also be appreciated that the tips of the one or more projections (e.g., projection 18) can be configured to deflect bubbles that collide or otherwise come in close proximity to the outlet projection 18. It will be further appreciated that the shape of the one or more projections can have any suitable shape, such as, for example, straight, curved, cylindrical, tapered, conical (e.g., projection 18), etc. The flow of fluid and gas through the chamber 17 will be described in more detail below with reference to FIGS. 7A-7H.

The bubble trap 15 can have any suitable fluid capacity, or internal volume, including from about 1 cc to about 2 cc, from about 1 cc to about 5 cc, from about 1 cc to about 10 cc, greater than about 1 cc, greater than about 2 cc, and/or less than about 20 cc, among others (e.g., from about 3 cc to about 4 cc, from about 5 cc to about 10 cc, etc.). Any suitable portion of this fluid capacity can be used to trap air, such as, for example, 10% or less of the capacity, 20% or less of the capacity, 30% or less of the capacity, 40% or less of the capacity, 50% or less of the capacity, 60% or less of the capacity, or 70% or less of the capacity. Other percentages, more or less, as well as ranges, narrower or wider, are also appreciated. In some embodiments, the trapping capacity of the bubble trap 15 can be constant irrespective of the position of the bubble trap 15. In other embodiments, the trapping capacity of the bubble trap 15 can depend on myriad factors, such as the size and shape of the chamber 17, the length of the one or more projections and the locations of their openings, and/or the orientation of the bubble trap 15 with respect to fluid flow and gravity. For example, when in the orientation shown in FIG. 6A, the bubble trap 15 can be configured to have a trap region that extends from the top surface of the chamber 17 downward to the opening 16c of the outlet projection channel 19. In some embodiments, this trap region can correspond to one of the aforementioned capacities, among others. The bubble trap 15 illustrated in FIG. 6A can have the same or nearly the same capacity, for example, when it is rotated 90 degrees along any axis or combination axes, and/or when it is rotated any number of degrees along any combination of axes (e.g., one, two, and/or three axes). And in other embodiments, the bubble trap 15 illustrated in FIG. 6A can have one or more different capacities, for example, when it is rotated 90 degrees along any axis or combination axes, and/or when it is rotated any number of degrees along any combination of axes (e.g., one, two, and/or three axes). Various trap capacities as a function of a bubble trap's orientation are illustrated in FIGS. 7A-7H and will be described below.

As a result of some or all of the foregoing features, the bubble trap 15 can trap bubbles released from a source container (e.g., source container 39), a destination container (e.g., destination container 44), and/or a component connected to a fluid line. As shown in FIG. 6A, the chamber 17 provides a space for bubbles to collect and for liquid to flow through. As a result of this trapping capability, the bubble trap 15 can be used to advantageously reduce the risk of air embolisms, or at a minimum, reduce the frequency at which they occur. By inhibiting the flow of bubbles while permitting the flow of liquid, the bubble trap 15 can act as an air filter and filter air out of the flow path.

FIG. 6A' is a schematic of the bubble trap 15 of FIG. 6A with inlet and outlet luer connectors 20a, 20b. The male luer connector 20a can be any suitable male luer and the female luer connector 20b can be any suitable female luer. It will also be understood that, in some embodiments, any suitable arrangement of the male luer connector 20a and the female luer connector 20b is appreciated. For example, the bubble trap 15 may comprise a male luer connector located at least one of the inlet 16a and the outlet 16b and a female luer connector located at least one of the inlet 16a and the outlet 6. FIG. 6B, as described above, is a schematic of a bubble trap 15 having an outlet projection 18 and a curved as opposed to elongated chamber 17. In FIG. 6B, the inlet 16a and the outlet 16b are positioned on the same side of the housing 17 or otherwise in close proximity to one another such that the inlet 16a and the outlet 16b do not face or point toward each other. In such embodiments, the opening 16c of the outlet projection channel 19 can be positioned on the end of the outlet projection 18 without compromising the ability of the bubble trap 15 to trap air. In some embodiments, an inlet conduit 14a can be connected (e.g., attached, bonded, glued, welded, snapped, friction fit, removably attached, etc.) to the inlet 16a and an outlet conduit 14b can be connected to the outlet 16b.

FIG. 6C is a schematic of a bubble trap 15 having a curved chamber 17 and outlet and inlet and outlet luer connectors 20a, 20b. As shown in FIG. 6C, in some embodiments, the bubble trap 15 can include an inlet projection 12 having an inlet projection channel 13 and an outlet projection 18 having an outlet projection channel 19. The inlet projection 12 and the outlet projection 18 can have any suitable shape and/or configuration that inhibit the flow of bubbles into and/or past the outlet 16b. For example, as shown in FIG. 6C, the inlet projection 12 and the outlet projection 18 can be positioned on opposite ends of the chamber 17 with each extending toward its center. In such embodiments, both the inlet projection 12 and the outlet projection 18 can be configured to extend past the center of the chamber 17 so that a direct flow path does not exist between the inlet 16a and the outlet 16b. However, as described above with reference to FIG. 6A, the one or more inlet and outlet projections shown in FIG. 6C and take any suitable form. For example, although not shown, in some embodiments, either or both of the inlet and outlet projection channels 13, 19 can have a curve near the tip of their respective inlet or outlet projection 12, 18. In some embodiments, the inlet projection channel 18 can advantageously inhibit the inlet 16a from disturbing any bubbles that may have formed near the inlet 16a by positioning the inlet 16a away from the periphery of the chamber 17. Without the inlet projection 12, the inlet 16a may otherwise be prone to disturbing bubbles by, for example, ejecting them away from the periphery of the chamber (e.g., toward the opening 16c of the outlet projection channel 19), splitting large bubbles into smaller bubbles and dispersing them through the chamber 17, and the like.

FIGS. 7A-7H illustrate simplified schematics of a bubble trap 15 (e.g., the bubble trap 15 shown in FIG. 6A') trapping bubbles during fluid flow in 45 degree increments, according to some embodiments. Unless otherwise noted, reference numerals in FIGS. 7A-7H refer to components that are the same as or generally similar to the components in the preceding figures. Each FIG. 7A-7H illustrates an inlet 16a, a chamber 17, an outlet projection 18, an outlet projection channel 19, and an outlet 16b. More or less features are also appreciated. The direction of fluid flow is indicated by an arrow and air bubbles are represented by small circles. The air trapping capacity of the bubble trap 15 in each of these figures is shown, for example, by the area of the chamber 17 that lies above the dashed line labeled "C." As shown in FIGS. 7A-7H, in some embodiments, the area above line C can represent about 50% of the total fluid capacity of the chamber 17 in any given orientation, advantageously indicating that the bubble trap 15 in FIGS. 7A-7H is not only omnidirectional, but substantially uniformly omnidirectional. It will be appreciated that the bubble trap 15 can, in some embodiments, have a plurality of different trap capacities that correspond to two or more different orientations. It should be understood that an omnidirectional bubble trap according to some embodiments disclosed herein means that the bubble trap 15 has a minimum capacity for gas in all orientations. In some embodiments, that minimum is about 0.5 cc, about 1 cc, about 2 cc, about 3 cc, or more. As described above, the trap capacity can depend on a number of factors, including the size and shape of the chamber 17, the length and arrangement of the outlet projection 18 and/or an inlet projection 12 (not shown), the orientation of the bubble trap 15 with respect to fluid flow and gravity, and/or the rate of fluid flow. For example, in some embodiments, if the flow rate increases beyond a threshold rate, the trap capacity can decrease as a result of turbulent flow through the chamber 17 that can disturb the air above line C. However, in some embodiments, the bubble trap 15 can be configured to trap its maximum capacity for any suitable flow rate in any orientation. For example, as shown in FIGS. 7A-7H, the area above the dashed line "C" schematically represents the maximum amount of air that the bubble trap 15 can trap before it starts flowing through the outlet projection channel 19 and into the fluid line beyond the outlet 16b. In some embodiments, as the chamber 17 fills with air, the amount of dead space can be equally reduced. In some embodiments, a sensor can be configured to monitor and/or determine the amount of air in the bubble chamber 15 and indicate (e.g., audibly, visually, etc.) when the bubble trap 15 is approaching its trap capacity.

FIGS. 8A and 8B are two schematics of a bubble trap 15 with and without a vacuum applied. FIG. 8A is a schematic of a bubble trap with a vacuum applied and FIG. 8B is a schematic of the bubble trap of FIG. 8A filled with fluid. Unless otherwise noted, reference numerals in FIGS. 8A and 8B refer to components that are the same as or generally similar to the components in the preceding figures. In some embodiments, it can be advantageous to purge a fluid line having a bubble trap 15 (e.g., a fluid transfer module 45) of gas before filling a source and/or destination container 39, 45 with fluid. During a purge, a vacuum pressure can be applied to the bubble trap 15. To optimize the amount of air that can be removed from the bubble trap 15 during a purge, in some embodiments, the bubble trap 15 can comprise a rigid and/or semi-rigid outer housing that is configured to flex (e.g., shrink, collapse, etc.) when a vacuum is applied to the chamber 17. In this way, air can be evacuated (also referred to as withdrawn) from the chamber 17 during a purge. This can advantageously reduce the amount of air that needs to be trapped by the bubble trap 15 when delivering fluid to a patient from a source container 39 and/or filling a destination container 44. For example, when a vacuum is applied to the chamber 17, the rigid and/or semi-rigid outer housing can be configured to change shape and shrink as the size of the chamber 17 decreases as the vacuum increases. In some embodiments, the rigid, and/or semi-rigid outer housing can be configured to return to an expanded state (e.g., its original state before the vacuum was applied) after being collapsed by application of a vacuum. In some embodiments, the shape-restoring mechanism of the bubble trap 15 can correspond to the memory of the material (e.g., the material of the rigid and/or semi-rigid outer housing), the subsequent flow of fluid into and/or through the bubble trap 15, and/or one or more separate shape-restoring structures. In some embodiments, the entire bubble trap 15 can comprise the rigid and/or semi-rigid material configured to collapse upon application of a vacuum. In some embodiments, the rigid and/or semi-rigid material can comprise, for example, polyvinyl chloride (PVC), although any suitable material is appreciated. In some embodiments, the walls do not collapse under a vacuum and the vacuum applied is sufficient to remove the desired amount of gas from the system.

In some embodiments, the bubble trap 15 can be attached to a fluid line for use with any suitable pump and/or fluid transfer device (e.g., fluid transfer device 30, fluid transfer unit 200, and/or fluid pump assembly 224, etc.). For example, in some embodiments, the bubble trap 15 can be configured to be used with and/or fluidically connected to an ambulatory infusion pump, including infusion pumps that are configured to provide computerized ambulatory drug delivery. While the bubble trap 15 is discussed herein for use with a fluid transfer pump, it will be understood by one of skill in the art that a fluid transfer need not be used with the bubble trap 15. For example, the bubble trap 15 may be used to manually fill a destination container by hand.

In some embodiments, the bubble trap 15 can configured to be used with and/or fluidically connected to CADD® pumps manufactured by SMITHS MEDICAL®. FIGS. 9A and 9B are schematics of a bubble trap 15 in line with a fluid transfer module connected to a cassette. FIG. 9A is a schematic of a bubble trap 15 in fluid communication with a cassette with a reservoir and FIG. 9B is a schematic of a bubble trap 15 in fluid communication with a cassette without a reservoir, according to some embodiments. FIG. 9C is an example fluid transfer protocol for filling the cassette of FIG. 9A with medical fluid. Unless otherwise noted, reference numerals in FIGS. 9A-9C refer to components that are the same as or generally similar to the components in the preceding figures.

As shown in FIG. 9A, the pump 22 can include a removably attached cassette 24 with a reservoir 25 (e.g., source container 39 and/or destination container 44), as well as an air detection sensor 26. The air detection sensor 26 can be configured to indicate (e.g., audibly and/or visually) the presence of gas (e.g., air) in the fluid line that is discharged, for example, from the reservoir 25. In some embodiments, a bubble trap 15 can be connected to the fluid line that is connected to the reservoir 25 in the cassette. In FIG. 9A, the bubble trap 15, the cassette 24, and the fluid line therebetween can comprise a fluid transfer module (e.g., fluid transfer module 45), although more or less components and/or features are appreciated. For example, in some embodiments, one end of a male-to-male conduit 28 can be attached to the output 16b of the bubble trap 15, and the other end of the male-to-male conduit 28 can be configured to be in fluid communication with a patient and/or fluid destination container 44. A portion of the male-to-male conduit 28 can be positioned in the air detection sensor 26. It will be appreciated that the male-to-male conduit 28 can have any gender connector combination, including, for example, female-female, female-male, male-female, and/or male-male.

As described above, the position of the bubble trap 15 between the cassette 24a and the air detection sensor 26 can advantageously reduce the number of air detection alarms (e.g., indications) by trapping air before it is allowed to pass through the outlet 16b of the bubble trap 15 and into the male-to-male conduit 28. As a result, the use of the bubble trap 15 can advantageously translate into fewer treatment interruptions, and therefore enable the pump 22 to provide patients with more consistent and continuous treatment. This, in combination with the ability of the bubble trap 15 to reduce the risk of air embolisms, can increase patient confidence in the pump 22. By trapping air, the bubble trap 15 can enhance patient comfort by reducing and/or eliminating minor air embolisms that, while not lethal, can be nevertheless painful or uncomfortable. The bubble trap 15 can also prevent major air embolisms that are potentially lethal or would otherwise require medical intervention if not prevented from being infused into the patient. As will be described in more detail below with reference to FIG. 9C, the fluid transfer module 45 of FIG. 9A, including the bubble trap 15, the reservoir 25, and the fluid line therebetween, can be manually or automatically compounded to add the desired amount of fluid to the reservoir 25. For example, in some embodiments, the fluid transfer module 45 can be fluidically connected to a fluid transfer device (e.g., fluid transfer device 30, fluid transfer unit 200, and/or fluid pump assembly 224, etc.).

FIG. 9B is similar to FIG. 9A except that the cassette 24 does not include a reservoir 25. The fluid module 45 in FIG. 9B instead includes an external source container 39 and/or destination container 44, such as, for example, an IV bag, with a portion of the conduit between the IV bag and the bubble trap 15 positioned in the cassette 24.

FIG. 9C is an example fluid transfer protocol for filling the cassette of FIG. 9A with medical fluid. Each of the steps illustrated and/or described in connection with FIG. 9C can be performed using, for example, a syringe, or controlled or actuated, for example, in whole or in part, manually (e.g., a person) or automatically (e.g., by a computer processor of the pump 22, and/or by the computer processor positioned in or associated with fluid transfer management system 74). An advantage of some embodiments of this fluid transfer protocol 900 is that it can remove substantially all of the air from the reservoir 25 of the cassette 24 before the reservoir 25 is filled with fluid. Minimization of air in the destination container 44 (e.g., the cassette 24, reservoir 25, container 44, etc.) during the filling process can be particularly advantageous when the destination container is configured to be accessed from the top once it has been filled. As the air bubbles rise to the top of the destination container, they are more likely to be drawn from the container and transmitted toward the patient. The bubble trap 15 can be configured to catch the remaining residual air in the reservoir 25 by being positioned, as described above, anywhere in line with the reservoir 25 before the flow reaches the patient. For example, in some embodiments, an advantage of some embodiments of this fluid transfer protocol 900 is that it can remove about 98% of the air from the reservoir 25 of the cassette 24 before the reservoir 25 is filled with fluid. The bubble trap 15 can be configured to catch the remaining 2% of residual air in the reservoir 25 by being positioned, as described above, anywhere in line with the reservoir 25 before the flow reaches the patient. Other percentages are also appreciated. As with all embodiments in this specification, one or more of the steps of the fluid transfer protocol 900 can be performed alone, in one or more groups, or in a different ordering than is illustrated in FIG. 9C and/or than is described herein. For example, in some embodiments, the following steps can be modified and/or reordered to remove air from a fluid transfer module 45 attached to the fluid transfer device 30 shown in FIG. 1A, the fluid transfer system 86 illustrated in FIG. 1B, and/or the fluid transfer units 200 shown in FIGS. 2A$_i$ and 2A$_{ii}$ (e.g., shown, for example, in FIGS. 2C$_i$ and 2C$_{ii}$), among any other fluid transfer system. Similarly, in some embodiments, the bubble trap 15 can be used during the filling process to limit the air in the in the destination container and need not be used during the administration of the fluid from the destination container to the patient. Chronological terms such as "before" or "after" or "begin" or "start" or "end," or any similar terms, are provided only as examples and are not required in all embodiments. None of these steps is essential or indispensable.

The fluid transfer protocol 900 begins at the start block 902. The protocol 900 continues in block 904 with removing a cassette 24 from a package. In some embodiments, the cassette 24 can include a reservoir 25. In block 906, the protocol continues with attaching a bubble trap 15 (e.g., an omnidirectional bubble trap) to the cassette 24, the source container 39, and/or destination container 44. At block 908, the bubble trap 15 and the cassette 24 are fluidically connected to an automated or manual compounder (or a compounder capable of both), such as, for example, to a fluid transfer device (e.g., fluid transfer device 30 or a syringe configured to manually deliver fluid to the cassette 24). In 910, the protocol continues with applying a vacuum to the bubble trap 15 and the cassette 24 with the compounder to remove air inside of each and push it into a source container (e.g., source container 39 and/or destination container 44). In some embodiments, the compounder (or any suitable fluid transfer device) is capable of generating a vacuum in the bubble trap 15 and/or the cassette 24 (e.g., in the reservoir 25 of the cassette 24). For example, in some embodiments, the vacuum can be above or below atmospheric pressure. As described above, the vacuum applied can be sufficient to reduce the volume of the bubble trap 15, such as, for example, by collapsing the chamber 17 of the bubble trap 15. The flexible (e.g., collapsible) rigid and/or semi-rigid material of the bubble trap 15 can advantageously allow gas to be removed from the bubble trap 15 at lower vacuum pressure relative to the vacuum that would otherwise be required to remove an equivalent amount of gas from the bubble trap 15 if the material did not comprise flexible rigid and/or semi-rigid material. At block 912, the protocol continues with pushing medical fluid into the reservoir 25 of the cassette 24 with the compounder. In some embodiments, one or more fluids can be pushed into the reservoir 25 by the compounder. Blocks 914 and 916 of the protocol continue with detaching the bubble trap 15 and the cassette 24 from the fluid transfer device and then attaching the bubble trap 15 and the cassette 24 to the pump 22, respectively. At block 918, the process ends with pumping fluid in the reservoir 25 of the cassette 24 past the bubble trap 15 and into a patient. However, it will be understood, that in some embodiments, the process can end with pumping fluid in past the bubble trap 15 and into a source container 39 and/or destination container 44. From there, in some embodiments the fluid can be pumped from the source container 39 to the patient without the use of a bubble trap 15. Similarly, in some embodiments, the fluid can be pumped from the destination container 44 to the patient without the use of a bubble trap 15, With continued reference to infusion pumps such as the pump 22 illustrated in FIGS. 9A and 9B, FIGS. 10A and 10B illustrate examples of schematics in which the cassette 24 can be modified to trap and/or remove air. This is in contrast to FIGS. 9A and 9B, which illustrate examples of schematics in which the fluid line can be modified to trap and/or remove air, such as, for example, with the addition of a bubble trap 15. For example, FIG. 10A is a schematic of a cassette configured with a barrier 101. As another example, FIG. 10B is a schematic of a cassette configured to trap and/or remove air with a port 104. It will be appreciated that, in various embodiments, any of the features and/or embodiments described herein can be combined, including, for example, the embodiments shown in FIGS. 9A, 9B, 10A, and/or 10B, among others (e.g., the disclosure contemplated herein, including FIGS. 1-8B and 9C). Unless otherwise noted, reference numerals in FIGS. 10A and 10B refer to components that are the same as or generally similar to the components in the preceding figures.

As shown in FIG. 10A, a barrier 101 can be added to the reservoir 25 of the cassette 24 to create a partition in the reservoir 25. In some embodiments, the barrier can be, for example, a heat sealed barrier, although any suitable barrier is appreciated. In some embodiments, the reservoir 25 can include one or more barriers. The barrier 101 can advantageously create a bubble collection region 102 (also referred to as a subreservoir or subchamber) that is spaced apart from the outlet of the reservoir 25, as well as an outlet region 103 (also referred to as an outlet chamber). While the barrier 101 is illustrated in FIG. 10A as having a particular shape and size in relation to the reservoir 25, it will be understood by one skilled in the art that the barrier 101 may comprise any shape or size capable of creating a bubble collection region 102. In some embodiments, the barrier 101 can prevent some or all of the air in the reservoir 25 from being pumped from the reservoir 25 by trapping it in the bubble collection region 102.

In some embodiments, the outlet region 103 may be located on a bottom portion of the reservoir 25. As air bubbles rise to the top of the reservoir 25, the location of the outlet region 103 on the bottom portion can reduce the amount of air bubbles that are passed through the outlet region 103 and one or more connectors 105, 106. As a result, the location of the outlet region 103 may advantageously reduce the number of air detection alarms and translate into fewer treatment interruptions, and therefore enable the pump 22 to provide patients with more consistent and continuous treatment. This, in combination with the ability of the bubble trap 15 to reduce the risk of air embolisms, can increase patient confidence in the pump 22

As illustrated in FIG. 10B, the port 104 can be, for example, an adapter configured to attach to a fluid transfer device (e.g., fluid transfer device 30, a syringe, etc.) configured to apply a vacuum to the reservoir 25 before it is filled with fluid. In some embodiments, the port 104 may be configured to remove air bubbles present in the reservoir 25 after the pump 22 has filled the reservoir 25 with fluid. The port 104 can be located at a top portion of the reservoir 25, as shown in FIG. 10B, to facilitate the removal of air bubbles that rise to the top of the reservoir 25. As described above, this can advantageously reduce the amount of air in the reservoir 25 and thereby reduce the chances of giving a patient an air embolism. It can also advantageously reduce the frequency at which the air detection sensor 26 indicates the presence of air in the line. In some embodiments, the port 104 can allow gas to be evacuated from the reservoir 25 and/or can allow the infusion and/or insertion of drugs into the reservoir 25 when needed. As illustrated in FIGS. 10A-10B, in some embodiments, the cassette may be in fluid communication with one or more connectors 105, 106. Connectors 105, 106 may comprises one or more luer connectors, such as a female or male medical connector having a luer fitting.

Any system, method, and device described in this application can include any combination of the preceding features described in this and other paragraphs, among other features and combinations described herein, including features and combinations described in subsequent paragraphs.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow. Moreover, language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

The following is claimed:

1. A method of using an inline bubble trap device to reduce an amount of air prior to transfer of a medical fluid through the inline bubble trap and a medical fluid line in fluid communication therewith, the method comprising:
providing the medical fluid line;
providing the inline bubble trap device comprising:
a resilient housing at least partially defining a chamber comprising an interior chamber volume;
an inlet comprising an inlet exterior end extending away from the chamber and an inlet projection extending towards a central region of the chamber and comprising an inlet opening and an inlet channel in fluid communication with the inlet;
an outlet comprising an outlet exterior end extending away from the chamber and an outlet projection extending towards the central region of the chamber and comprising an outlet opening and an outlet channel in fluid communication with the outlet; and
the inlet projection and the outlet projection overlap and at least a portion of the inlet projection and at least a portion of the outlet projection contact each other within the chamber; wherein
the bubble trap device is configured to inhibit movement of gas between the inlet and the outlet, and
purging the inline bubble trap device and the medical fluid line, the purging comprising:
subjecting the inline bubble trap device and the medical fluid line to a vacuum; and
at least partially collapsing the resilient housing of the inline bubble trap device to reduce the interior chamber volume.

2. The method of claim 1, further comprising removing the vacuum to expand the resilient housing and to increase the interior chamber volume.

3. The method of claim 1, further comprising:
transferring fluid through the medical fluid line and the inline bubble trap; and trapping gas that flows into the inline bubble trap in the chamber of the inline bubble trap device.

4. The method of claim 1, further comprising:
placing the inline bubble trap in fluid communication with at least one of a fluid transfer device, a fluid source, and a fluid destination;
transferring fluid from the fluid source to the fluid destination through the inline bubble trap device with the fluid transfer device; and
inhibiting transfer of gas from the fluid source, through the outlet of the bubble trap, and into the fluid destination.

5. The method of claim 3, placing the inline bubble trap in direct fluid communication with the fluid source.

6. The method of claim 3, placing the inline bubble trap in direct fluid communication with the fluid destination.

7. The method of claim 1, placing the inline bubble trap in fluid communication with a cassette.

8. The method of claim 1, wherein the outlet opening is positioned on a side of the outlet projection.

9. The method of claim 1, wherein the inlet opening is positioned on a side of the inlet projection.

10. The method of claim 1, wherein the inlet and the outlet are on opposite ends of the chamber.

11. The method of claim 1, wherein the inlet exterior end comprises luer fitting.

12. The method of claim 1, wherein the outlet exterior end comprises luer fitting.

* * * * *